US012747454B2

(12) United States Patent
Kohn et al.

(10) Patent No.: US 12,747,454 B2
(45) **Date of Patent: *Sep. 29, 2026**

(54) SELF-INACTIVATING LENTIVIRAL VECTOR COMPRISING A FOXP3 EXPRESSION CASSETTE

(71) Applicants: The Regents of the University of California, Oakland, CA (US); The Board of Trustees of the Leland Stanford Junior University, Stanford, CA (US)

(72) Inventors: Donald B. Kohn, Tarzana, CA (US); Maria Grazia Roncarolo, Menlo Park, CA (US); Roger Paul Hollis, Los Angeles, CA (US); Katelyn E. Masiuk, Santa Monica, CA (US); Rosa Bacchetta, Menlo Park, CA (US)

(73) Assignees: THE REGENTS OF THE UNIVERSITY OF CALIFORNIA, Oakland, CA (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/754,883

(22) Filed: Jun. 26, 2024

(65) Prior Publication Data

US 2024/0336935 A1 Oct. 10, 2024

Related U.S. Application Data

(63) Continuation of application No. 16/640,306, filed as application No. PCT/US2018/047586 on Aug. 22, 2018, now Pat. No. 12,060,566.

(Continued)

(51) Int. Cl.
*C12N 15/86* (2006.01)
*C12N 5/0789* (2010.01)

(52) U.S. Cl.
CPC ........... *C12N 15/86* (2013.01); *C12N 5/0647* (2013.01); *C12N 2501/60* (2013.01); *C12N 2740/16043* (2013.01)

(58) Field of Classification Search
CPC .......... C12N 15/86; C12N 2740/16043; C12N 2501/60
See application file for complete search history.

(56) References Cited

U.S. PATENT DOCUMENTS 12,060,566 B2 * 8/2024 Kohn ................ A61K 38/1709
2009/0325868 A1 12/2009 Liu et al.

(Continued)

FOREIGN PATENT DOCUMENTS

EP 1446500 B1 8/2008
JP 2004208548 A 7/2004
WO WO-2016201047 A1 12/2016

OTHER PUBLICATIONS

Miyoshi, H., et al., Oct. 1998, Development of a Self-Inactivating Lentivirus Vector, J. Virol. 72(10):8150-8157.*

(Continued)

*Primary Examiner* — Jeffrey S Parkin
(74) *Attorney, Agent, or Firm* — Mark S. Cohen; PEARL COHEN LLP

(57) ABSTRACT

In various embodiments, lentiviral vectors expressing FoxP3 using the endogenous gene elements to regulate physiologic gene expression of FoxP3 are provided herein as well as uses of such vectors.

10 Claims, 34 Drawing Sheets

Specification includes a Sequence Listing.

Related U.S. Application Data

(60) Provisional application No. 62/548,891, filed on Aug. 22, 2017.

(56) References Cited

U.S. PATENT DOCUMENTS

| | | | |
|---|---|---|---|
| 2014/0065110 | A1 | 3/2014 | Nolta et al. |
| 2016/0038541 | A1 | 2/2016 | Stripecke et al. |
| 2016/0046685 | A1 | 2/2016 | Nolta et al. |
| 2016/0230191 | A1 | 8/2016 | Vink et al. |

OTHER PUBLICATIONS

Zufferey, R., et al., Dec. 1998, Self-Inactivating Lentivirus Vector for Safe and Efficient In Vivo Gene Delivery, J. Virol. 72(12): 9873-9880.*

Aiuti, A., et al., "Lentivirus-based Gene Therapy of Hematopoietic Stem Cells in Wiskott-Aidrich Syndrome", SCIENCE, vol. 341, No. 6148, Jul. 11, 2013, 29 pages, XP002789810.

Allan, S.E., et al., "Generation of Potent and Stable Human CD4+ T Regulatory Cells by Activation-independent Expression of FOXP3", Molecular Therapy, vol. 16, No. 1, Jan. 1, 2008, pp. 194-202, XP055133056.

Elhage, R., et al., "C-Terminal Cleavage of Human Foxp3 at a Proprotein Convertase Motif Abrogates its Suppressive Function", Scandinavian Journal of Immunology, vol. 81, No. 4, Mar. 20, 2015, pp. 229-239, XP055801580.

Extended European Search Report dated May 21, 2021, in Application No. EP18848409.1 [UCLAP188EP].

International Preliminary Report on Patentability dated Mar. 5, 2020, in PCT Application No. PCT/US2018/047586 [UCLAP188WO].

International Search Report and Written Opinion dated Nov. 14, 2018 in Application No. PCT/US2018/047586 [UCLAP188WO].

Jin., C, "Improvement of Adoptive T-Cell Therapy for Cancer", Dissertation Journal of the University of Uppsala, 2016, 64 pages. http://www.diva-portal.org/smash/record.jsf?pid=diva2%3A953234dswid=-2773.

JP Office Action dated Jul. 25, 2022, in Application No. JP2020-511428 with English translation [UCLAP188JP].

Kim, H. et al., "CREB/ATF-dependent T Cell Receptor-induced FoxP3 Gene Expression: A Role for DNA Methylation", The Journal of Experimental Medicine, 2007, vol. 204, No. 7, pp. 1543-1551.

Masiuk, et al., "Lentiviral Gene Therapy in HSCs Restores Lineage-Specific Foxp3 Expression and Suppresses Autoimmunity in a Mouse Model of IPEX Syndrome", Cell Stem Cell, vol. 24, No. 2, pp. 309-317, XP085595382, 2019.

Tone, Y. et al., "Smad3 and NFAT cooperate to induce Foxp3 expression through its enhancer", Nature Immunology, 2008, vol. 9, No. 2, pp. 194-202.

Zheng, Y., et al., "Role of conserved non-coding DNA elements in the Foxp3 gene in regulatory T-cell fate", Nature, Feb. 2010, vol. 463, No. 7282, pp. 808-812.

Communication regarding Third-Party Pre-Issuance Submission dated Jan. 24, 2023, 16 pages.

European Office Action dated Jan. 27, 2023 in Application No. EP18848409.1 [UCLAP188EP].

Passerini et al., "CD4+ T cells from IPEX patients convert into functional and stable regulatory T cells by FOXP3 gene transfer", Sci. Translat. Med., Dec. 2013; 5(215):1-11.

Cante-Barrett et al., "Lentiviral gene transfer into human and murine hematopoietic stem cells: size matters", BMC Res. Notes, 2016; 9(312):1-6.

Kumar et al., "Systematic determination of the packaging limit of lentiviral vectors", Human Gene Therapy, Oct. 2001; 12:1893-1905.

Urbinati et al., "Potentially therapeutic levels of anti-sickling globin gene expression following lentivirus-mediated gene transfer in sickle cell disease bone marrow CD34+ cells", Exp. Hematol., 2015, 43:346-351.

Zufferey et al., "Self-inactivating lentivirus vector for safe and efficient in vivo gene delivery", J. Viral., Dec. 1998, 72(12):9873-9880.

Baldwin et al., "Enrichment of Human Hematopoietic Stem/Progenitor Cells Facilitates Transduction for Stem Cell Gene Therapy", Stem Cells, Jan. 2015; 33(5): 1532-1542.

Barzaghi et al., "Long-Term Follow-up of IPEX Syndrome Patients after Different Therapeutic Strategies: An International Multicenter Retrospective Study", Journal of Allergy and Clinical Immunology, Mar. 2018; 141(3): 1036-1049.

Bennett et al., "The Immune Dysregulation, Polyendocrinopathy, Enteropathy, X-Linked Syndrome (IPEX) Is Caused by Mutations of FOXP3", Nat. Genet., Jan. 2001; 27(1): 20-21.

Billerbeck et al., "Development of Human CD4+FoxP3+ Regulatory T Cells in Human Stem Cell Factor-, Granulocyte-Macrophage Colony-Stimulating Factor-, and Interleukin-3-Expressing NOD-SCID IL2Rγ(Null) Humanized Mice", Blood, Mar. 2011; 117(11): 3076-3086.

Cavazzana et al., "Transfusion Independence and HMGA2 Activation after Gene Therapy of Human β-Thalassaemia", Nature, Sep. 2010; 467(7313): 318-322.

Chen et al., "Conversion of Peripheral CD4+CD25-Naive T Cells to CD4+CD25+ Regulatory T Cells by TGF-Beta Induction of Transcription Factor Foxp3", J. Exp. Med., Dec. 2003; 198(12): 1875-1886.

Cooper et al., "Highly Efficient Large-Scale Lentiviral Vector Concentration by Tandem Tangential Flow Filtration", J. Virol. Meth., Oct. 2011; 177(1): 1-9.

Curotto De Lafaille et al., "CD25-T Cells Generate CD25+Foxp3+ Regulatory T Cells by Peripheral Expansion", J. Immunol., 2004; 173(12): 7259-7268.

Dull et al., "A Third-Generation Lentivirus Vector with a Conditional Packaging System", J. Virol., Nov. 1998; 72(11): 8463-8471.

Fontenot et al., "Foxp3 Programs the Development and Function of CD4+CD25+ Regulatory T Cells", Nat. Immunol. Mar. 2003; 4(4): 330-336.

Guo et al., "Functional Defects in CD4+ CD25high FoxP3+ Regulatory Cells in Ankylosing Spondylitis", Sci. Rep., Nov. 2016; 6(1): 37559.

Haertle et al., "Metabolism and Anti-Human Immunodeficiency Virus-1 Activity of 2-Halo-2', 3'-Dideoxyadenosine Derivatives", J. Biol. Chem., Apr. 1988; 263(12): 5870-5875.

Harada et al., "Infection of HTLV-III/LAV in HTLV-I-Carrying Cells MT-2 and MT-4 and Application in a Plaque Assay", Science, Aug. 1985; 229(4713): 563-566.

Haribhai et al., "A Requisite Role for Induced Regulatory T Cells in Tolerance Based on Expanding Antigen Receptor Diversity", Immunity, Jul. 2011; 35(1): 109-122.

Kasow et al., "Therapeutic in vivo Selection of Thymic-Derived Natural T Regulatory Cells Following Non-Myeloablative Hematopoietic Stem Cell Transplant for IPEX", Clin. Immunol., Nov. 2011; 141(2): 169-176.

Khattri et al., "The Amount of Scurfin Protein Determines Peripheral T Cell Number and Responsiveness", J. Immunol., 2001; 167(11): 6312-6320.

Li et al., "Function of a Foxp3 Cis-Element in Protecting Regulatory T Cell Identity", Cell, Aug. 2014; 158(4): 734-748.

Liu et al., "Genomic Discovery of Potent Chromatin Insulators for Human Gene Therapy", Nat. Biotechnol., Jan. 2015; 33(2): 198-203.

Logan et al., "Factors Influencing the Titer and Infectivity of Lentiviral Vectors", Hum. Gene Ther., Oct. 2004; 15: 976-988.

Morgan et al., "Hematopoietic Stem Cell Gene Therapy: Progress and Lessons Learned", Cell Stem Cell, Nov. 2017; 21(5): 574-590.

Riley et al., "Human T Regulatory Cell Therapy: Take a Billion or So and Call Me in the Morning", Immunol., May 2009; 30(5): 656-665.

Safinia et al., "Adoptive Regulatory T Cell Therapy: Challenges in Clinical Transplantation", Curr. Opin. Organ Transpl., Aug. 2010; 15(4): 427-434.

(56) References Cited

OTHER PUBLICATIONS

Santoni et al., "Ectopic FOXP3 Expression Preserves Primitive Features of Human Hematopoietic Stem Cells While Impairing Functional T Cell Differentiation", Sci. Rep., Nov. 2017; 7(1): 15820.
Seidel et al., "Selective Engraftment of Donor CD4+25high FOXP3-Positive T Cells in IPEX Syndrome after Nonmyeloablative Hematopoietic Stem Cell Transplantation", Blood, May 2009; 113(22): 5689-5691.
Tai et al., "Foxp3 Transcription Factor Is Proapoptotic and Lethal to Developing Regulatory T Cells Unless Counterbalanced by Cytokine Survival Signals", Immunity, Jun. 2013; 38(6): 1116-1128.
Toker et al., "Active Demethylation of the Foxp3 Locus Leads to the Generation of Stable Regulatory T Cells within the Thymus", J. Immunol., Apr. 2013; 190(7): 3180- 3188.
Wildin et al., "X-Linked Neonatal Diabetes Mellitus, Enteropathy and Endocrinopathy Syndrome Is the Human Equivalent of Mouse Scurfy", Nat. Genet., Jan. 2001; 27(1): 18-20.
Wunderlich et al., "OKT3 Prevents Xenogeneic GVHD and Allows Reliable Xenograft Initiation from Unfractionated Human Hematopoietic Tissues", Blood, Jun. 2014; 123(24): e134-144.
Yue et al., "Control of Foxp3 Stability through Modulation of TET Activity", J. Exp. Med., Feb. 2016; 213(3): 377-397.

* cited by examiner

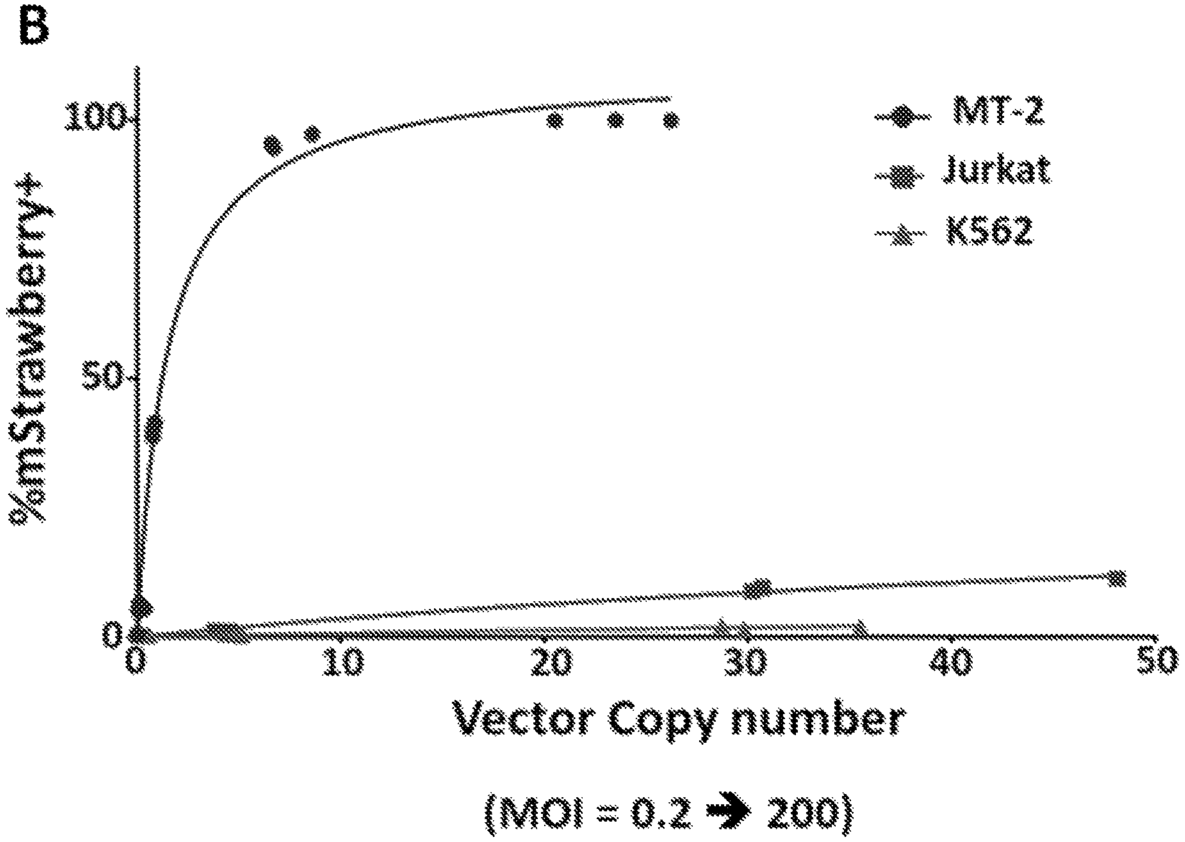
*Fig. 1, cont'd.*

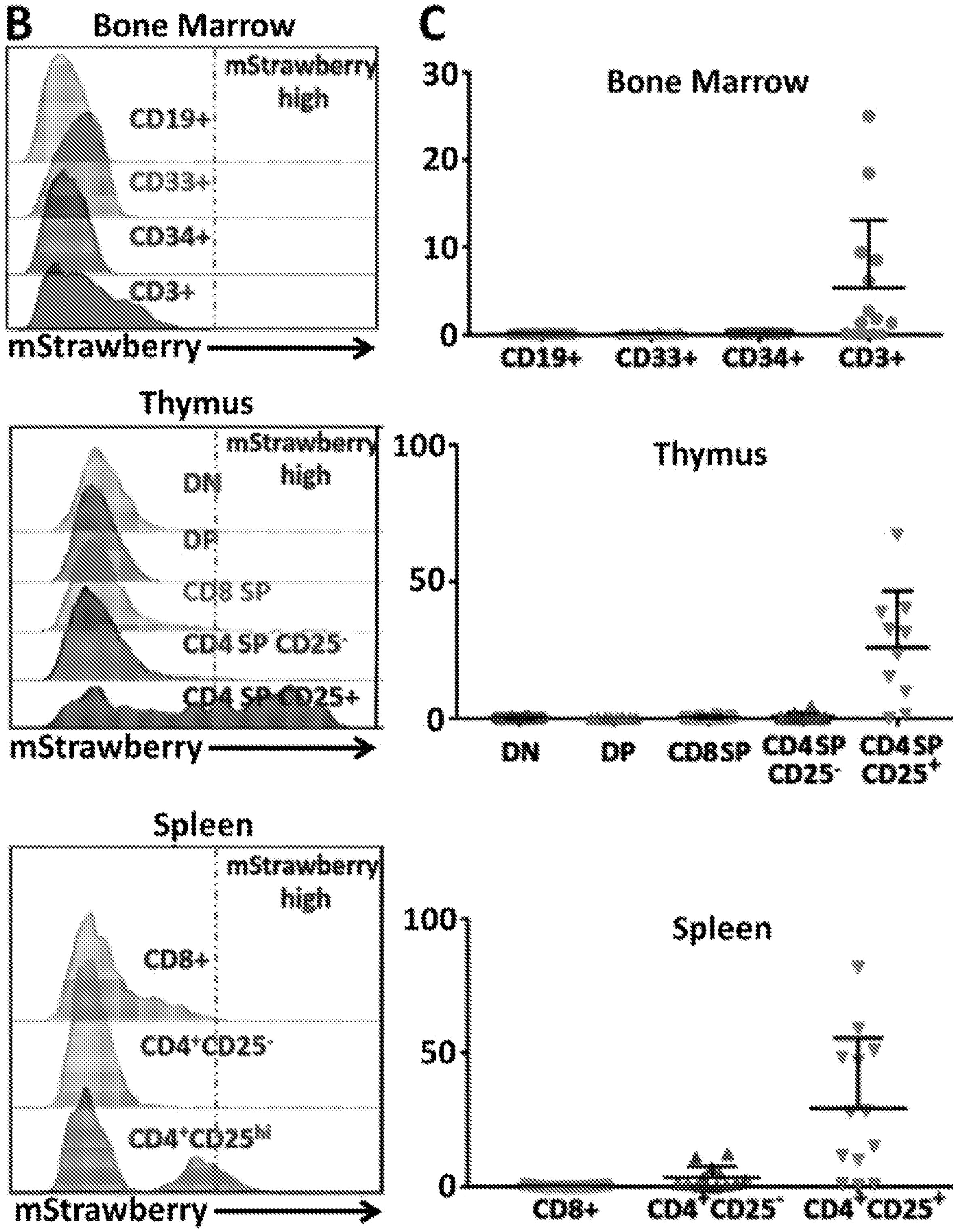
*Fig. 3, cont'd.*

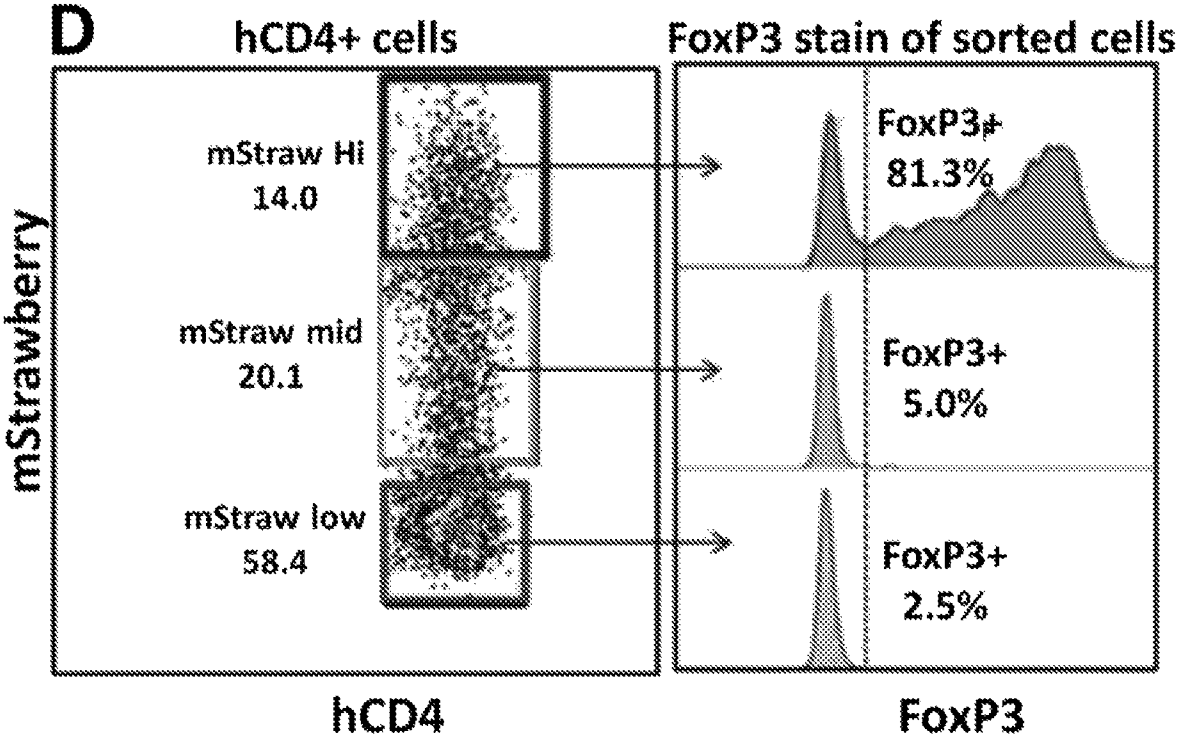
*Fig. 3, cont'd.*

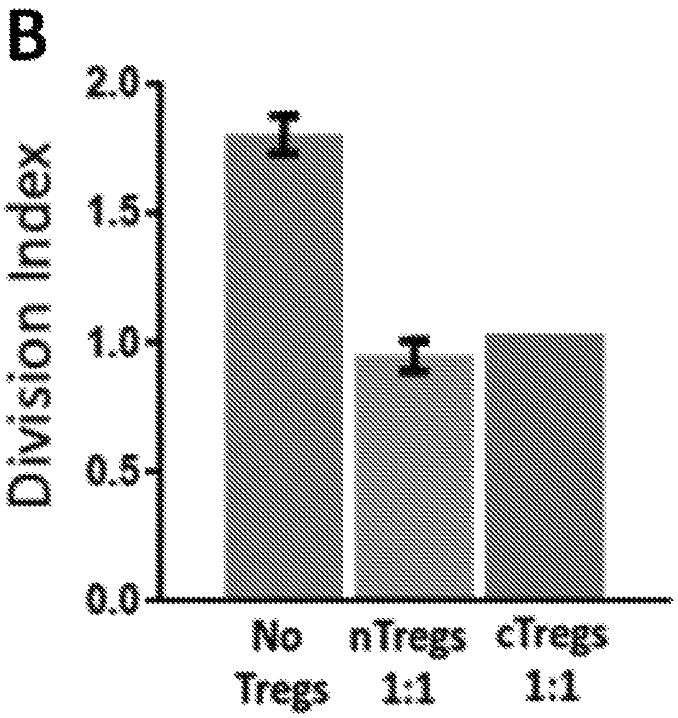
*Fig. 4, cont'd.*

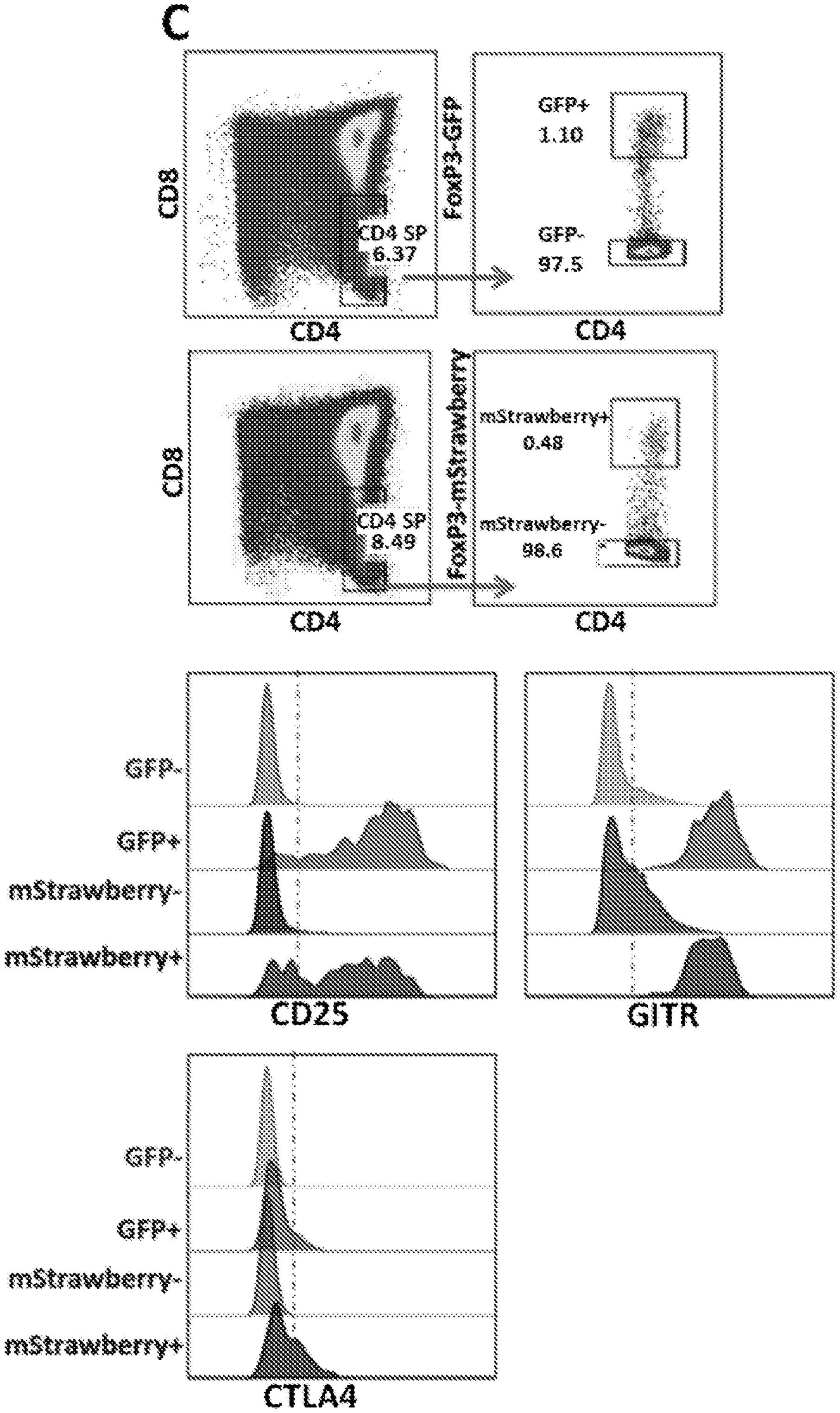
*Fig. 4, cont'd.*

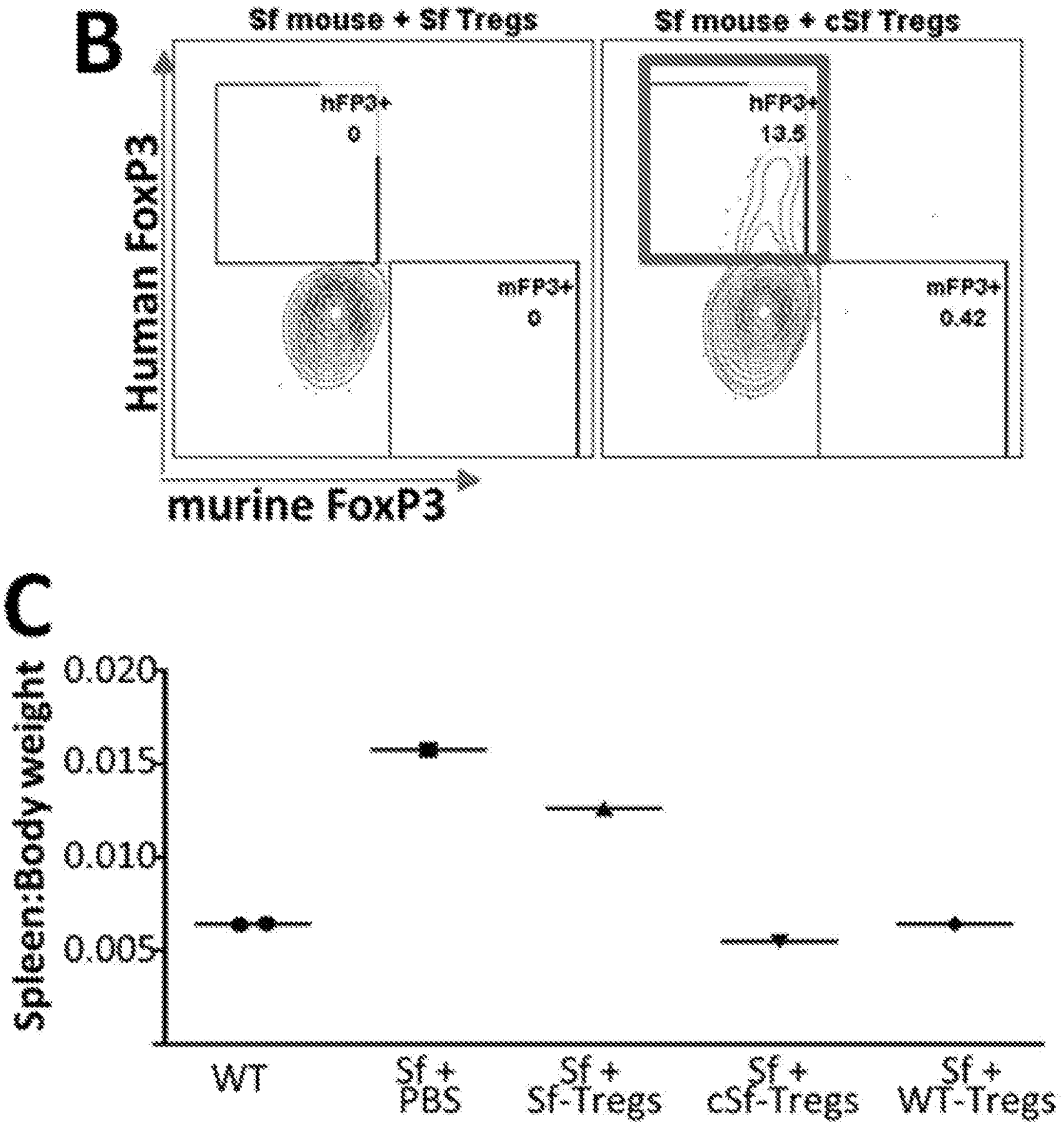
*Fig. 5, cont'd.*

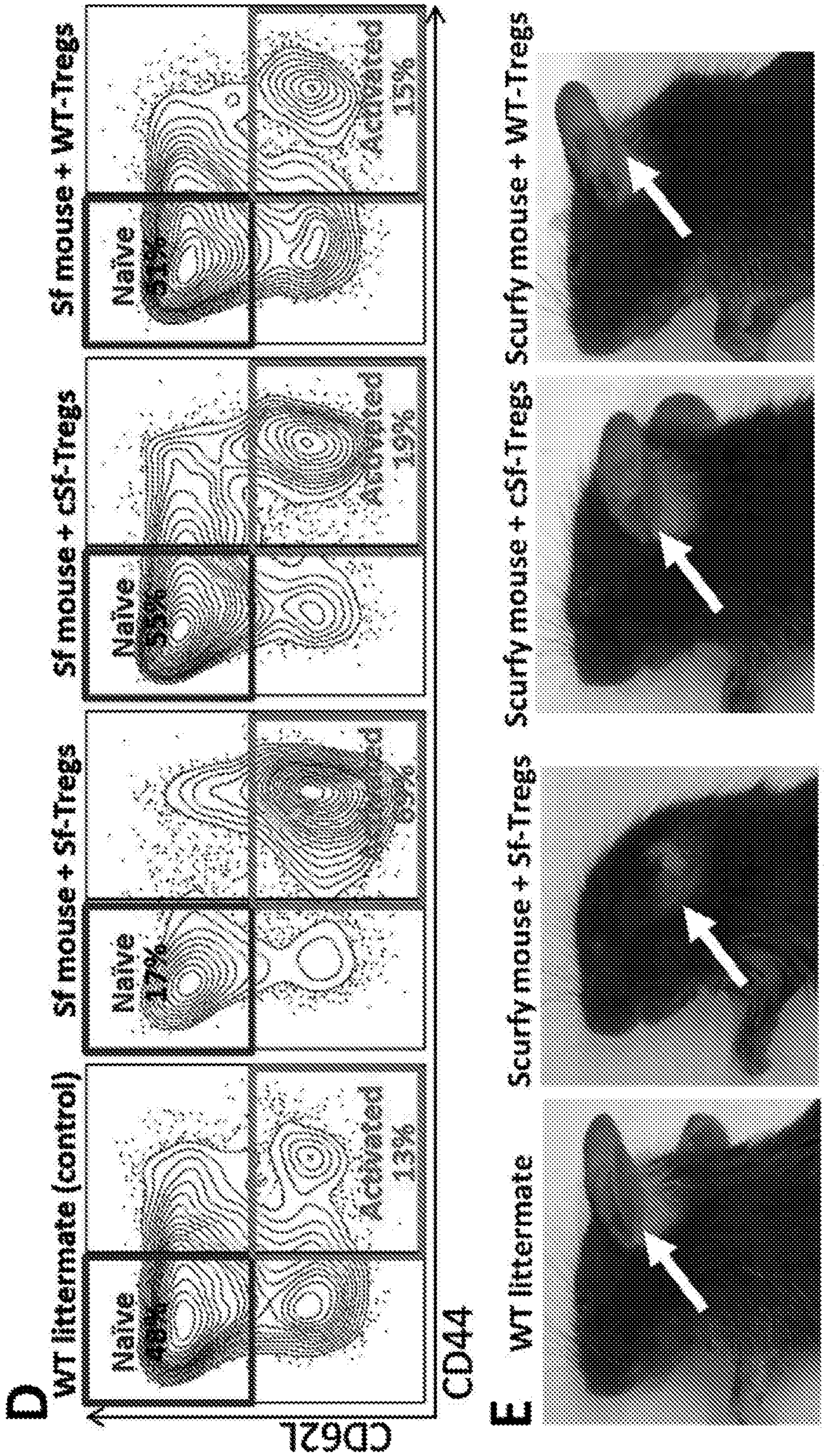
*Fig. 5, cont'd.*

FoxP3 Lentiviral Vector

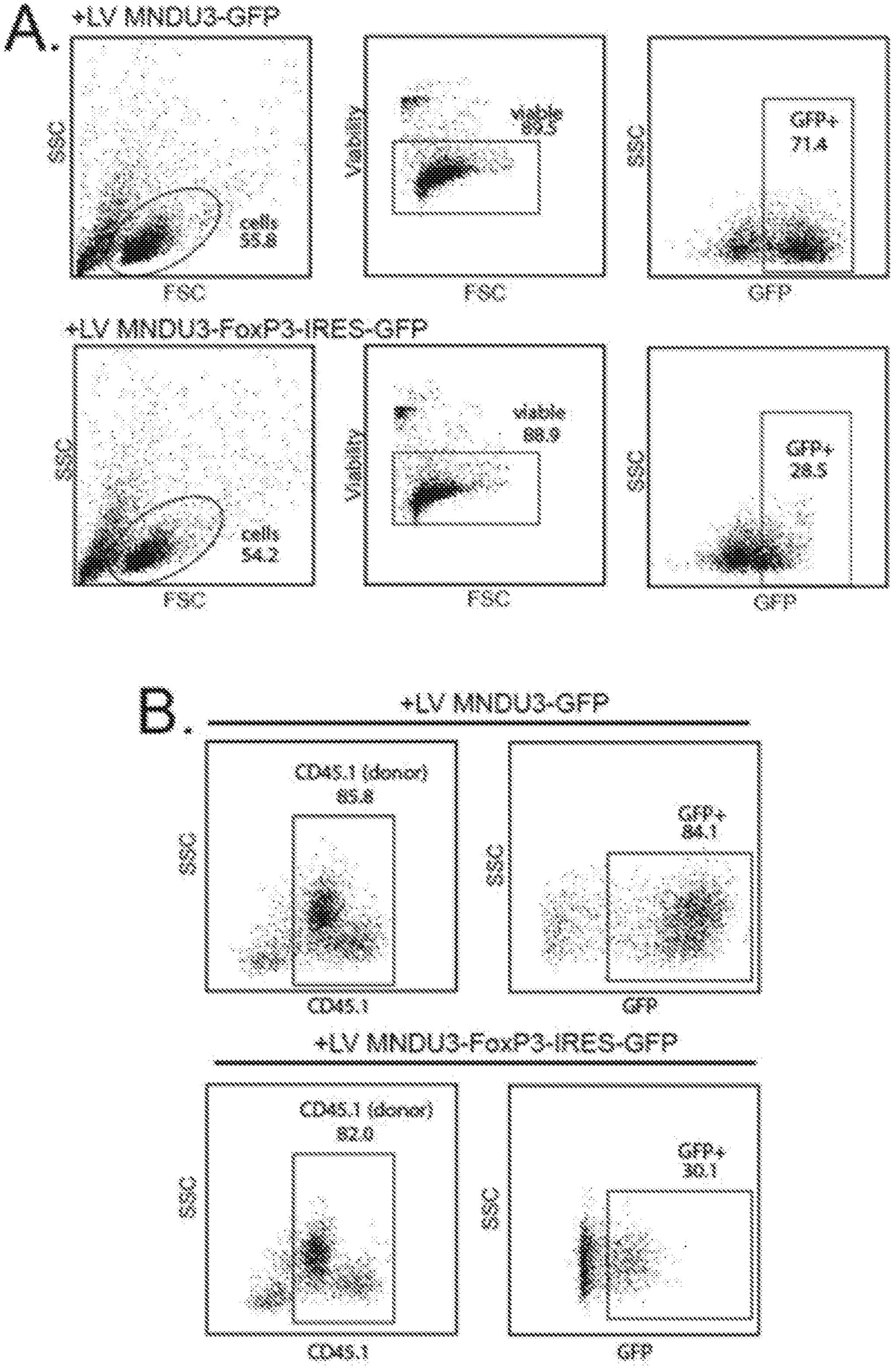
*Fig.* 8

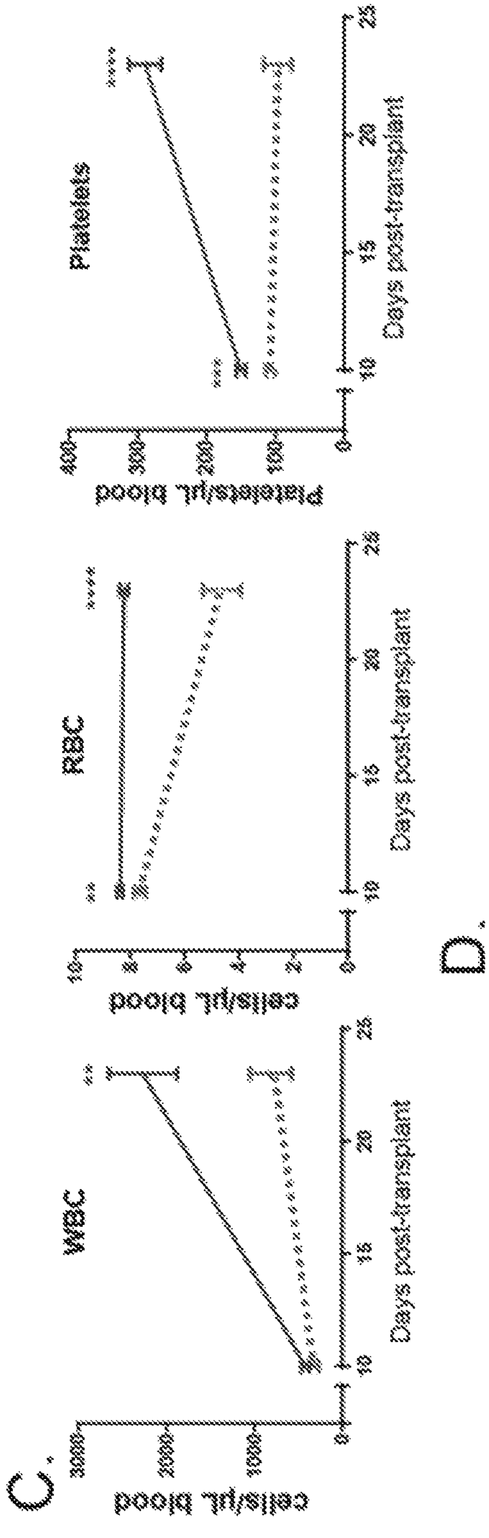
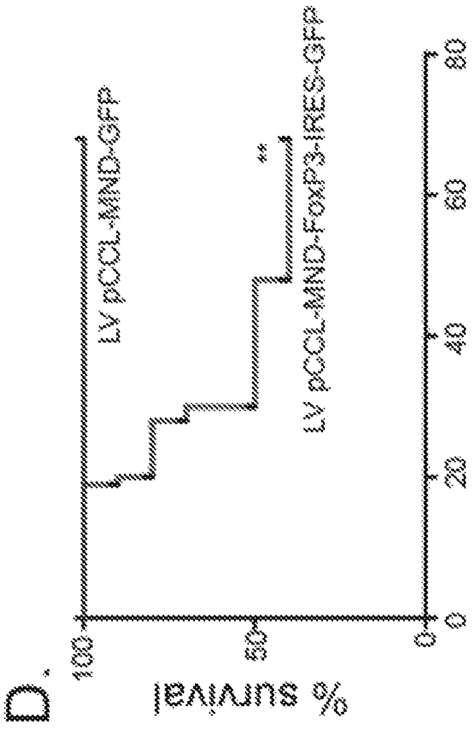
Fig. 8, cont'd.

E.
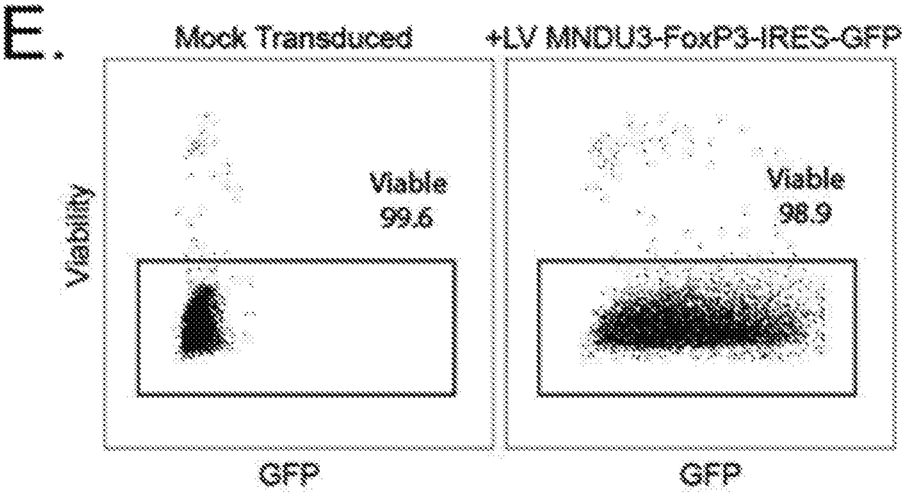
F.
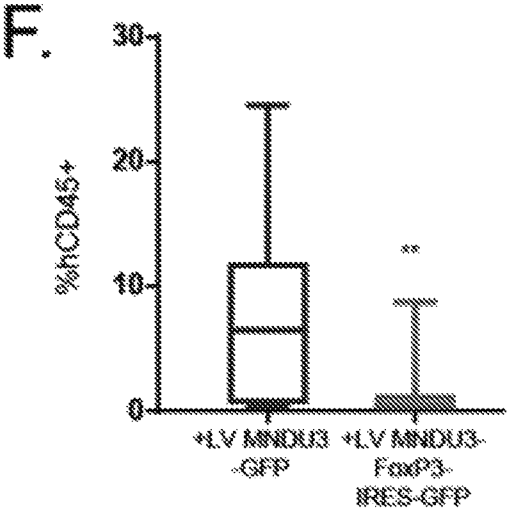
*Fig. 8, cont'd.*

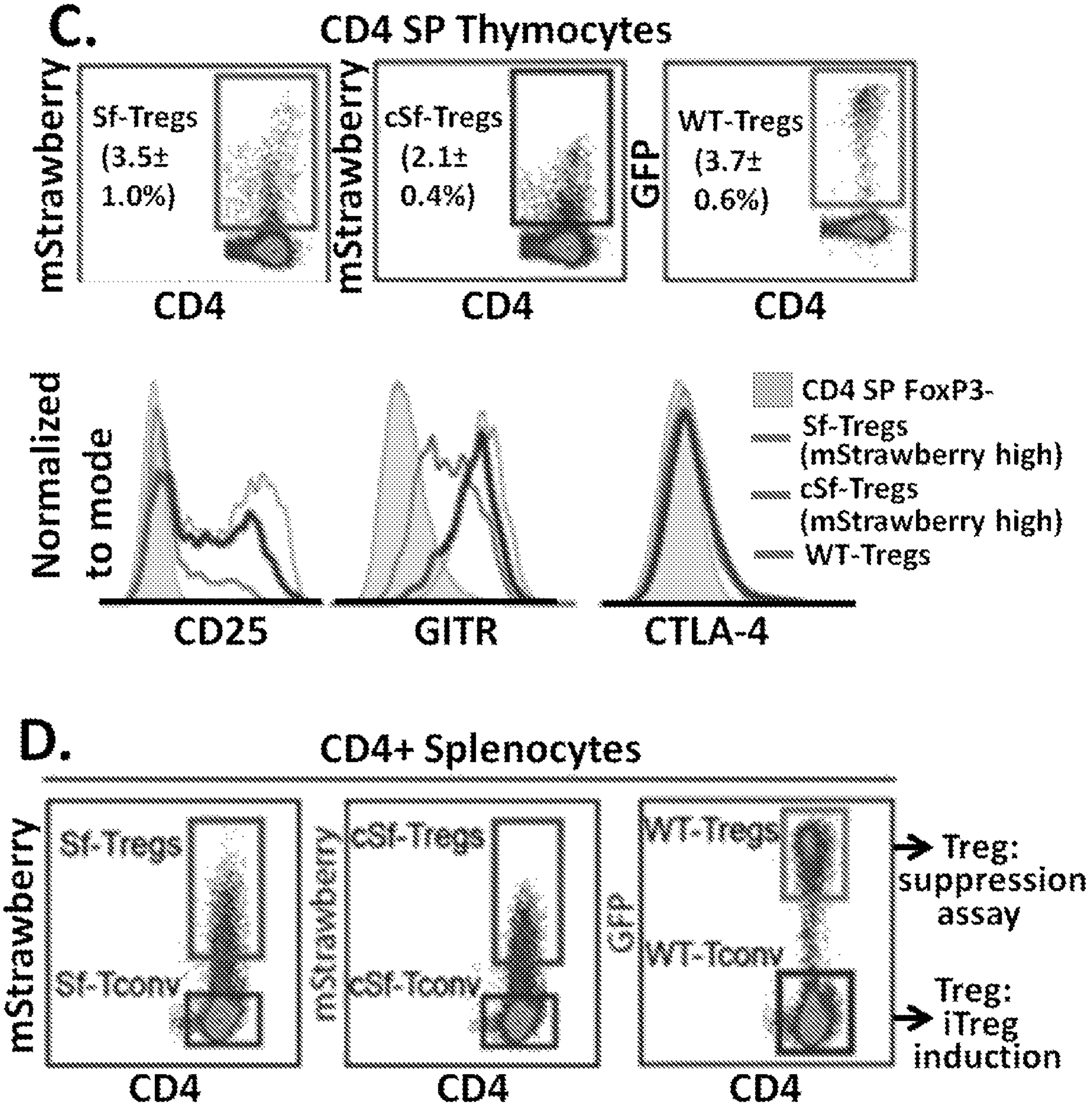
*Fig. 11, cont'd.*

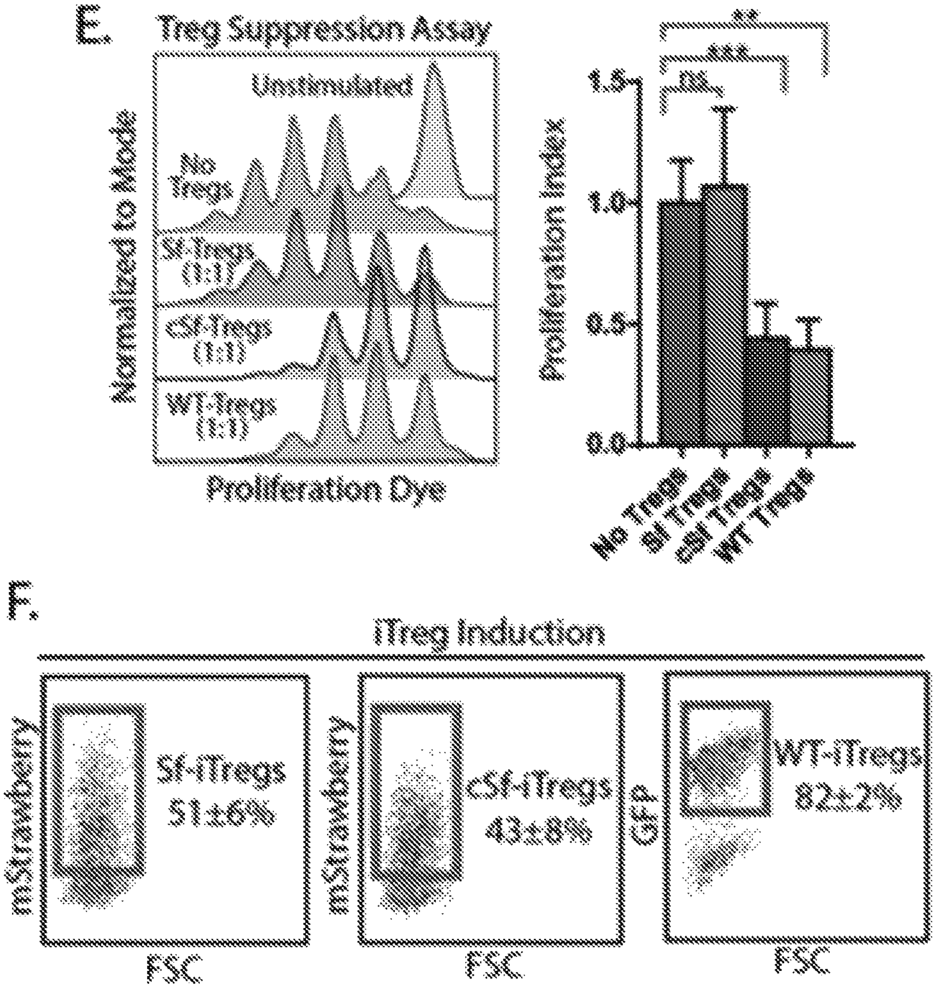
*Fig. 11, cont'd.*

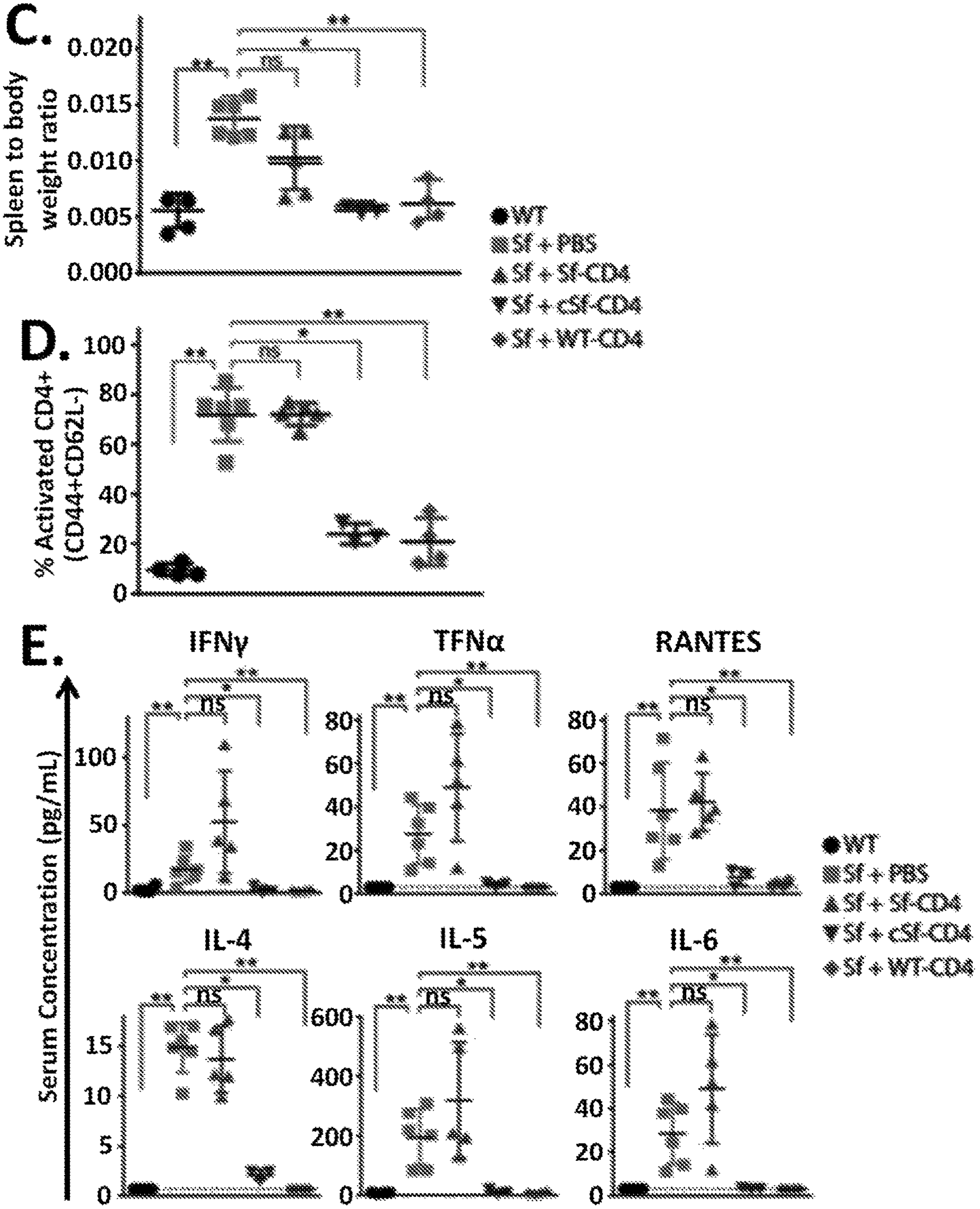
*Fig. 12, cont'd.*

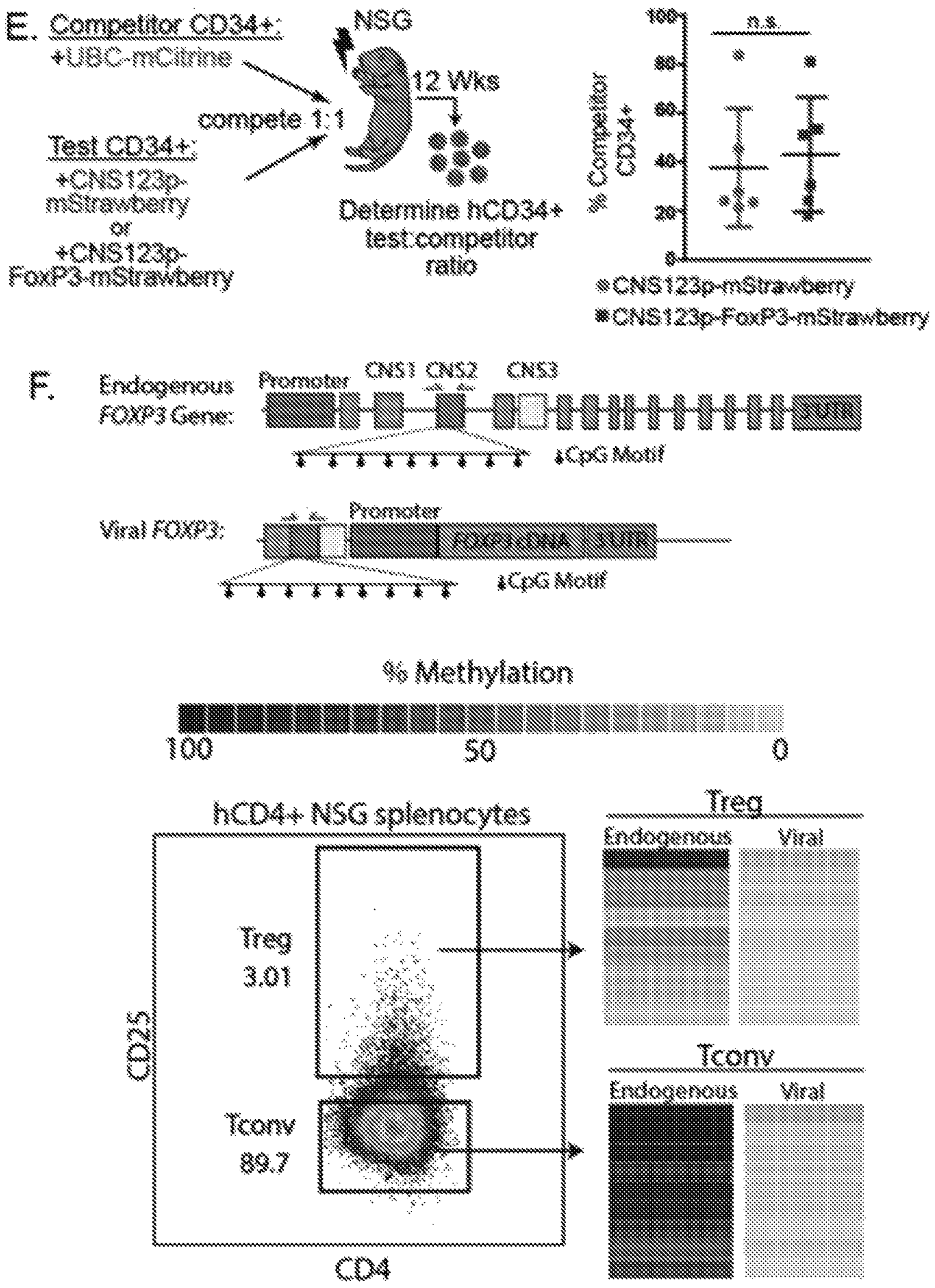
*Fig. 13, cont'd.*

A.

| Mouse | Sex | Arm | CD4 cell dose | CD4 VCN | % mStrawberry+ or %GFP+ of total CD4 | Putative Treg Dose |
|---|---|---|---|---|---|---|
| 1 | M | **WT + PBS** | - | - | - | - |
| 2 | M | Sf + PBS | - | - | - | - |
| 3 | M | Sf + Sf-CD4 | $8.0x10^{6}$ | 7.47 | 10.80% | $8.6x10^{5}$ |
| 4 | M | Sf + cSf-CD4 | $1.8x10^{7}$ | 3.25 | 5.45% | $9.8x10^{5}$ |
| 5 | M | Sf + WT-CD4 | $7.0x10^{6}$ | 3.31 | 11.20% | $7.8x10^{5}$ |
| 6 | M | **WT + PBS** | - | - | - | - |
| 7 | F | Sf + Sf-CD4 | $1.3x10^{7}$ | 7.05 | 16.10% | $2.1x10^{6}$ |
| 8 | M | Sf + Sf-CD4 | $1.3x10^{7}$ | 7.05 | 16.10% | $2.1x10^{6}$ |
| 9 | M | Sf + WT-CD4 | $1.3x10^{7}$ | 5.56 | 10.10% | $1.3x10^{6}$ |
| 10 | F | Sf +WT-CD4 | $1.3x10^{7}$ | 5.56 | 10.10% | $1.3x10^{6}$ |
| 11 | F | Sf +WT-CD4 | $1.3x10^{7}$ | 5.56 | 10.10% | $1.3x10^{6}$ |
| 12 | F | Sf +Sf-CD4 | $1.3x10^{7}$ | 7.05 | 16.10% | $2.1x10^{6}$ |
| 13 | F | Sf +PBS | - | - | - | - |
| 14 | M | Sf +Sf-CD4 | $1.3x10^{7}$ | 7.05 | 16.10% | $2.1x10^{6}$ |
| 15 | M | Sf +PBS | - | - | - | - |
| 16 | M | Sf +PBS | - | - | - | - |
| 17 | M | **WT +PBS** | - | - | - | - |
| 18 | M | **WT + PBS** | - | - | - | - |
| 19 | F | Sf + cSf-CD4 | $2.5x10^{7}$ | 5.8 | 5.6% | $1.4x10^{6}$ |
| 20 | M | Sf + cSf-CD4 | $2.5x10^{7}$ | 5.8 | 5.6% | $1.4x10^{6}$ |
| 21 | M | Sf + PBS | - | - | - | - |
| 22 | F | Sf + PBS | - | - | - | - |

*Fig. 16*

B.
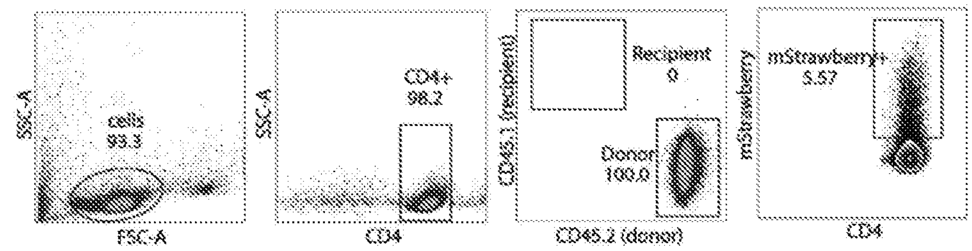
C.
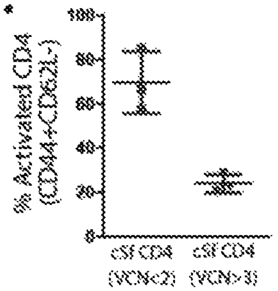
D.
cSf-CD4 with VCN<2
| Mouse | Sex | Arm | CD4 cell dose | CD4 VCN | % mStrawberry+ of total CD4 | Putative Treg Dose |
|---|---|---|---|---|---|---|
| F1 | M | Sf + cSf-CD4 | $2.60x10^7$ | 1.4 | 2.69% | $7x10^5$ |
| F1 | M | Sf + cSf-CD4 | $2.60x10^7$ | 1.4 | 2.69% | $7x10^5$ |
| F3 | M | Sf + cSf-CD4 | $4.0x10^7$ | 1.78 | 2.76% | $1.1x10^6$ |
*Fig. 16, cont'd.*

A.

NSG experiment #1
Female (XX) cord blood CD34+

| CPG site | #42 | #41 | #40 | #39 | #38 | #37 | #36 | #35 | #34 |
|---|---|---|---|---|---|---|---|---|---|
| | **Endogenous CNS2 (absolute methylation)** | | | | | | | | |
| **Treg** | 94.1 | 64.6 | 65.8 | 54.1 | 64.0 | 60.1 | 56.2 | 55.0 | 53.5 |
| **Tconv** | 100.0 | 100.0 | 100.0 | 86.9 | 97.3 | 95.7 | 83.7 | 77.5 | 82.5 |
| | **Endogenous CNS2 (Normalized for 2X chromosomes (x-50)/50 )** | | | | | | | | |
| **Treg** | 88.3 | 29.2 | 31.7 | 8.1 | 28.1 | 20.2 | 12.4 | 9.9 | 7.0 |
| **Tconv** | 100.0 | 100.0 | 100.0 | 73.9 | 94.6 | 91.4 | 67.4 | 54.9 | 65.1 |
| | **Viral CNS2 (absolute methylation)** | | | | | | | | |
| **Treg** | 10.5 | 3.1 | 3.8 | 0.0 | 3.5 | 0.0 | 0.0 | 0.0 | 0.0 |
| **Tconv** | 15.1 | 4.6 | 6.8 | 3.7 | 5.9 | 5.2 | 0.0 | 3.3 | 0.0 |

NSG experiment #2
Female (XX) cord blood CD34+

| CPG site | #42 | #41 | #40 | #39 | #38 | #37 | #36 | #35 | #34 |
|---|---|---|---|---|---|---|---|---|---|
| | **Endogenous CNS2 (absolute methylation)** | | | | | | | | |
| **Treg** | 100.0 | 95.8 | 85.4 | 73.6 | 88.0 | 88.5 | 74.3 | 62.8 | 79.4 |
| **Tconv** | 100.0 | 98.9 | 99.2 | 84.1 | 95.1 | 91.1 | 78.9 | 75.0 | 86.1 |
| | **Endogenous CNS2 (Normalized for 2X chromosomes (x-50)/50 )** | | | | | | | | |
| **Treg** | 100.0 | 91.6 | 70.9 | 47.1 | 76.0 | 77.0 | 48.6 | 25.7 | 58.8 |
| **Tconv** | 100.0 | 97.7 | 98.3 | 68.1 | 90.1 | 82.3 | 57.8 | 50.1 | 72.2 |
| | **Viral CNS2 (absolute methylation)** | | | | | | | | |
| **Treg** | 11.9 | 3.1 | 5.7 | 0.0 | 3.5 | 0.0 | 0.0 | 0.0 | 0.0 |
| **Tconv** | 12.3 | 2.8 | 5.4 | 0.0 | 3.7 | 3.3 | 0.0 | 0.0 | 0.0 |

*Fig. 18*

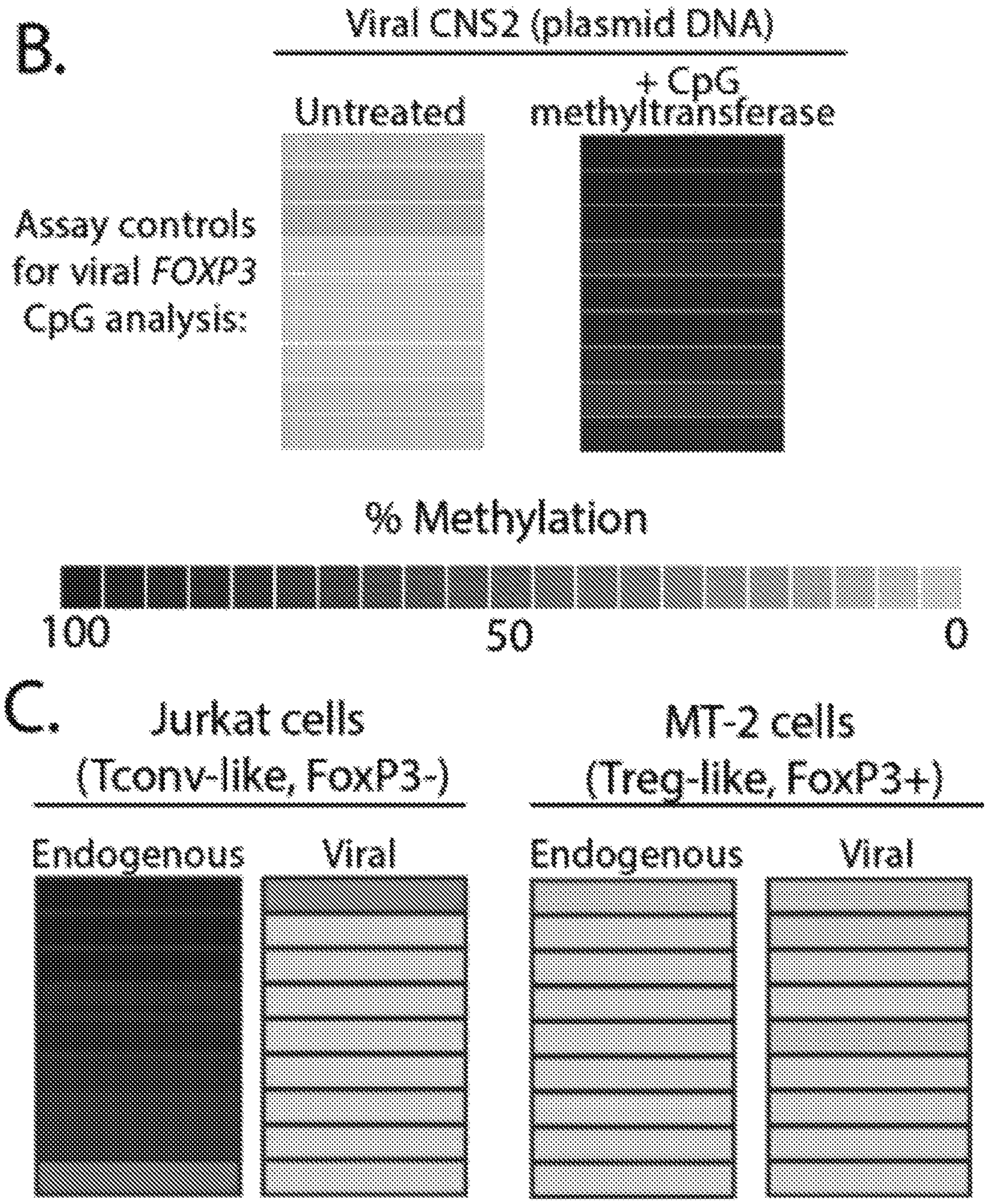
*Fig. 18, cont'd.*

SELF-INACTIVATING LENTIVIRAL VECTOR COMPRISING A FOXP3 EXPRESSION CASSETTE

CROSS-REFERENCE TO RELATED APPLICATIONS

This application is a Continuation of U.S. application Ser. No. 16/640,306 filed Feb. 19, 2020 and published as United States Publication No. 2020/0347404 on Nov. 5, 2020, which filed as a National Phase Application of PCT International Application No. PCT/US2018/047586, International Filing Date Aug. 22, 2018, which claims benefit of, and priority to U.S. Provisional Application No. 62/548,891, filed on Aug. 22, 2017, which are all incorporated in their entirety herein by reference.

SEQUENCE LISTING STATEMENT

The instant application contains a Sequence Listing which has been submitted electronically in ST.26 .XML format and is hereby incorporated by reference in its entirety. The .XML formatted sequence listing was created on Jun. 16, 2024, is named P-633483-US_SQL_16JUN24.xml and is 25.4 Kilobytes in size.

FIELD OF THE INVENTION

The disclosure relates in general to the field of lentiviral vectors for expression of a heterologous nucleic acid using the endogenous gene elements to regulate physiologic gene expression.

BACKGROUND

Patients with congenital absence of FoxP3 gene function (through inherited mutations) may be treated with allogeneic hematopoietic stem cell transplantation (HSCT) to provide a source of normal stem cells to produce normal populations of the immune effector cells with the needed FoxP3 gene function. However, allogeneic HSCT is limited by the need for a well-matched donor and risks for graft rejection or graft versus host disease due to immunological disparities between donor and recipient.

Autologous transplantation of gene corrected HSC would avoid these immune complications and allows far more effective HSCT to be performed. Autologous T cells from patients may be modified with vectors expressing this factor (FoxP3) with constitutive promoters, but these T cells have a finite life-span in vivo and the effect may wane with time.

Immune suppressive drugs of many types (corticosteroids, calcineurin inhibitors, anti-metabolite nucleoside, etc., may suppress some of the complications of inherited or acquired auto-immune/auto-inflammatory diseases, but may be only partially or minimally effective and have significant toxicities.

SUMMARY

Various embodiments contemplated herein may include, but need not be limited to, one or more of the following:

Embodiment 1: A recombinant lentiviral vector (LV) comprising:

- an expression cassette comprising a nucleic acid construct comprising a nucleotide sequence encoding a human FoxP3 protein operably linked to an endogenous FoxP3 promoter;

- where said LV is a TAT-independent and self-inactivating (SIN) lentiviral vector.

Embodiment 2: The vector of embodiment 1, wherein said a nucleotide sequence encoding a human FoxP3 protein comprises a FoxP3 cDNA.

Embodiment 3: The vector according to any one of embodiments 1-2, wherein said nucleotide sequence encoding a human FoxP3 is codon optimized.

Embodiment 4: The vector according to any one of embodiments 1-3, wherein said nucleotide sequence encoding a human FoxP3 protein is operably linked to one or more FoxP3 enhancer elements.

Embodiment 5: The vector of embodiment 4, wherein said enhancer elements are selected from the group consisting of Foxp3 conserved non-coding sequence 1 (FoxP3-CNS1), Foxp3 conserved non-coding sequence 2 (FoxP3-CNS2), and Foxp3 conserved non-coding sequence 3 (FoxP3-CNS3).

Embodiment 6: The vector of embodiment 5, wherein said expression cassette comprises FoxP3-CNS1, FoxP3-CNS2, and FoxP3-CNS3.

Embodiment 7: The vector according to any one of embodiments 1-6, wherein said vector comprises a FoxP3 3'UTR.

Embodiment 8: The vector according to any one of embodiments 1-7, wherein said vector comprises a ψ region vector genome packaging signal.

Embodiment 9: The vector according to any one of embodiments 1-8, wherein the 5' LTR comprises a CMV enhancer/promoter.

Embodiment 10: The vector according to any one of embodiments 1-9, wherein said vector comprises a Rev Responsive Element (RRE).

Embodiment 11: The vector according to any one of embodiments 1-10, wherein said vector comprises a central polypurine tract.

Embodiment 12: The vector according to any one of embodiments 1-11, wherein said vector comprises an insulator element.

Embodiment 13: The vector of embodiment 12, wherein said vector comprises an A2 insulator.

Embodiment 14: The vector of embodiment 13, wherein said vector comprises an A2 insulator within a U3 region.

Embodiment 15: The vector according to any one of embodiments 1-14, wherein said vector is incapable of reconstituting a wild-type lentivirus through recombination.

Embodiment 16: The vector according to any one of embodiments 1-15, wherein said vector comprises a PCCL backbone.

Embodiment 17: The vector according to any one of embodiments 1-16, wherein cells transfected with said vector recapitulate normal physiologic expression of FoxP3 in the appropriate mature lymphocyte.

Embodiment 18: The vector of embodiment 1, wherein said vector comprises the nucleic acid of SEQ ID NO:1.

Embodiment 19: A packaging cell transfected with a vector according to any one of embodiments 1-18.

Embodiment 20: A lentiviral particle encoded by a vector according to any one of embodiments 1-18.

Embodiment 21: A host cell infected with lentiviral particle encoded by a lentiviral vector according to any one of embodiments 1-18.

Embodiment 22: The host cell of embodiment 21, wherein said cell is a stem cell.

Embodiment 23: The host cell of embodiment 21, wherein said cell is a stem cell derived from bone marrow.

Embodiment 24: The host cell of embodiment 21, wherein said cell is a stem cell derived from cord blood.

Embodiment 25: The host cell of embodiment 21, wherein said cell is a peripheral blood stem cell.

Embodiment 26: The host cell of embodiment 21, wherein said cell is a human hematopoietic progenitor cell.

Embodiment 27: The host cell of embodiment 21, wherein said human hematopoietic progenitor cell is a $CD34^+$ cell.

Embodiment 28: The host cell of embodiment 27, wherein said human hematopoietic progenitor cell is a $CD34^+CD38^-$ cell.

Embodiment 29: An infectious lentivirus particle comprising a nucleic acid that expresses a human FoxP3 protein.

Embodiment 30: The lentivirus particle of embodiment 29, wherein said virus particle is produced using a lentiviral vector according to any one of embodiments 1-18.

Embodiment 31: A method of restoring regulatory T cell (Treg) function in a mammal with deficient FoxP3 expression, said method comprising:

- transducing a stem cell and/or progenitor cell from said subject with a lentiviral vector according to any one of embodiments 1-18 and/or a virus particle according to any one of embodiments 29-30; and
- transplanting said transduced cell or cells derived therefrom into said subject where said cells or derivatives therefrom express said human FoxP3 gene and restore regulatory T cell (Treg) function in said mammal.

Embodiment 32: A method of treating an autoimmune disorder in a subject, said method comprising, said method comprising: transducing a stem cell and/or progenitor cell from said subject with a lentiviral vector according to any one of embodiments 1-18 and/or a virus particle according to any one of embodiments 29-30; and transplanting said transduced cell or cells derived therefrom into said subject where said cells or derivatives therefrom express said human FoxP3 gene and ameliorate one or more symptoms of said autoimmune disorder and/or eliminate said autoimmune disorder.

Embodiment 33: The method of embodiment 32, wherein said autoimmune disorder comprises a disorder selected from the group consisting of myasthenia gravis, multiple sclerosis, Immune dysregulation, Polyendocrinopathy Enteropathy X-linked (IPEX), and autoimmune arthritis.

Embodiment 34: The method according to any one of embodiments 30-33, wherein said cells or derivatives therefrom recapitulate normal physiologic expression of FoxP3.

Embodiment 35: The method according to any one of embodiments 30-34, wherein the cell is a stem cell.

Embodiment 36: The method according to any one of embodiments 30-34, wherein said cell is a stem cell derived from bone marrow.

Embodiment 37: The method according to any one of embodiments 30-34, wherein said cell is a stem cell derived from cord blood.

Embodiment 38: The method according to any one of embodiments 30-34, wherein said cell is peripheral blood stem cell.

Embodiment 39: The method according to any one of embodiments 30-34, wherein, wherein the cell is a human hematopoietic progenitor cell.

Embodiment 40: The method of embodiment 39, wherein the human hematopoietic progenitor cell is a $CD34^+$ cell.

Embodiment 41: The method of embodiment 40, wherein the human hematopoietic progenitor cell is a $CD34^+$/$CD38^{-\ cell.}$

BRIEF DESCRIPTION OF THE DRAWINGS

FIG. 8, panels A-F, shows that constitutive FoxP3 expression impairs HSPC engraftment Panel A) Viability and GFP expression in murine lin− HSPC transduced with control LV (MNDU3-GFP) or constitutive FoxP3 LV (MNDU3-FoxP3−IRES-GFP) at 3 days post transduction. Panel B) Peripheral blood engraftment of donor (CD45.1) lin− HSPC transduced with control LV (MNDU3-GFP) or constitutive FoxP3 LV (MNDU3-FoxP3−IRES-GFP) at 7 days post-transplant. FACS plots show donor (CD45.1) engraftment and GFP expression in donor cells (n=10 mice/group). Panel C) White blood cell (WBC), red blood cell (RBC) and platelet counts in transplanted mice at 10 days and 21 days post-transplant (n=10 mice per group). Panel D) Survival of mice after transplant. N=10 mice per group. Panel E) Viability and GFP expression in CB CD34+ HSPC transduced with control LV (MNDU3-GFP) or constitutive FoxP3 LV (MNDU3-FoxP3−IRES-GFP) at 3 days post transduction. Panel F) Peripheral blood engraftment of hCD45+ cells (expressed as a percentage of total hCD45++ mCD45+) in humanized NSG mice at 6-8 weeks post-transplant. Data represent mice humanized with CB CD34+ cells from 12 independent donors, n=16-17 mice per group. Students t-test. Data represent mean±SD for panel B, mean±SEM for panel C, and median±IQR and range for panel F. Data in panels C and F are analyzed using Student's t-test. Data in (D) are analyzed using log-rank (Mantel-Cox) test. *p<0.05, p<0.01, *p<0.001.

FIG. 9A: Endogenous human FOXP3 gene shows location of regulatory regions (Promoter, CNS1, CNS2, CNS3, and 3' UTR) included in vector. FIG. 9B: Vector maps show design of CNS123p−mStrawberry and CNS123p-FoxP3−mStrawberry constructs within the pCCL vector backbone. CNS123p−mStrawberry drives expression of mStrawberry. CNS123p-FoxP3−mStrawberry drives expression of FoxP3 cDNA P2A-linked to mStrawberry.

Figure 12:
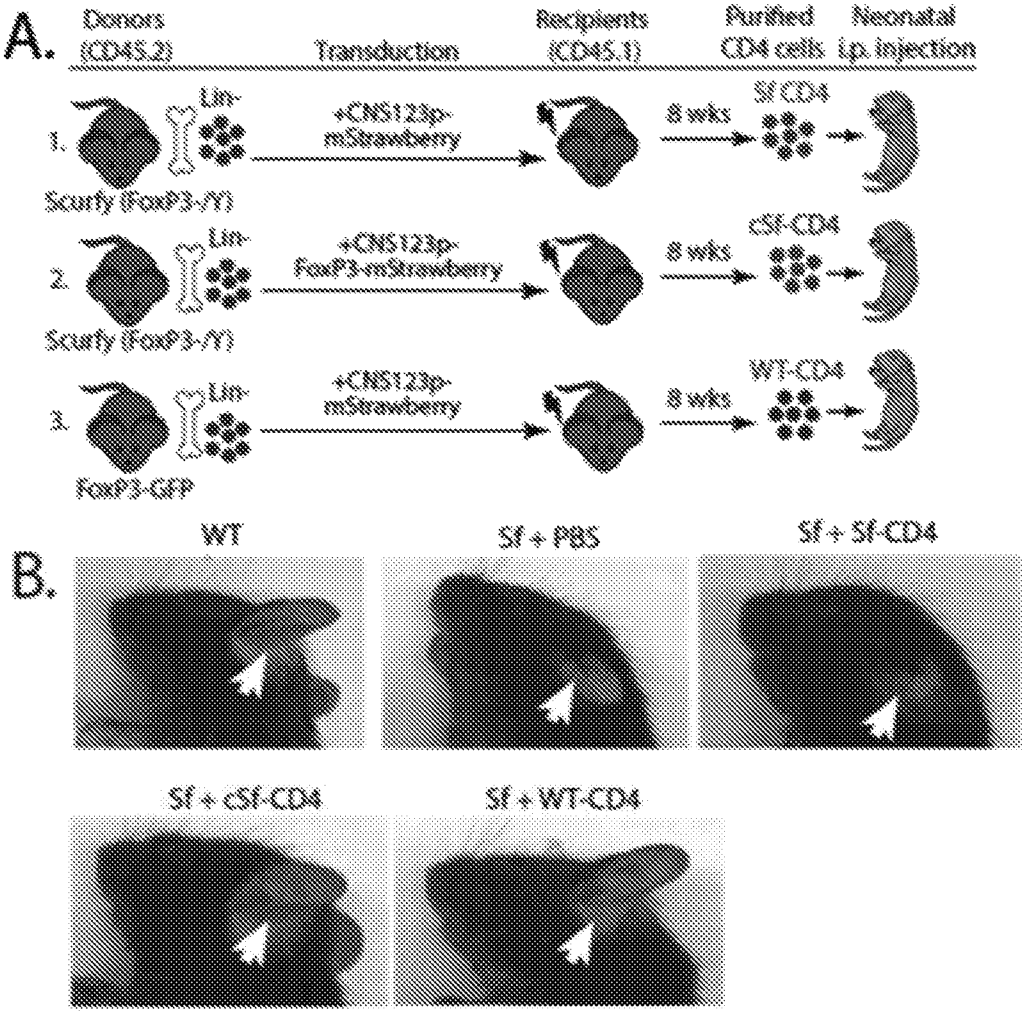

FIG. 12, panels A-E. The lineage-specific FoxP3 cDNA vector generates functional Tregs capable of rescuing the scurfy mouse. Panel A) Experimental set up. Scurfy or WT HSPC (CD45.2) were transduced with either CNS123p−mStrawberry or CNS123p-FoxP3−mStrawberry and transplanted into lethally irradiated congenic (CD45.1) recipients. 8 weeks post-transplant, donor CD45.2+CD4+ cells (containing putative Tregs) were purified from the spleens of transplant recipients, and injected intraperitoneally into scurfy neonates. Rescue of scurfy neonates was evaluated 21 days after transfer of CD4 T cells. Panel B) Photographs of rescued scurfy mice at 21 d. White arrows highlight correction of car skin inflammation in Scurfy mouse recipients of cSf-Tregs and WT-Tregs, but not Sf-Tregs. Panel C) Spleen to body weight ratio for rescued scurfy mice or WT littermate controls (n=3 independent experiments, 3-6 mice/arm). Panel D) Percentage of activated (CD44+CD62L−) CD4 T cells in the spleens of rescued scurfy mice or WT littermate controls. Panel E) Scrum cytokine levels in rescued scurfy mice or WT littermate controls. Data in panels C-E are presented as mean±SD. Data in panels C, D, and E were analyzed by Kruskal-Wallis test for overall comparison for all groups, and Mann-Whitney U test was performed for pairwise comparisons. *$p<0.05$, **$p<0.01$, NS, not significant.

Figure 13:
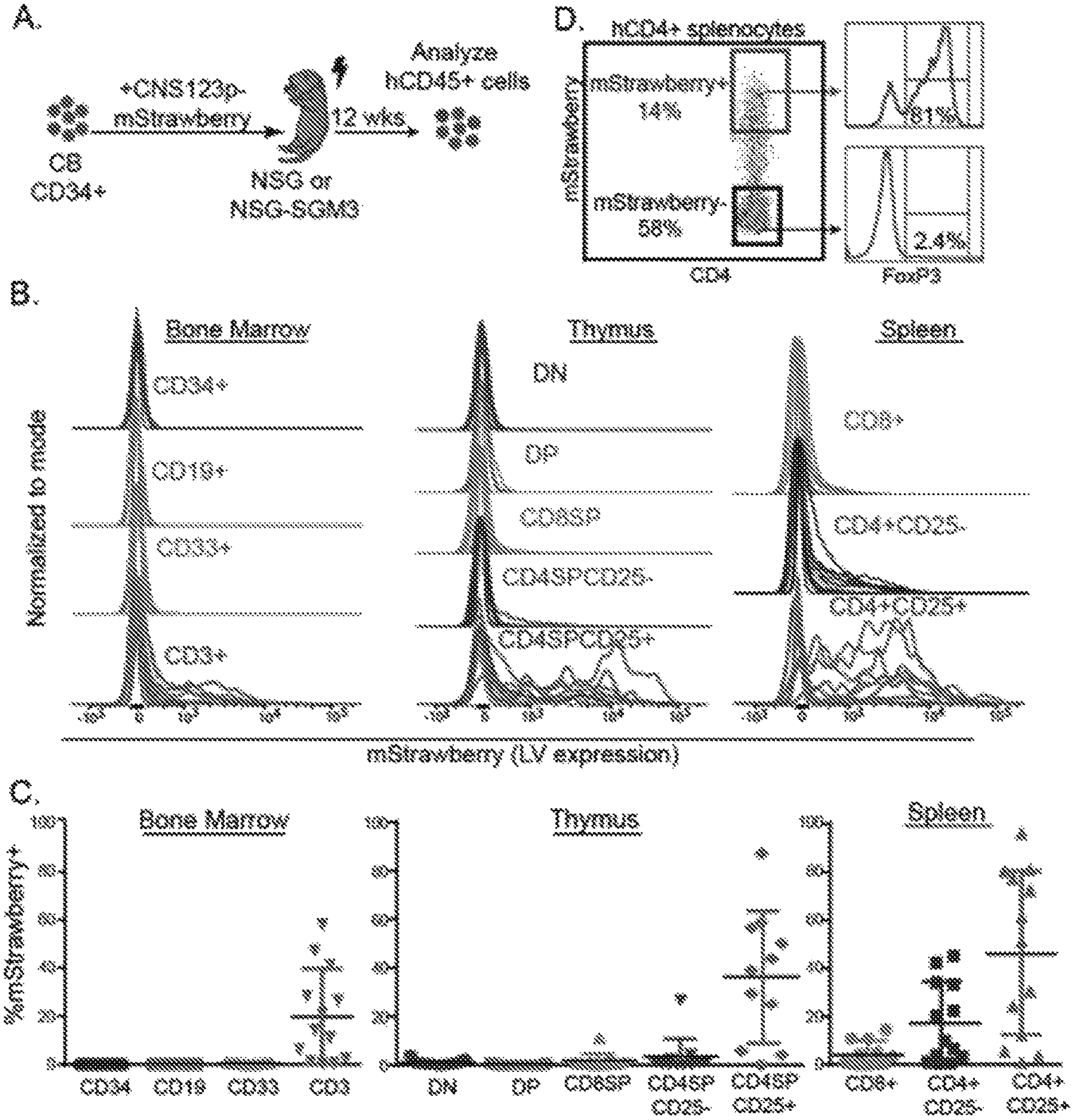

FIG. 13, panels A-F. The FoxP3 reporter vector shows Treg lineage specific expression in a humanized mouse model. Panel A) Experimental set up for humanized mouse models. CD34+ HSPC (from normal human cord blood) were transduced with CNS123p−mStrawberry and transplanted into neonatal NSG mice (Panels B, C, E, F) or NSG-SGM3 mice (Panel D). 12-16 weeks post-transplant, engrafted hCD45+ cells were analyzed for mStrawberry expression. Panel B) MStrawberry reporter expression in each hematopoietic lineage. Lineages analyzed include bone marrow CD34+ stem and progenitor cells, CD19+ B cells, CD33+ myeloid cells, and CD3+ T cells, thymic CD4−CD8− double negative (DN), CD4+CD8+ double positive (DP), CD4−CD8+ single positive (CD8 SP), CD4+CD8−CD25− (CD4 Tconv cells), and CD4+CD8−CD25+ (Treg) and splenic CD8 T cells, CD4+CD25− Tconv cells, and CD4+CD25+ Treg cells. Each overlaid histogram represents lineage-defined mStrawberry expression in an individual mouse (n=10-14 mice humanized with 2 different cord blood CD34+ donors). Panel C) Percentage of mStrawberry+ cells in each lineage shown in panel B. Panel D) Co-expression of FoxP3 and mStrawberry in humanized mice. Human CD4+ cells were enriched from 2 pooled spleens of engrafted NSG-SGM3 mice. CD4+ cells were FACS sorted into mStrawberry+ and mStrawberry− populations followed by intracellular staining for FoxP3 expression. FACS sorting was performed prior FoxP3 analysis due to quenching of mStrawberry fluorescence during the FoxP3 intracellular staining protocol. Left panel shows sorting of human CD4+ cells by mStrawberry expression, while right panel shows FoxP3 expression in sorted populations. Results are representative of 2 independent experiments. Panel E) Experimental set up for NSG competitive repopulation assay. "Test" CB CD34+ cells were transduced with either CNS123p−mStrawberry or CNS123p-FoxP3−mStrawberry while "competitor" CD34+ cells were transduced with a UBC-mCitrine vector. Test and competitor cells were co-transplanted at a 1:1 ratio into NSG neonates and the percentage of competitor (mCitrine+) CD34+ cells engrafted in the BM at 12 weeks was determined for each group (n=6 mice per group, humanized from 2 different CB CD34+ donors). Panel F) CNS2 methylation analysis of T cell populations from humanized mice. Drawing depicts the location of CNS2 within the endogenous FOXP3 gene and CNS2 within the viral genome. Red arrows indicate differential primer binding sites for amplification of endogenous or viral CNS2 regions. Enlarged area of CNS2 depicts 9 CpG sites analyzed for methylation status by bisulfite sequencing. FACS plot shows sorting gates used to define Treg (CD4+CD25+) and Tconv (CD4+CD25−) populations in CD4 enriched cells isolated from the pooled spleens of 3-5 humanized mice. Heat map represents the percentage of methylated reads detected at each of the 9 CpG sites within endogenous and viral CNS2. Results are representative of 2 independent experiments using pooled NSG cohorts humanized from 2 different CB CD34+ donors (FIG. 18). Data in panel E represent mean±SD. Data in panel E were analyzed by Mann-Whitney U test, NS, not significant.

Figure 14:
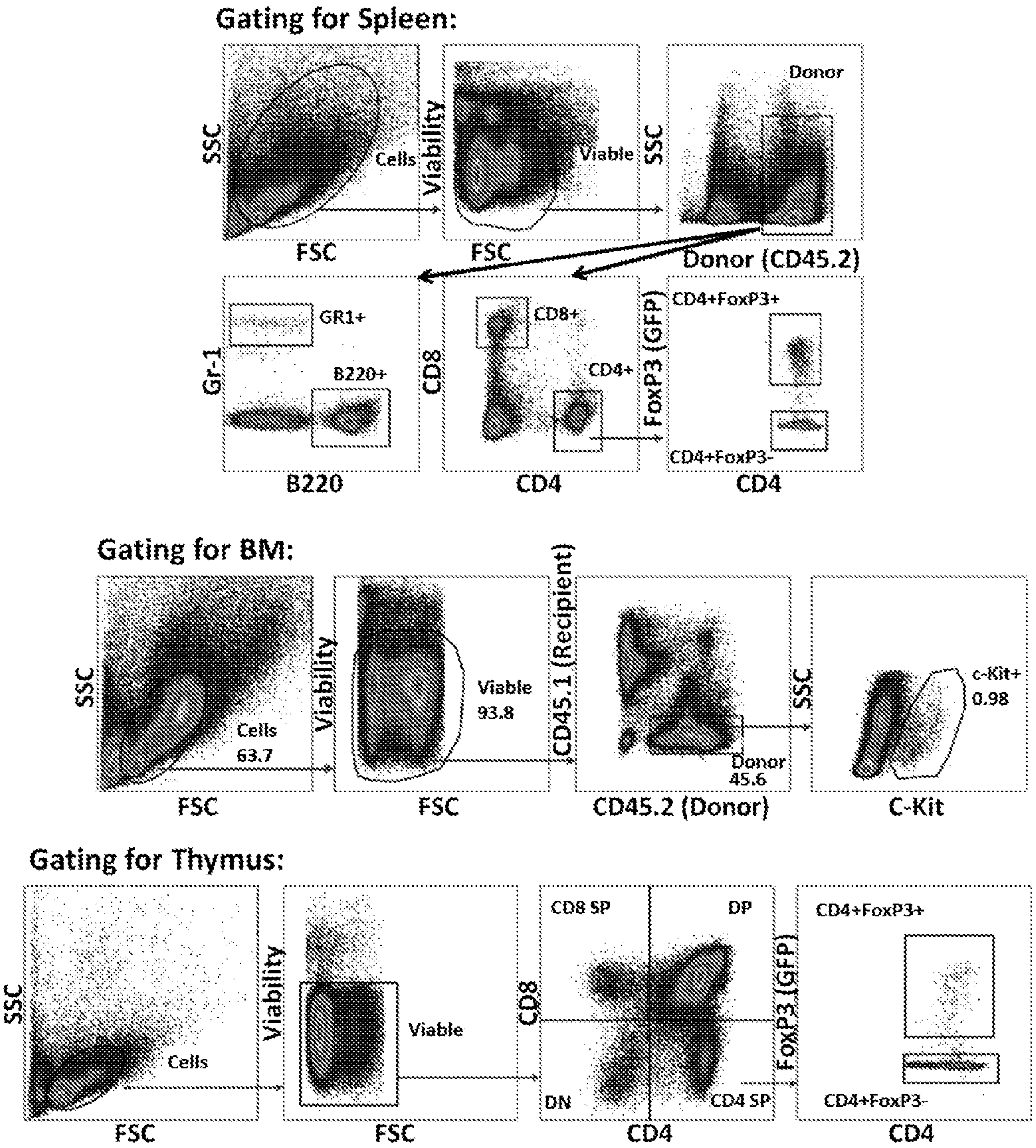

FIG. 14. (Corresponding to FIG. 10): Flow cytometric definition of murine hematopoietic lineages Gating is shown for each defined population in the spleen (Gr1+, B220+, CD8+, CD4+FoxP3−, CD4+FoxP3+), Bone marrow (cKit+), and Thymus (DN, DP, CD8 SP, CD4+FoxP3−, CD4+FoxP3+).

Figure 15:
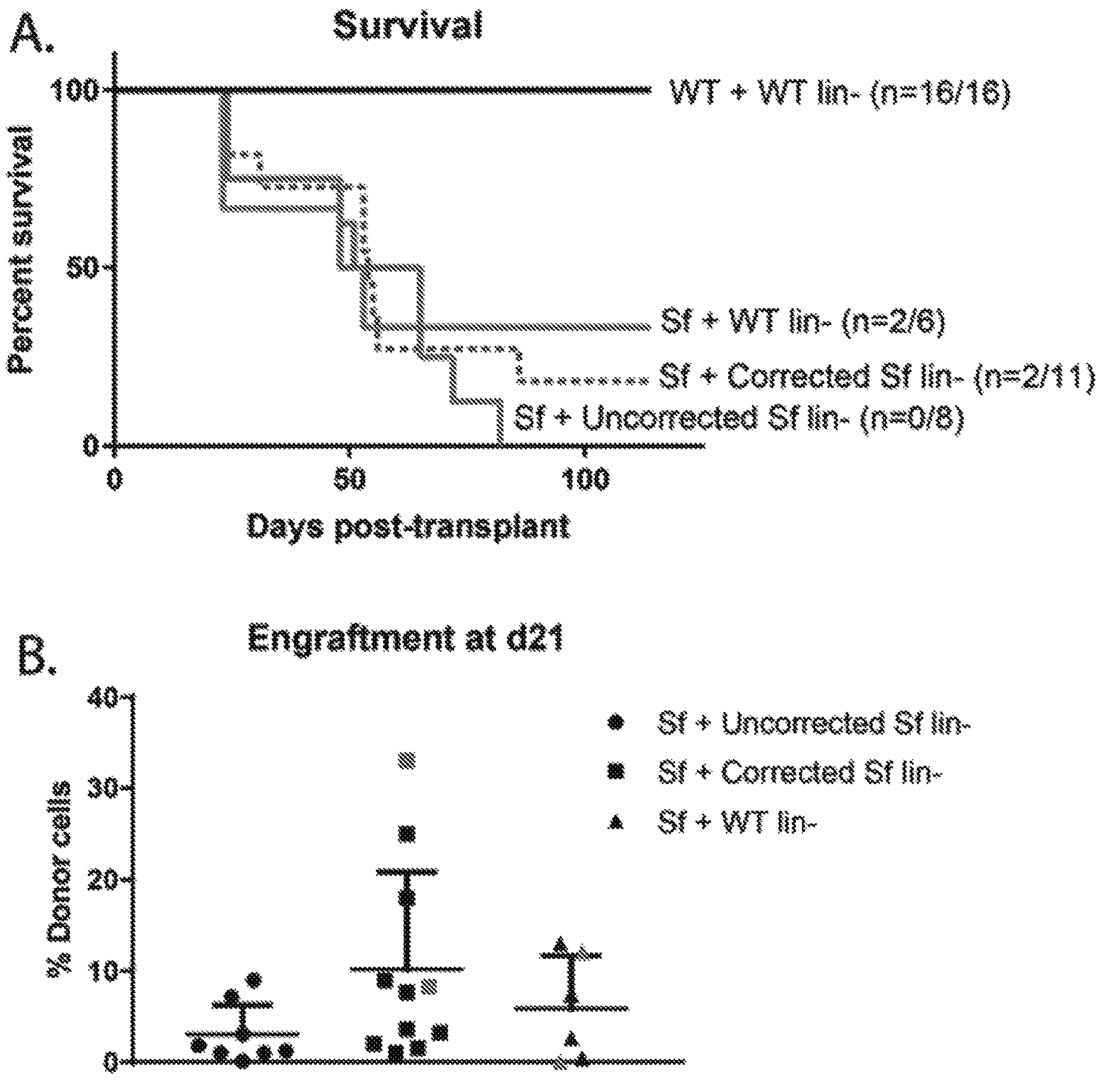

FIG. 15, panels A and B. HSC transplant of scurfy neonates. Panel A) Survival curve after HSC transplant with lin− cells. Scurfy or WT neonates (d0-d1) were irradiated with 500 Rad followed by intrahepatic injection of LV-modified lin− cells. Each pup received the total lin− cell dose purified from the femurs and tibia of 1 donor mouse (range 1E6-6E6 lin− cell/mouse). WT lin− cells and uncorrected scurfy lin− cells were transduced with the CNS123p-mStrawberry reporter LV while corrected scurfy lin− cells were transduced with the CNS123p-FoxP3-mStrawberry LV. Results represent pooled data from 9 transplanted litters (containing Scurfy and WT littermates) with 6-16 total mice per treatment group. Non surviving mice are mice that spontaneously died or were euthanized due to a moribund state as determined by a veterinarian blinded to the treatment groups. Panel B) 21 day peripheral blood engraftment in scurfy neonates receiving lin− cells. Percentages represent CD45.2+ donor cells as a percentage of total CD45+ (CD45.2 and CD45.1/CD45.2) cells. Symbols marked in red represent engraftment in mice surviving to the end of the study (114 days).

FIG. 16, panels A-D. (Corresponding to FIG. 12): Panel A) Characteristics of CD4 purified cell product for adoptive transfer. "Arm" defines genotype of recipient neonate (Scurfy [Sf] or Wild-type [WT])+cell product injected (PBS=sham PBS injection, Sf-CD4=uncorrected Scurfy CD4, cSf-CD4=corrected scurfy CD4, WT-CD4=Wild-type CD4). Panel B) Representative FACS analysis of magnetic bead purified CD4+ cells prior to adoptive transfer. Plots show high purity of CD4+ cells with absence of contaminating recipient CD45.1+ cells. Panel C) Comparison of activated splenic CD4 cells in failed scurfy rescues (cSf-CD4 VCN<2) and successful scurfy rescues (cSf-CD4>3). Panel D) Characteristics of cSf-CD4 products (with VCN <2) which failed to suppress CD4 activation (CD44+ CD62L−) in spleens of recipient mice.

Figure 17:
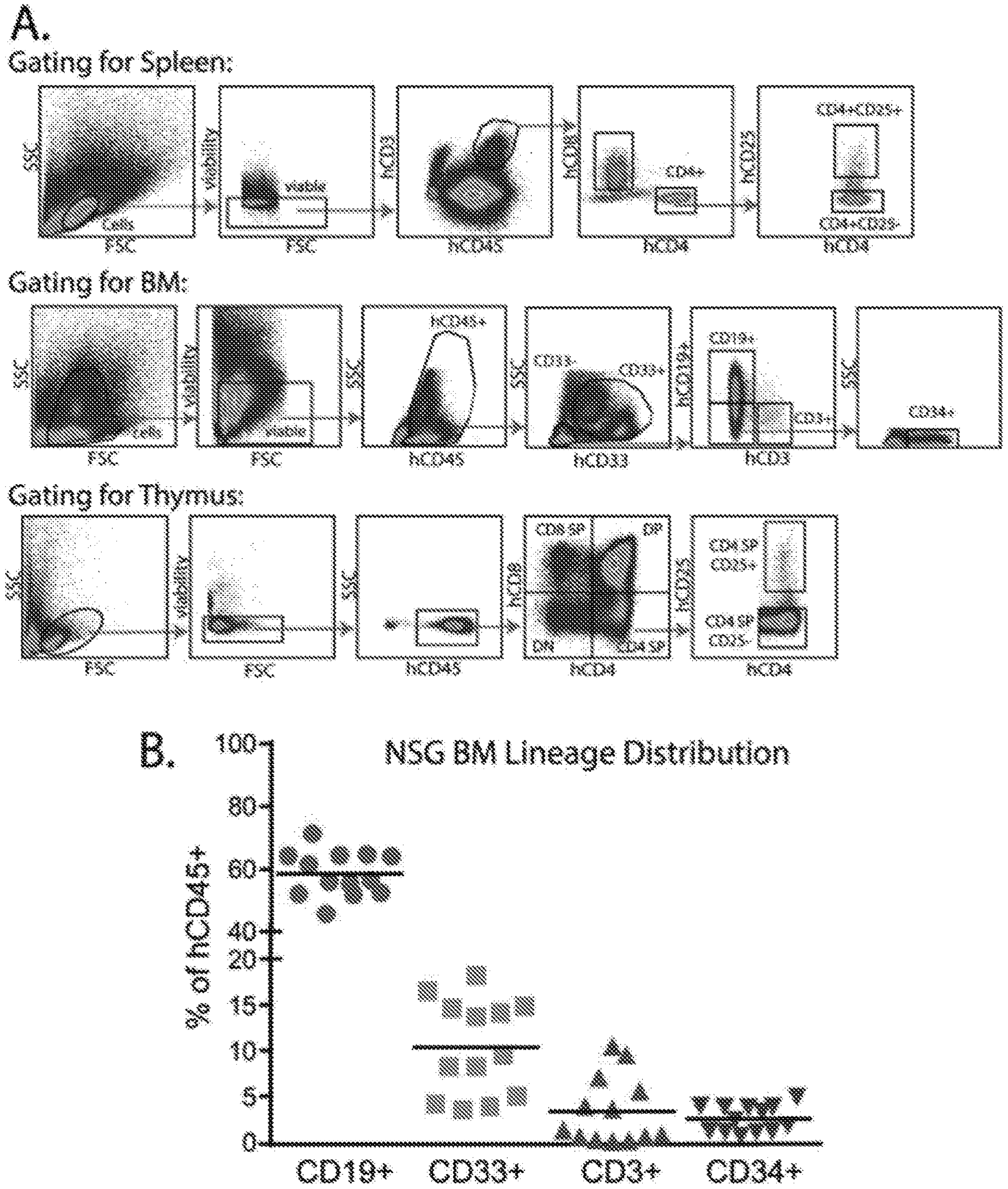

FIG. 17, panels A and B. Corresponding to FIG. 13): Flow cytometric characterization of human hematopoietic lineages in humanized NSG mice. Panel A) Gating is shown for each defined population in the spleen (CD8+, CD4+CD25−, D4+CD25+), Bone marrow (CD33+, CD19+, CD3+, CD34+), and Thymus (DN, DP, CD8 SP, CD4+CD25−, CD4+CD25+). Panel B) Lineage distribution of engrafted human cells in NSG bone marrow. Percentages represent the relative contribution of each lineage as a percentage of total hCD45+ cells. n=13 mice pooled from 2 independent experiments FIG. 18, panels A-C. (Corresponding to FIG. 13): Methylation Analysis of endogenous and Viral CNS2. Panel A) Percentage of methylated reads at 9 CpG sites within FoxP3 CNS2 are shown for Treg and Tconv cells sorted from NSG mice humanized with FoxP3 LV-modified CD34+ cells. Values are shown for 2 independent experiments using female cord blood CD34+ cells. Top row shows the absolute number of methylated reads for endogenous CNS2. Middle row shows normalized reads for endogenous CNS2 which accounts for a baseline 50% methylation of 2× chromosomes. Bottom row shows percentage of methylated reads in viral CNS2. Panel B) Assay controls for FoxP3 CNS2 methylation analysis. Plasmid DNA encoding the FoxP3 cDNA LV genome was treated with CpG methyltransferase as a positive control while untreated cDNA LV plasmid was used as a negative control. Samples were analyzed for CpG methylation using pyrosequencing primers for the viral CNS2 site. Controls demonstrate the capacity of the pyrosequencing methylation assay to detect a full range of methylation at each CpG site with viral CNS2 primers. Panel C) Methylation analysis of endogenous and viral FoxP3 CNS2 in Jurkat and MT2 cells transduced with the FoxP3 cDNA vector.

DETAILED DESCRIPTION

In various embodiments, lentiviral vectors expressing FoxP3 using the endogenous gene elements to regulate physiologic gene expression of FoxP3 are provided herein as well as uses of such vectors. In particular, in various embodiments, lentiviral vectors using the endogenous transcriptional control elements from the human FoxP3 gene per se to express codon-optimized FoxP3 gene or cDNA to treat genetic deficiencies of FoxP3 (e.g., IPEX disease) or to treat other auto-immune and auto-inflammatory conditions (e.g. inflammatory bowel disease, Type 1 diabetes mellitus, SLE, JRA, multiple sclerosis, etc.) are provided. These vectors can be used to introduce these sequences into autologous hematopoictic stem cells to recapitulate normal physiologic expression patterns of the FoxP3 gene product in the appropriate mature lymphocytes.

This approach is in contrast to gene transfer vectors that use non-specific enhancer/promoters to drive constitutive expression of these genes that could lead to ectopic expression in multiple blood cell types and lead to unwanted effects. The use of the endogenous transcriptional control elements leads to precise, accurate on-target expression of the genes to mimic normal patterns of expression. It is believed this results in significant therapeutic benefits various clinical settings, e.g., as described below.

FOXP3 (forkhead box P3), also known as scurfin, is a protein involved in immune system responses (Brunkow et al. (2001) *Nat. Genet.* 27(1): 68-73). A member of the FOX protein family, FOXP3 appears to function as a master regulator of the regulatory pathway in the development and function of regulatory T cells (see, e.g., Hori et al. (2003) *Science,* 299(5609): 1057-1061; Fontenot et al. (2003) *Nat. Immunol.,* 4(4): 330-336; Fontenot et al. (2005) *Immunity,* 22(3): 329-341). Regulatory T cells generally turn the immune response down. In autoimmune disease, a deficiency of regulatory T cell activity can allow other autoimmune cells to attack the body's own tissues (see, e.g., Josefowicz et al. (2012) *Ann. Rev. Immunol.* 30:531-564; Zhang et al. (2007) *J. Cell. Physiol.* 211(3): 590-597).

Regulatory T cells (Tregs) play a pivotal role in regulating immune responses and maintaining immunological tolerance. Treg adoptive transfer therapy is expected to provide a clinical cure for various immunological disorders (see, e.g., Sakaguchi et al. (2006) *Immunol. Rev.* 212:8-27; Sakaguchi et al. (2008) *Cell,* 133(5): 775-787; Liston and Gray (2014) *Nat. Rev. Immunol.* 14(3): 154-165). Tregs are mainly generated via two different routes. The first is through direct development from Treg progenitor cells in the thymus by thymic antigen presentation with high affinity. These Tregs are called naturally occurring Tregs (nTregs) or thymic Tregs (tTregs). The second is through differentiation from naïve CD4 T cells in the periphery by antigen presentation with transforming growth factor (TGF)-β. These Tregs are called induced Tregs in vitro (iTregs) or peripherally induced Tregs (pTregs) (see, e.g., Chen et al. (2003) *J. Exp. Med.* 198(12): 1875-1886; Josefowicz and Rudensky (2009) *Immunity,* 30(5): 616-625). Both Tregs have similar suppression activity and markedly express Forkhead box P3 (Foxp3), a master transcriptional factor for Tregs. Foxp3 expression is required for the differentiation and maintenance of Treg function by expressing Treg signature genes and suppressing effector T cell (Teff) genes (see, e.g., Bennett et al. (2001) *Nat. Genet.* 27(1): 20-21; Hori et al. (2003) *Science,* 299(5609): 1057-1061; Fontenot et al. (2003) *Nat. Immunol.* 4(4): 330-336; Bettelli et al. (2005)

*Proc. Natl. Acad. Sci. USA,* 102(14): 5138-5143; Ichiyama et al. (2008) *J. Biol. Chem.* 283(25): 17003-17008).

Decreased function of $T_{reg}$ cells has been associated with various autoimmune disorders in human and mice (Paust and Cantor (2005) *Immunol. Rev.* 204:195-207). Reduced level of Foxp3 expression correlated with impaired $T_{reg}$ function and was found in such autoimmune diseases as myasthenia gravis and multiple sclerosis (see, e.g., Huan et al. (2005) *J. Neurosci. Res.* 81:45-52; Balandina et al. (2005) *Blood,* 105:735-741). The most conspicuous deficiency of $T_{reg}$ function is observed in the human autoimmune disease IPEX (Immune dysregulation, Polyendocrinopathy, Enteropathy, X-linked) and the corresponding disease in scurfy mice (see, e.g., Levy-Lahad and Wildin (2001) *J. Pediatr.* 138:577-580; Godfrey et al. (1991) *Am. J. Pathol.* 138:1379-1387). Affected males suffer from fatal, multi-organ, lymphoproliferative disease mediated by $CD4^+$ T cells (see, e.g., Clark et al. (1999) *J. Immunol.* 162:2546-2554; Blair et al. (1994) *J. Immunol.* 153:3764-3774). Mutations in the Foxp3 gene affecting its function were found to be the molecular basis of IPEX and scurfy diseases.

In view of the foregoing, it is believed the lentiviral vectors expressing FoxP3 described herein can be effectively used to restore regulatory T cell (Treg) function in a mammal with deficient FoxP3 expression. Similarly, it is believed the lentiviral vectors expressing FoxP3 described herein can be effectively used to treating an autoimmune disorder in a subject. In certain embodiments the autoimmune disorders are autoimmune disorders characterized by diminished FoxP3 expression and/or FoxP3 mutations. Illustrative autoimmune disorders include, but are not limited to myasthenia gravis. multiple sclerosis, IPEX (Immune dysregulation, Polyendocrinopathy, Enteropathy, X-linked), autoimmune arthritis, and the like.

In general, the methods involve use of the lentiviral vectors described herein comprising a FoxP3 gene or cDNA under the control of an endogenous FoxP3 promoter (and in certain embodiments, FoxP3 enhancers, (e.g. CNS1, and/or CNS2, and/or CNS3), to introduce these sequences into autologous hematopoietic stem cells. The transduced cells are re-introduced into the subject where they recapitulate normal physiologic expression patterns of the FoxP3 gene product in the appropriate mature lymphocytes and thereby ameliorate and/or cure the disease.

Figure 6:
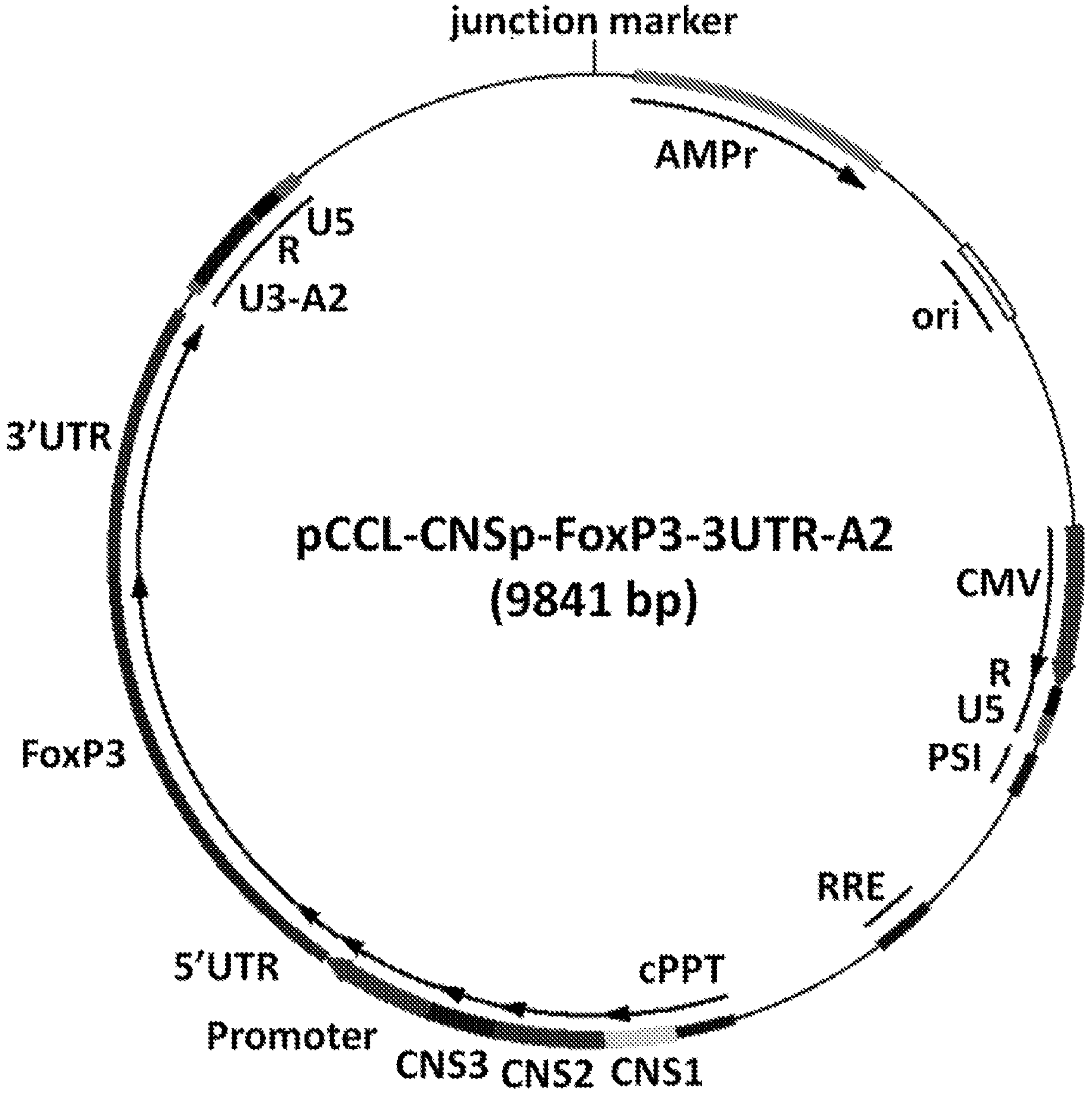
FIG. 6, illustrates the structure of the pCCL-CNSp-FOXP3−3UTR-A2 vector (SEQ ID NO: 1 (sequence from junction marker)). Sequences of human genomic origin: CNS1 (237 bp) Minimal sequence based (but not identical to sequence described by Tone et al. (2008) Smad3 and NFAT cooperate to induce Foxp3 expression through its enhancer. *Nature Immunology,* 9:194-202); CNS2 (359 bp) published by Kim and Leonard (2007) CREB/ATF-dependent T cell receptor-induced FoxP3 gene expression: a role for DNA methylation. *JEM,* 204:1543-1551; CNS3 (217 bp) published by Zheng et al. (2010) Role of conserved non-coding DNA elements in the Foxp3 gene in regulatory T-cell fate, *Nature* 473:808-813; Promoter (382 bp) sequence modified from Kim and Leonard (2007), supra.; 5'UTR (187 bp) based on human genomic NCBI reference sequence file NM_014009; FoxP3 cDNA (1292 bp) based on human genomic NCBI reference sequence file NM_01009; 3'UTR (875 bp) based on human genomic NCBI reference sequence file NM_014009.
Figure 7:
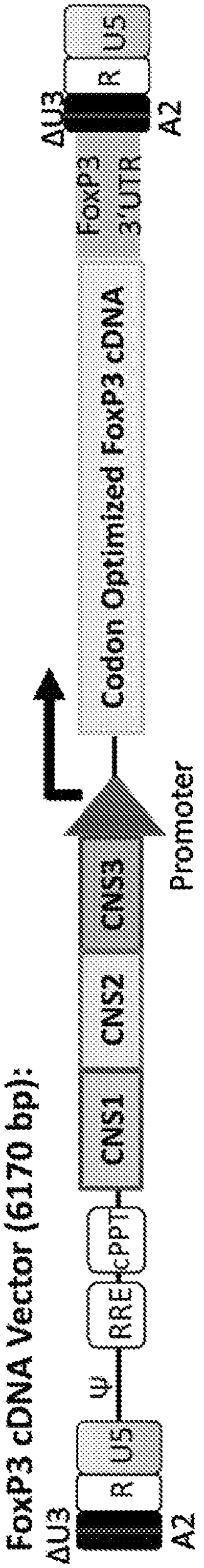
FIG. 7, illustrates components of a FoxP3 lentiviral vector.

In various embodiments recombinant lentiviral vector (LV) vectors are provided where the vectors comprise an expression cassette comprising a nucleic acid construct comprising a nucleotide sequence encoding a human FoxP3 protein operably linked to an endogenous FoxP3 promoter. In certain illustrative, but non-limiting embodiments the where said LV is a TAT-independent and self-inactivating (SIN) lentiviral vector. In certain embodiments the nucleotide sequence encoding a human FoxP3 protein comprises a FoxP3 cDNA. In certain embodiments the nucleotide sequence encoding a human FoxP3 protein is operably linked to one or more FoxP3 enhancer elements (e.g., FoxP3-CNS1, and/or FoxP3-CNS2, and/or FoxP3-CNS3). One illustrative, but non-limiting vector is shown in FIGS. 6 and 7, and in one embodiment the vector comprises the sequence shown in Table 1 (SEQ ID NO:1).

Also provided are packaging cells comprising the vectors described herein, and viral particles produced using the vectors described herein.

TAT-Independent and Self Inactivating Lentiviral Vectors

To further improve safety, in various embodiments, the LVs comprising a nucleic acid encoding a human FoxP3 protein under the control of an endogenous promoter, described herein comprise a TAT-independent, self-inactivating (SIN) configuration. Thus, in various embodiments it is desirable to employ in the LVs described herein an LTR region that has reduced promoter activity relative to wild-type LTR. Such constructs can be provided that are effectively "self-inactivating" (SIN) which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that that cellular coding sequences located adjacent to the vector integration site will be aberrantly expressed.

Furthermore, a SIN design reduces the possibility of interference between the LTR and the promoter that is driving the expression of the transgene. SIN LVs can often permit full activity of the internal promoter.

The SIN design increases the biosafety of the LVs. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

In certain embodiments self-inactivation is achieved through the introduction of a deletion in the U3 region of the 3' LTR of the vector DNA, i.e., the DNA used to produce the vector RNA. During RT, this deletion is transferred to the 5' LTR of the proviral DNA. Typically, it is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function typically spread out over U3, R and U5. Accordingly, in certain embodiments, it is desirable to eliminate as many of the transcriptionally important motifs from the LTR as possible while sparing the polyadenylation determinants.

The SIN design is described in detail in Zufferey et al. (1998) *J Virol.* 72(12): 9873-9880, and in U.S. Pat. No. 5,994,136. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3'LTR may decrease polyadenylation of vector transcripts with adverse consequences both on the titer of the vector in producer cells and the transgene expression in target cells.

Additional SIN designs are described in U.S. Patent Publication No: 2003/0039636. As described therein, in certain embodiments, the lentiviral sequences removed from the LTRs are replaced with comparable sequences from a non-lentiviral retrovirus, thereby forming hybrid LTRs. In particular, the lentiviral R region within the LTR can be replaced in whole or in part by the R region from a non-lentiviral retrovirus. In certain embodiments, the lentiviral TAR sequence, a sequence which interacts with TAT protein to enhance viral replication, is removed, preferably in whole, from the R region. The TAR sequence is then replaced with a comparable portion of the R region from a non-lentiviral retrovirus, thereby forming a hybrid R region. The LTRs can be further modified to remove and/or replace with non-lentiviral sequences all or a portion of the lentiviral U3 and U5 regions.

Accordingly, in certain embodiments, the SIN configuration provides a retroviral LTR comprising a hybrid lentiviral R region that lacks all or a portion of its TAR sequence, thereby eliminating any possible activation by TAT, wherein the TAR sequence or portion thereof is replaced by a comparable portion of the R region from a non-lentiviral retrovirus, thereby forming a hybrid R region. In a particular embodiment, the retroviral LTR comprises a hybrid R region, wherein the hybrid R region comprises a portion of the HIV R region (e.g., a portion comprising or consisting of the nucleotide sequence shown in SEQ ID NO: 10 in US 2003/0039636) lacking the TAR sequence, and a portion of the MoMSV R region (e.g., a portion comprising or consisting of the nucleotide sequence shown in SEQ ID NO: 9 in 2003/0039636) comparable to the TAR sequence lacking from the HIV R region. In another particular embodiment, the entire hybrid R region comprises or consists of the nucleotide sequence shown in SEQ ID NO: 11 in 2003/0039636.

Suitable lentiviruses from which the R region can be derived include, for example, HIV (HIV-1 and HIV-2), EIV, SIV and FIV. Suitable retroviruses from which non-lentiviral sequences can be derived include, for example, MoMSV, MoMLV, Friend, MSCV, RSV and Spumaviruses. In one illustrative embodiment, the lentivirus is HIV and the non-lentiviral retrovirus is MoMSV.

In another embodiment described in US 2003/0039636, the LTR comprising a hybrid R region is a left (5') LTR and further comprises a promoter sequence upstream from the hybrid R region. Preferred promoters are non-lentiviral in origin and include, for example, the U3 region from a non-lentiviral retrovirus (e.g., the MoMSV U3 region). In one particular embodiment, the U3 region comprises the nucleotide sequence shown in SEQ ID NO: 12 in US 2003/0039636. In another embodiment, the left (5') LTR further comprises a lentiviral U5 region downstream from the hybrid R region. In one embodiment, the U5 region is the HIV U5 region including the HIV att site necessary for genomic integration. In another embodiment, the U5 region comprises the nucleotide sequence shown in SEQ ID NO: 13 in US 2003/0039636. In yet another embodiment, the entire left (5') hybrid LTR comprises the nucleotide sequence shown in SEQ ID NO: 1 in US 2003/0039636.

In another illustrative embodiment, the LTR comprising a hybrid R region is a right (3') LTR and further comprises a modified (e.g., truncated) lentiviral U3 region upstream from the hybrid R region. The modified lentiviral U3 region can include the att sequence, but lack any sequences having promoter activity, thereby causing the vector to be SIN in that viral transcription cannot go beyond the first round of replication following chromosomal integration. In a particular embodiment, the modified lentiviral U3 region upstream from the hybrid R region consists of the 3' end of a lentiviral (e.g., HIV) U3 region up to and including the lentiviral U3 att site. In one embodiment, the U3 region comprises the nucleotide sequence shown in SEQ ID NO: 15 in US 2003/0039636. In another embodiment, the right (3') LTR further comprises a polyadenylation sequence downstream from the hybrid R region. In another embodiment, the polyadenylation sequence comprises the nucleotide sequence shown in SEQ ID NO: 16 in US 2003/0039636. In yet another embodiment, the entire right (5') LTR comprises the nucleotide sequence shown in SEQ ID NO: 2 or 17 of US 2003/0039636.

Thus, in the case of HIV based LV, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower.

It has also been demonstrated that the trans-acting function of Tat becomes dispensable if part of the upstream LTR in the transfer vector construct is replaced by constitutively active promoter sequences (see, e.g., Dull et al. (1998) *J Virol.* 72(11): 8463-8471. Furthermore, we show that the expression of rev in trans allows the production of high-titer HIV-derived vector stocks from a packaging construct which contains only gag and pol. This design makes the expression of the packaging functions conditional on complementation available only in producer cells. The resulting gene delivery system, conserves only three of the nine genes of HIV-1 and relies on four separate transcriptional units for the production of transducing particles.

In one embodiment illustrated in Example 1, the cassette expressing a FoxP3 cDNA operably linked to an endogenous FoxP3 promoter, and optionally FoxP3 regulatory control elements is placed in the pCCL LV backbone, which is a SIN vector with the CMV enhancer/promoter substituted in the 5' LTR.

It will be recognized that the CMV promoter typically provides a high level of non-tissue specific expression. Other promoters with similar constitutive activity include, but are not limited to the RSV promoter, and the SV40 promoter. Mammalian promoters such as the beta-actin promoter, ubiquitin C promoter, elongation factor lapromoter, tubulin promoter, etc., may also be used.

The foregoing SIN configurations are illustrative and non-limiting. Numerous SIN configurations are known to those of skill in the art. As indicated above, in certain embodiments, the LTR transcription is reduced by about 95% to about 99%. In certain embodiments LTR may be rendered at least about 90%, at least about 91%, at least about 92%, at least about 93%, at least about 94%, at least about 95% at least about 96%, at least about 97%, at least about 98%, or at least about 99% transcriptionally inactive.

Packaging Signal

In various embodiments the vectors described herein comprise a packaging signal. A "packaging signal," "packaging sequence," or "psi sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art.

Rev Responsive Element (RRE)

In certain embodiments the LVs described herein comprise a Rev response element (RRE) to enhance nuclear export of unspliced RNA. RREs are well known to those of skill in the art. Illustrative RREs include, but are not limited to RREs such as that located at positions 7622-8459 in the HIV NL4-3 genome (Genbank accession number AF003887) as well as RREs from other strains of HIV or other retroviruses. Such sequences are readily available from Genbank or from the database with URL hiv-web.lanl-.gov/content/index.

Central PolyPurine Tract (cPPT)

In various embodiments the vectors described herein include a central polypurine tract. Insertion of a fragment containing the central polypurine tract (cPPT) in lentiviral (e.g., HIV-1) vector constructs is known to enhance transduction efficiency drastically, reportedly by facilitating the nuclear import of viral cDNA through a central DNA flap.

Expression-Stimulating Posttranscriptional Regulatory Element (PRE)

In certain embodiments the LVs described herein may comprise any of a variety of posttranscriptional regulatory elements (PREs) whose presence within a transcript increases expression of the heterologous nucleic acid (e.g., a human FoxP3 cDNA) at the protein level. PREs may be particularly useful in certain embodiments, especially those that involve lentiviral constructs with modest promoters.

One type of PRE is an intron positioned within the expression cassette, which can stimulate gene expression. However, introns can be spliced out during the life cycle events of a lentivirus. Hence, if introns are used as PRE's they are typically placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is typically preferred as it contains an additional cis-acting element not found in the HPRE. This regulatory element is typically positioned within the vector so as to be included in the RNA transcript of the transgene, but outside of stop codon of the transgene translational unit.

The WPRE is characterized and described in U.S. Pat. No. 6,136,597. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7 to 10 fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE in a vector results in enhanced expression of transgenes.

Insulator Element

In certain embodiments, to further enhance biosafety, insulators can be inserted into the LV described herein. Insulators are DNA sequence elements present throughout the genome. They bind proteins that modify chromatin and alter regional gene expression. The placement of insulators in the vectors described herein offer various potential benefits including, inter alia: 1) Shielding of the vector from positional effect variegation of expression by flanking chromosomes (i.e., barrier activity); and 2) Shielding flanking chromosomes from insertional trans-activation of gene expression by the vector (enhancer blocking). Thus, insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Natl. Acad. Sci. USA,* 99: 16433; and Zhan et al. (2001) *Hum. Genet.,* 109: 471). In the present context insulators may contribute to protecting lentivirus-expressed sequences from integration site effects, which may be mediated by cis-acting elements present in genomic DNA and lead to deregulated expression of transferred sequences. In various embodiments LVs are provided in which an insulator sequence is inserted into one or both LTRs or elsewhere in the region of the vector that integrates into the cellular genome.

The first and best characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) *EMBO J.* 18: 4035-4048). A 1.2-kb fragment containing the cHS4 element displays classic insulator activities, including the ability to block the interaction of globin gene promoters and enhancers in cell lines (Chung et al. (1993) Cell, 74: 505-514), and the ability to protect expression cassettes in Drosophila (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) *Transgenic Res.,* 8: 223-235) from position effects. Much of this activity is contained in a 250-bp fragment. Within this stretch is a 49-bp cHS4 core (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

One illustrative and suitable insulator is FB (FII/BEAD-A), a 77 bp insulator element, that contains the minimal CTCF binding site enhancer-blocking components of the chicken β-globin 5' HS4 insulators and a homologous region from the human T-cell receptor alpha/delta blocking element alpha/delta I (BEAD-I) insulator described by Ramezani et al. (2008) *Stem Cell* 26: 3257-3266. The FB "synthetic" insulator has full enhancer blocking activity. This insulator is illustrative and non-limiting. Other suitable insulators may be used including, for example, the full length chicken beta-globin HS4 or insulator sub-fragments thereof, the ankyrin gene insulator, and other synthetic insulator elements.

In certain embodiments there is an A2 insulator contained within the U3 region.

Transduced Host Cells and Methods of Cell Transduction

The recombinant LV and resulting virus described herein are capable of transferring a nucleic acid (e.g., a nucleic acid encoding a human FoxP3 protein) sequence into a mammalian cell. For delivery to cells, vectors of the present invention are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

The recombinant LVs and resulting virus described herein are capable of transferring a nucleic acid sequence (e.g., a nucleic acid encoding a human FoxP3 protein) into a mammalian cell. For delivery to cells, vectors of the present invention are typically used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

Typically, the vectors are introduced via transfection into the packaging cell line. The packaging cell line produces viral particles that contain the vector genome. Methods for transfection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neomycin, DHFR, Glutamine synthetase, followed by selection in the presence of the appropriate drug and isolation of clones. In certain embodiments the selectable marker gene can be linked physically to the packaging genes in the construct.

Stable cell lines wherein the packaging functions are configured to be expressed by a suitable packaging cell are known (see, e.g., U.S. Pat. No. 5,686,279, which describes packaging cells). In general, for the production of virus particles, one may employ any cell that is compatible with the expression of lentiviral Gag and Pol genes, or any cell that can be engineered to support such expression. For example, producer cells such as 293T cells and HT1080 cells may be used.

The packaging cells with a lentiviral vector incorporated in them form producer cells. Producer cells are thus cells or cell-lines that can produce or release packaged infectious viral particles carrying the therapeutic gene of interest (e.g., human FoxP3 gene or cDNA). These cells can further be anchorage dependent which means that these cells will grow, survive, or maintain function optimally when attached to a surface such as glass or plastic. Some examples of anchorage dependent cell lines used as lentiviral vector packaging cell lines when the vector is replication competent are HeLa or 293 cells and PERC.6 cells.

Accordingly, in certain embodiments, methods are provided of delivering a gene to a cell which is then integrated into the genome of the cell, comprising contacting the cell with a virion containing a lentiviral vector described herein. The cell (e.g., in the form of tissue or an organ) can be contacted (e.g., infected) with the virion ex vivo and then delivered to a subject (e.g., a mammal, animal or human) in which the gene (e.g., FoxP3 gene or cDNA) will be expressed. In various embodiments the cell can be autologous to the subject (i.e., from the subject) or it can be non-autologous (i.e., allogeneic or xenogenic) to the subject. Moreover, because the vectors described herein are capable of being delivered to both dividing and non-dividing cells, the cells can be from a wide variety including, for example, bone marrow cells, mesenchymal stem cells (e.g., obtained from adipose tissue), and other primary cells derived from human and animal sources. Alternatively, the virion can be directly administered in vivo to a subject or a localized area of a subject (e.g., bone marrow).

Of course, as noted above, the lentivectors described herein will be particularly useful in the transduction of human hematopoietic progenitor cells or a hematopoietic stem cells, obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ cells. In certain embodiments particularly preferred targets are $CD34^+$/$CD38^-$ cells.

Gene Therapy

In still other embodiments, the present invention is directed to a method for transducing a human hematopoietic stem cell comprising contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a human patient, using methods well known to those of skill in the art and transduced as noted above. The transduced stem cells are then reintroduced into the same or a different human.

Stem Cell/Progenitor Cell Gene Therapy

In various embodiments the lentivectors described herein are particularly useful for the transduction of human hematopoietic progenitor cells or hematopoietic stem cells (HSCs), obtained either from the bone marrow, the peripheral blood or umbilical cord blood, as well as in the transduction of a $CD4^+$ T cell, a peripheral blood B or T lymphocyte cell, and the like. In certain embodiments particularly preferred targets are $CD34^+$ cells. In certain embodiments the preferred targets are $CD34^+$/$CD38^-$ cells.

In certain embodiments, when cells, for instance $CD34^+$ cells, dendritic cells, peripheral blood cells or tumor cells are transduced ex vivo, the virus particles are incubated with the cells using a dose generally in the order of between 1 to 50 multiplicities of infection (MOI) which also corresponds to $1\times10^5$ to $50\times10^5$ transducing units of the viral vector per $10^5$ cells. This can include amounts of vector corresponding to 1, 2, 3, 4, 5, 6, 7, 8, 9, 10, 15, 20, 25, 30, 35, 40, 45, and 50 MOI. Typically, the amount of vector may be expressed in terms of HT-29 transducing units (TU).

In certain embodiments cell-based therapies involve providing stem cells and/or hematopoietic precursors, transduce the cells with the lentivirus encoding a nucleic acid that expresses FoxP3 protein and then introduce the transduced cells into a subject in need thereof (e.g., a subject with a FoxP3 deficiency and/or mutation, e.g., a subject with an autoimmune disorder).

In certain embodiments the methods involve isolating population of cells, e.g., stem cells from a subject, optionally expand the cells in tissue culture, and administer the lentiviral vector whose presence within a cell results in production of FoxP3 in vitro. The cells are then returned to the subject, where, for example, they may provide a population of white blood cells that produce FoxP3 and thereby correct a FoxP3 deficiency and/or mutation. In certain embodiments, in view of the presence of the endogenous promoter, and in certain embodiments, endogenous enhancers (e.g., FoxP3 conserved non-coding sequence 1 (FoxP3-CNS1), and/or FoxP3 conserved non-coding sequence 2 (FoxP3-CNS2), and/or FoxP3 conserved non-coding sequence 3 (FoxP3-CNS3) the FoxP3 expression recapitulates normal physiologic expression of FoxP3.

In some embodiments, a population of cells, which may be cells from a cell line or from an individual other than the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

Where stem cells are to be used, it will be recognized that such cells can be derived from a number of sources including bone marrow (BM), cord blood (CB), mobilized peripheral blood stem cells (mPBSC), and the like. In certain embodiments the use of induced pluripotent stem cells (IPSCs) is contemplated. Methods of isolating hematopoietic stem cells (HSCs), transducing such cells and introducing them into a mammalian subject are well known to those of skill in the art.

In certain embodiments a lentiviral vector described herein (see, e.g., FIGS. 6 and 7, and SEQ ID NO:1) is used in stem cell gene therapy for conditions characterized by deficient or defective FoxP3 expression, by introducing the nucleic acid encoding FoxP3 protein into the bone marrow stem cells of patients with, for example an autoimmune disease as described herein, followed by autologous transplantation.

Direct Introduction of Vector

In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include inhalation, parenteral, and transmucosal.

In various embodiments pharmaceutical compositions can include an LV in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral vector, a viral particle, etc., described herein and/or other agents to be administered together the vector, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Suitable materials can also be obtained commercially from Alza Corporation and Nova Pharmaceuticals, Inc. Liposomes can also be used as pharmaceutically acceptable carriers. These can be prepared according to methods known to those skilled in the art, for example, as described in U.S. Pat. No. 4,522,811. In some embodiments the composition is targeted to particular cell types or to cells that are infected by a virus. For example, compositions can be targeted using monoclonal antibodies to cell surface markers, e.g., endogenous markers or viral antigens expressed on the surface of infected cells.

It is advantageous to formulate compositions in dosage unit form for case of administration and uniformity of dosage. Dosage unit form as used herein refers to physically discrete units suited as unitary dosages for the subject to be treated; each unit comprising a predetermined quantity of a LV calculated to produce the desired therapeutic effect in association with a pharmaceutical carrier.

A unit dose need not be administered as a single injection but may comprise continuous infusion over a set period of time. Unit dose of the LV described herein may conveniently be described in terms of transducing units (T.U.) of lentivector, as defined by titering the vector on a cell line such as HeLa or 293. In certain embodiments unit doses can range from $10^3$, $10^4$, $10^5$, $10^6$, $10^7$, $10^8$, $10^9$, $10^{10}$, $10^{11}$, $10^{12}$, $10^{13}$ T.U. and higher.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. It may be necessary to administer the therapeutic composition on an indefinite basis. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a LV can include a single treatment or, in many cases, can include a series of treatments.

Exemplary doses for administration of gene therapy vectors and methods for determining suitable doses are known in the art. It is furthermore understood that appropriate doses of a LV may depend upon the particular recipient and the mode of administration. The appropriate dose level for any particular subject may depend upon a variety of factors including the age, body weight, general health, gender, and diet of the subject, the time of administration, the route of administration, the rate: of excretion, other administered therapeutic agents, and the like.

In certain embodiments lentiviral gene therapy vectors can be delivered to a subject by, for example, intravenous injection, local administration, or by stereotactic injection (see, e.g., Chen et al. (1994) *Proc. Natl. Acad. Sci. USA,* 91: 3054). In certain embodiments vectors may be delivered orally or inhalationally and may be encapsulated or otherwise manipulated to protect them from degradation, enhance uptake into tissues or cells, etc. Pharmaceutical preparations can include a LV in an acceptable diluent, or can comprise a slow release matrix in which a LV is imbedded. Alternatively or additionally, where a vector can be produced intact from recombinant cells, as is the case for retroviral or lentiviral vectors as described herein, a pharmaceutical preparation can include one or more cells which produce vectors. Pharmaceutical compositions comprising a LV described herein can be included in a container, pack, or dispenser, optionally together with instructions for administration.

The foregoing compositions, methods and uses are intended to be illustrative and not limiting. Using the teachings provided herein other variations on the compositions, methods and uses will be readily available to one of skill in the art.

EXAMPLES

The following examples are offered to illustrate, but not to limit the claimed invention.

Example 1

Evaluation of the pCCL-CNSp-FOXP3-3UTR-A2 Vector

FIGS. 6 and 7 illustrate the structure of a lentiviral vector that encodes FoxP3 under control of the endogenous FoxP3 promoter and enhancers (CNS1, CNS2, and CNS3). In particular, FIG. 6 illustrates the structure of the pCCL-CNSp-FOXP3-3UTR-A2 vector (SEQ ID NO:1 (sequence from junction marker) also shown in Table 1, below). Sequences of human genomic origin include: CNS1 (237 bp) which is a minimal sequence based on, but not identical to, a sequence described by Tone et al. (2008) *Nat. Immunol.* 9: 194-202, CNS2 (359 bp) which is described by Kim and Leonard (2007) *J. Exp. Med.* 204: 1543-1551, CNS3 (217 bp) which is described by Zheng et al. (2010) *Nature,* 473: 808-813, the FoxP3 promoter (382 bp) which is modified from the sequence described by Kim and Leonard (2007), supra., a 5'UTR (187 bp) based on human genomic NCBI reference sequence file NM_014009, a FoxP3 cDNA (1292 bp) based on human genomic NCBI reference sequence file NM_014009, and a 3'UTR (875 bp) based on human genomic NCBI reference sequence file NM_014009.

TABLE 1

Foxp3 Expression Vector nucleotide sequence. Sequence shown from junction marker.

| Sequence | SEQ ID NO: |
|---|---|
| Sequence from junction marker: | 1 |
| CAGGTGGCACTTTTCGGGGAAATGTGCGCGGAACCCCTATTTGTTTATTTTTCT | |
| AAATACATTCAAATATGTATCCGCTCATGAGACAATAACCCTGATAAATGCTTC | |
| AATAATATTGAAAAAGGAAGAGTATGAGTATTCAACATTTCCGTGTCGCCCTTA | |
| TTCCCTTTTTTGCGGCATTTTGCCTTCCTGTTTTTGCTCACCCAGAAACGCTGG | |
| TGAAAGTAAAAGATGCTGAAGATCAGTTGGGTGCACGAGTGGGTTACATCGAAC | |
| TGGATCTCAACAGCGGTAAGATCCTTGAGAGTTTTCGCCCCGAAGAACGTTTTC | |
| CAATGATGAGCACTTTTAAAGTTCTGCTATGTGGCGCGGTATTATCCCGTATTG | |
| ACGCCGGGCAAGAGCAACTCGGTCGCCGCATACACTATTCTCAGAATGACTTGG | |
| TTGAGTACTCACCAGTCACAGAAAAGCATCTTACGGATGGCATGACAGTAAGAG | |
| AATTATGCAGTGCTGCCATAACCATGAGTGATAACACTGCGGCCAACTTACTTC | |
| TGACAACGATCGGAGGACCGAAGGAGCTAACCGCTTTTTTGCACAACATGGGGG | |
| ATCATGTAACTCGCCTTGATCGTTGGGAACCGGAGCTGAATGAAGCCATACCAA | |
| ACGACGAGCGTGACACCACGATGCCTGTAGCAATGGCAACAACGTTGCGCAAAC | |
| TATTAACTGGCGAACTACTTACTCTAGCTTCCCGGCAACAATTAATAGACTGGA | |
| TGGAGGCGGATAAAGTTGCAGGACCACTTCTGCGCTCGGCCCTTCCGGCTGGCT | |
| GGTTTATTGCTGATAAATCTGGAGCCGGTGAGCGTGGGTCTCGCGGTATCATTG | |
| CAGCACTGGGGCCAGATGGTAAGCCCTCCCGTATCGTAGTTATCTACACGACGG | |
| GGAGTCAGGCAACTATGGATGAACGAAATAGACAGATCGCTGAGATAGGTGCCT | |
| CACTGATTAAGCATTGGTAACTGTCAGACCAAGTTTACTCATATATACTTTAGA | |
| TTGATTTAAAACTTCATTTTTAATTTAAAAGGATCTAGGTGAAGATCCTTTTTG | |
| ATAATCTCATGACCAAAATCCCTTAACGTGAGTTTTCGTTCCACTGAGCGTCAG | |
| ACCCCGTAGAAAAGATCAAAGGATCTTCTTGAGATCCTTTTTTTCTGCGCGTAA | |
| TCTGCTGCTTGCAAACAAAAAAACCACCGCTACCAGCGGTGGTTTGTTTGCCGG | |
| ATCAAGAGCTACCAACTCTTTTTCCGAAGGTAACTGGCTTCAGCAGAGCGCAGA | |
| TACCAAATACTGTCCTTCTAGTGTAGCCGTAGTTAGGCCACCACTTCAAGAACT | |
| CTGTAGCACCGCCTACATACCTCGCTCTGCTAATCCTGTTACCAGTGGCTGCTG | |
| CCAGTGGCGATAAGTCGTGTCTTACCGGGTTGGACTCAAGACGATAGTTACCGG | |
| ATAAGGCGCAGCGGTCGGGCTGAACGGGGGGTTCGTGCACACAGCCCAGCTTGG | |
| AGCGAACGACCTACACCGAACTGAGATACCTACAGCGTGAGCTATGAGAAAGCG | |
| CCACGCTTCCCGAAGGGAGAAAGGCGGACAGGTATCCGGTAAGCGGCAGGGTCG | |
| GAACAGGAGAGCGCACGAGGGAGCTTCCAGGGGGAAACGCCTGGTATCTTTATA | |
| GTCCTGTCGGGTTTCGCCACCTCTGACTTGAGCGTCGATTTTTGTGATGCTCGT | |
| CAGGGGGGCGGAGCCTATGGAAAAACGCCAGCAACGCGGCCTTTTTACGGTTCC | |
| TGGCCTTTTGCTGGCCTTTTGCTCACATGTTCTTTCCTGCGTTATCCCCTGATT | |
| CTGTGGATAACCGTATTACCGCCTTTGAGTGAGCTGATACCGCTCGCCGCAGCC | |
| GAACGACCGAGCGCAGCGAGTCAGTGAGCGAGGAAGCGGAAGAGCGCCCAATAC | |
| GCAAACCGCCTCTCCCCGCGCGTTGGCCGATTCATTAATGCAGCTGGCACGACA | |
| GGTTTCCCGACTGGAAAGCGGGCAGTGAGCGCAACGCAATTAATGTGAGTTAGC | |
| TCACTCATTAGGCACCCCAGGCTTTACACTTTATGCTTCCGGCTCGTATGTTGT | |
| GTGGAATTGTGAGCGGATAACAATTTCACACAGGAAACAGCTATGACCATGATT | |
| ACGCCAAGCGCGCAATTAACCCTCACTAAAGGGAACAAAAGCTGGAGCTGCAAG | |
| CTTGGCCATTGCATACGTTGTATCCATATCATAATATGTACATTTATATTGGCT | |
| CATGTCCAACATTACCGCCATGTTGACATTGATTATTGACTAGTTATTAATAGT | |
| AATCAATTACGGGGTCATTAGTTCATAGCCCATATATGGAGTTCCGCGTTACAT | |
| AACTTACGGTAAATGGCCCGCCTGGCTGACCGCCCAACGACCCCCGCCCATTGA | |
| CGTCAATAATGACGTATGTTCCCATAGTAACGCCAATAGGGACTTTCCATTGAC | |
| GTCAATGGGTGGAGTATTTACGGTAAACTGCCCACTTGGCAGTACATCAAGTGT | |
| ATCATATGCCAAGTACGCCCCCTATTGACGTCAATGACGGTAAATGGCCCGCCT | |
| GGCATTATGCCCAGTACATGACCTTATGGGACTTTCCTACTTGGCAGTACATCT | |
| ACGTATTAGTCATCGCTATTACCATGGTGATGCGGTTTTGGCAGTACATCAATG | |
| GGCGTGGATAGCGGTTTGACTCACGGGGATTTCCAAGTCTCCACCCCATTGACG | |
| TCAATGGGAGTTTGTTTTGGCACCAAAATCAACGGGACTTTCCAAAATGTCGTA | |
| ACAACTCCGCCCCATTGACGCAAATGGGCGGTAGGCGTGTACGGTGGGAGGTCT | |

TABLE 1-continued

Foxp3 Expression Vector nucleotide sequence. Sequence shown from junction marker.

| Sequence | SEQ ID NO: |
|---|---|
| ATATAAGCAGAGCTCGTTTAGTGAACCGGGGTCTCTCTGGTTAGACCAGATCTG | |
| AGCCTGGGAGCTCTCTGGCTAACTAGGGAACCCACTGCTTAAGCCTCAATAAAG | |
| CTTGCCTTGAGTGCTTCAAGTAGTGTGTGCCCGTCTGTTGTGTGACTCTGGTAA | |
| CTAGAGATCCCTCAGACCCTTTTAGTCAGTGTGGAAAATCTCTAGCAGTGGCGC | |
| CCGAACAGGGACCTGAAAGCGAAAGGGAAACCAGAGGAGCTCTCTCGACGCAGG | |
| ACTCGGCTTGCTGAAGCGCGCACGGCAAGAGGCGAGGGGCGGCGACTGGTGAGT | |
| ACGCCAAAAATTTTGACTAGCGGAGGCTAGAAGGAGAGAGATGGGTGCGAGAGC | |
| GTCAGTATTAAGCGGGGGAGAATTAGATCGCGATGGGAAAAAATTCGGTTAAGG | |
| CCAGGGGGAAAGAAAAAATATAAATTAAAACATATAGTATGGGCAAGCAGGGAG | |
| CTAGAACGATTCGCAGTTAATCCTGGCCTGTTAGAAACATCAGAAGGCTGTAGA | |
| CAAATACTGGGACAGCTACAACCATCCCTTCAGACAGGATCAGAAGAACTTAGA | |
| TCATTATATAATACAGTAGCAACCCTCTATTGTGTGCATCAAAGGATAGAGATA | |
| AAAGACACCAAGGAAGCTTTAGACAAGATAGAGGAAGAGCAAAACAAAAGTAAG | |
| ACCACCGCACAGCAAGCGGCCGCTGATCTTCAGACCTGGAGGAGGAGATATGAG | |
| GGACAATTGGAGAAGTGAATTATATAAATATAAAGTAGTAAAAATTGAACCATT | |
| AGGAGTAGCACCCACCAAGGCAAAGAGAAGAGTGGTGCAGAGAGAAAAAAGAGC | |
| AGTGGGAATAGGAGCTTTGTTCCTTGGGTTCTTGGGAGCAGCAGGAAGCACTAT | |
| GGGCGCAGCGTCAATGACGCTGACGGTACAGGCCAGACAATTATTGTCTGGTAT | |
| AGTGCAGCAGCAGAACAATTTGCTGAGGGCTATTGAGGCGCAACAGCATCTGTT | |
| GCAACTCACAGTCTGGGGCATCAAGCAGCTCCAGGCAAGAATCCTGGCTGTGGA | |
| AAGATACCTAAAGGATCAACAGCTCCTGGGGATTTGGGGTTGCTCTGGAAAACT | |
| CATTTGCACCACTGCTGTGCCTTGGAATGCTAGTTGGAGTAATAAATCTCTGGA | |
| ACAGATGGAATCACACGACCTGGATGGAGTGGGACAGAGAAATTAACAATTACA | |
| CAAGCTTAATACACTCCTTAATTGAAGAATCGCAAAACCAGCAAGAAAAGAATG | |
| AACAAGAATTATTGGAATTAGATAAATGGGCAAGTTTGTGGAATTGGTTTAACA | |
| TAACAAATTGGCTGTGGTATATAAAATTATTCATAATGATAGTAGGAGGCTTGG | |
| TAGGTTTAAGAATAGTTTTTGCTGTACTTTCTATAGTGAATAGAGTTAGGCAGG | |
| GATATTCACCATTATCGTTTCAGACCCACCTCCCAACCCCGAGGGGACCCGACA | |
| GGCCCGAAGGAATAGAAGAAGAAGGTGGAGAGAGAGACAGAGACAGATCCATTC | |
| GATTAGTGAACGGATCTCGACGGTATCGATCTCGACACAAATGGCAGTATTCAT | |
| CCACAATTTTAAAAGAAAAGGGGGGATTGGGGGGTACAGTGCAGGGGAAAGAAT | |
| AGTAGACATAATAGCAACAGACATACAAACTAAAGAATTACAAAAACAAATTAC | |
| AAAAATTCAAAATTTTCGGGTTTATTACAGGGACAGCAGAGATCCAGTTTGGGT | |
| CGAGGATATCTAGGTTAGTCTTTTTTTCTGTGGCTTCTGTCTCTGGTTTTGTGC | |
| TTAGAAAGTCCTTTCCTACTTGAAAATGAGATAAATGTTCACCTATGTTGGCTT | |
| CTAGTCTCTTTTATGGCTTCATTTTTTCCATTTACTATAGAGGTTAAGAGTGTG | |
| GGTACTGGAGCCAGACTGTCTGGGACAAACCCAGCGTCACCCCAAGCCCTATGT | |
| GTGATTTTTAGCCAGGCACTTAACCTCTCCATCCAAGAAGGGCCAGGTCTTCAG | |
| AGCTAGGGGCTTGTCATAGTGGCCAGATGGACATCACCTACCACATCCACCAGC | |
| ACCCATGTCACCCCACCTGGGCCAAGCCTGCTGCAGGACAGGGCAGCCAGTTCT | |
| CGGAACGAAACCTGTGGGGTGGGGTATCTGCCCTCTTCTCTTCCTCCGTGGTGT | |
| CGATGAAGCCCGGCGCATCCGGCCGCCATGACGTCAATGGCGGAAAAATCTGGG | |
| CAAGTCGGGGGCTGTGACAACAGGGCCCAGATGCAGACCCCGATATGAAAACAT | |
| AATCTGTGTCCCAGAAACATCCCCCATTCAGCTTCTGAGAAACCCAGTCAGAAA | |
| GGGACGTCCCAACAGAGGCCCTGGGCCCAGGATGGGGCAGGCAGGGTGGGGTAC | |
| CTGGACCTACAGGTGCCGACCTTTACTGTGGCACTGGGCGGGAGGGGGGCTGGC | |
| TGGGGCACAGGAAGTGGTTTCTGGGTCCCAGGCAAGTCTGTGACTTATGCAGAT | |
| GTTGCAGGGCCAAGAAAATCCCCACCTGCCAGGCCTCAGAGATTGGAGGCTCTC | |
| CCCGACCTCCCAATCCTCCCATCCACACATAGAGCTTCAGATTCTCTTTCTTTC | |
| CCCAGAGACCCTCAAATATCCTCTCACTCACAGAATGGTGTCTCTGCCTGCCTC | |
| GGGTTGGCCCTGTGATTTATTTTAGTTCTTTTCCCTTGTTTTTTTTTTTTTCAAA | |
| CTCTATACACTTTTGTTTTAAAAACTGTGGTTTCTCATGAGCCCTATTATCTCA | |
| TTGATACCTCTCACCTCTGTGGTGAGGGGAAGAAATCATATTTTCAGATGACTC | |
| GTAAAGGGCAAAGAAAAAAACCCAAAATTTCAAAATTTCCGTTTAAGTCTCATA | |
| ATCAAGAAAAGGAGAAACACAGAGAGAGAGAAAAAAAAAAACTATGAGAACCCCT | |
| CCCCACCCCGTGATTATCAGCGCACACACTCATCGAAAAAAATTTGGATTATTA | |
| GAAGAGAGAGGTCTGCGGCTTCCACACCGTACAGCGTGGTTTTTCTTCTCGGTA | |
| TAAAAGCAAAGTTGTTTTTGATACGTGACAGTTTCCCACAAGCCAGGCTGATCC | |
| TTTTCTGTCAGTCCACTTCACCAAGCCTGCCCTTGGACAAGGACCCGATGCCCA | |
| ACCCCAGGCCTGGCAAGCCCTCGGCCCCTTCCTTGGCCCTTGGCCCATCCCCAG | |
| GAGCCTCGCCCAGCTGGAGGGCTGCACCCAAAGCCTCAGACCTGCTGGGGGCCC | |
| GGGGCCCAGGGGGAACCTTCCAGGGCCGAGATCTTCGAGGCGGGGCCCATGCCT | |
| CCTCTTCTTCCTTGAACCCCATGCCACCATCGCAGCTGCAGCTGCCCACACTGC | |
| CCCTAGTCATGGTGGCACCCTCCGGGGCACGGCTGGGCCCCTTGCCCCACTTAC | |
| AGGCACTCCTCCAGGACAGGCCACATTTCATGCACCAGCTCTCAACGGTGGATG | |
| CCCACGCCCGGACCCCTGTGCTGCAGGTGCACCCCCTGGAGAGCCCAGCCATGA | |
| TCAGCCTCACACCACCCACCACCGCCACTGGGGTCTTCTCCCTCAAGGCCCGGC | |
| CTGGCCTCCCACCTGGGATCAACGTGGCCAGCCTGGAATGGGTGTCCAGGGAGC | |
| CGGCACTGCTCTGCACCTTCCCAAATCCCAGTGCACCCAGGAAGGACAGCACCC | |
| TTTCGGCTGTGCCCCAGAGCTCCTACCCACTGCTGGCAAATGGTGTCTGCAAGT | |
| GGCCCGGATGTGAGAAGGTCTTCGAAGAGCCAGAGGACTTCCTCAAGCACTGCC | |
| AGGCGGACCATCTTCTGGATGAGAAGGGCAGGGCACAATGTCTCCTCCAGAGAG | |
| AGATGGTACAGTCTCTGGAGCAGCAGCTGGTGCTGGAGAAGGAGAAGCTGAGTG | |

TABLE 1-continued

Foxp3 Expression Vector nucleotide sequence. Sequence shown from junction marker.

| Sequence | SEQ ID NO: |
|---|---|
| CCATGCAGGCCCACCTGGCTGGGAAAATGGCACTGACCAAGGCTTCATCTGTGG | |
| CATCATCCGACAAGGGCTCCTGCTGCATCGTAGCTGCTGGCAGCCAAGGCCCTG | |
| TCGTCCCAGCCTGGTCTGGCCCCCGGGAGGCCCCTGACAGCCTGTTTGCTGTCC | |
| GGAGGCACCTGTGGGGTAGCCATGGAAACAGCACATTCCCAGAGTTCCTCCACA | |
| ACATGGACTACTTCAAGTTCCACAACATGCGACCCCCTTTCACCTACGCCACGC | |
| TCATCCGCTGGGCCATCCTGGAGGCTCCAGAGAAGCAGCGGACACTCAATGAGA | |
| TCTACCACTGGTTCACACGCATGTTTGCCTTCTTCAGAAACCATCCTGCCACCT | |
| GGAAGAACGCCATCCGCCACAACCTGAGTCTGCACAAGTGCTTTGTGCGGGTGG | |
| AGAGCGAGAAGGGGGCTGTGTGGACCGTGGATGAGCTGGAGTTCCGCAAGAAAC | |
| GGAGCCAGAGGCCCAGCAGGTGTTCCAACCCTACACCTGGCCCCTGATGACCTC | |
| AAGATCAAGGAAAGGAGGATGGACGAACAGGGGCCAAACTGGTGGGAGGCAGAG | |
| GTGGTGGGGGCAGGGATGATAGGCCCTGGATGTGCCCACAGGGACCAAGAAGTG | |
| AGGTTTCCACTGTCTTGCCTGCCAGGGCCCCTGTTCCCCCGCTGGCAGCCACCC | |
| CCTCCCCCATCATATCCTTTGCCCCAAGGCTGCTCAGAGGGGCCCCGGTCCTGG | |
| CCCCAGCCCCCACCTCCGCCCCAGACACACCCCCCAGTCGAGCCCTGCAGCCAA | |
| ACAGAGCCTTCACAACCAGCCACACAGAGCCTGCCTCAGCTGCTCGCACAGATT | |
| ACTTCAGGGCTGGAAAAGTCACACAGACACACAAAATGTCACAATCCTGTCCCT | |
| CACTCAACACAAACCCCAAAACACAGAGAGCCTGCCTCAGTACACTCAAACAAC | |
| CTCAAAGCTGCATCATCACACAATCACACACAAGCACAGCCCTGACAACCCACA | |
| CACCCCAAGGCACGCACCCACAGCCAGCCTCAGGGCCCACAGGGGCACTGTCAA | |
| CACAGGGGTGTGCCCAGAGGCCTACACAGAAGCAGCGTCAGTACCCTCAGGATC | |
| TGAGGTCCCAACACGTGCTCGCTCACACACACGGCCTGTTAGAATTCACCTGTG | |
| TATCTCACGCATATGCACACGCACAGCCCCCCAGTGGGTCTCTTGAGTCCCGTG | |
| CAGACACACACAGCCACACACACTGCCTTGCCAAAAATACCCCGTGTCTCCCCT | |
| GCCACTCACCTCACTCCCATTCCCTGAGCCCTGATCCATGCCTCAGCTTAGACT | |
| GCAGAGGAACTACTCATTTATTTGGGATCCAAGGCCCCCAACCCACAGTACCGT | |
| CCCCGAATTCGAGCTCGGTACCTTTAAGACCAATGACTTACAAGGCAGCTGTAG | |
| ATCTTAGCCACTTTTTAAAAGAAAAGGGGGGACTGGAAGGGCTAATTCACTCCC | |
| AACGAAGACAAGATCAGAGCGAGATTCCGTCTCAAAGAAAAAAAAAGTAATGAA | |
| ATGAATAAAATGAGTCCTAGAGCCAGTAAATGTCGTAAATGTCTCAGCTAGTCA | |
| GGTAGTAAAAGGTCTCAACTAGGCAGTGGCAGAGCAGGATTCAAATTCAGGGCT | |
| GTTGTGATGCCTCCGCAGACTCTGAGCGCCACCTGGTGGTAATTTGTCTGTGCC | |
| TCTTCTGACGTGGAAGAACAGCAACTAACACACTAACACGGCATTTACTATGGG | |
| CCAGCCATTGTTGCTTTTTGCTTGTACTGGGTCTCTCTGGTTAGACCAGATCTG | |
| AGCCTGGGAGCTCTCTGGCTAACTAGGGAACCCACTGCTTAAGCCTCAATAAAG | |
| CTTGCCTTGAGTGCTTCAAGTAGTGTGTGCCCGTCTGTTGTGTGACTCTGGTAA | |
| CTAGAGATCCCTCAGACCCTTTTAGTCAGTGTGGAAAATCTCTAGCAGTAGTAG | |
| TTCATGTCATCTTATTATTCAGTATTTATAACTTGCAAAGAAATGAATATCAGA | |
| GAGTGAGAGGAACTTGTTTATTGCAGCTTATAATGGTTACAAATAAAGCAATAG | |
| CATCACAAATTTCACAAATAAAGCATTTTTTTCACTGCATTCTAGTTGTGGTTTG | |
| TCCAAACTCATCAATGTATCTTATCATGTCTGGCTCTAGCTATCCCGCCCCTAA | |
| CTCCGCCCATCCCGCCCCTAACTCCGCCCAGTTCCGCCCATTCTCCGCCCCATG | |
| GCTGACTAATTTTTTTTATTTATGCAGAGGCCGAGGCCGCCTCGGCCTCTGAGC | |
| TATTCCAGAAGTAGTGAGGAGGCTTTTTTGGAGGCCTAGGCTTTTGCGTCGAGA | |
| CGTACCCAATTCGCCCTATAGTGAGTCGTATTACGCGCGCTCACTGGCCGTCGT | |
| TTTACAACGTCGTGACTGGGAAAACCCTGGCGTTACCCAACTTAATCGCCTTGC | |
| AGCACATCCCCCTTTCGCCAGCTGGCGTAATAGCGAAGAGGCCCGCACCGATCG | |
| CCCTTCCCAACAGTTGCGCAGCCTGAATGGCGAATGGCGCGACGCGCCCTGTAG | |
| CGGCGCATTAAGCGCGGCGGGTGTGGTGGTTACGCGCAGCGTGACCGCTACACT | |
| TGCCAGCGCCCTAGCGCCCGCTCCTTTCGCTTTCTTCCCTTCCTTTCTCGCCAC | |
| GTTCGCCGGCTTTCCCCGTCAAGCTCTAAATCGGGGGCTCCCTTTAGGGTTCCG | |
| ATTTAGTGCTTTACGGCACCTCGACCCCAAAAAACTTGATTAGGGTGATGGTTC | |
| ACGTAGTGGGCCATCGCCCTGATAGACGGTTTTTCGCCCTTTGACGTTGGAGTC | |
| CACGTTCTTTAATAGTGGACTCTTGTTCCAAACTGGAACAACACTCAACCCTAT | |
| CTCGGTCTATTCTTTTGATTTATAAGGGATTTTGCCGATTTCGGCCTATTGGTT | |
| AAAAAATGAGCTGATTTAACAAAAATTTAACGCGAATTTTAACAAAATATTAAC | |
| GTTTACAATTTCC | |

Sequences of human genomic origin:

CNS1 (237 bp) Minimal sequence based (but not identical to) Tone et al. (2008) *Nat. Immunol.* 9: 194-202

CNS2 (359 bp) Published by Kim & Leonard (2007) *J. Exp. Med.* 204: 1543-1551

CNS3 (217 bp) Published by Zheng et al. (2010) *Nature*, 463(7282): 808-812.

Promoter (382 bp) Sequence modified from Kim & Leonard (2007) *J. Exp. Med.* 204: 1543-1551

5' UTR (187 bp) based on human genomic NCBI reference sequence file NM_014009

FoxP3 cDNA (1292 bp) based on human genomic NCBI reference sequence file NM_014009

3' UTR (875 bp) based on human genomic NCBI reference sequence file NM_014009

Figure 1:
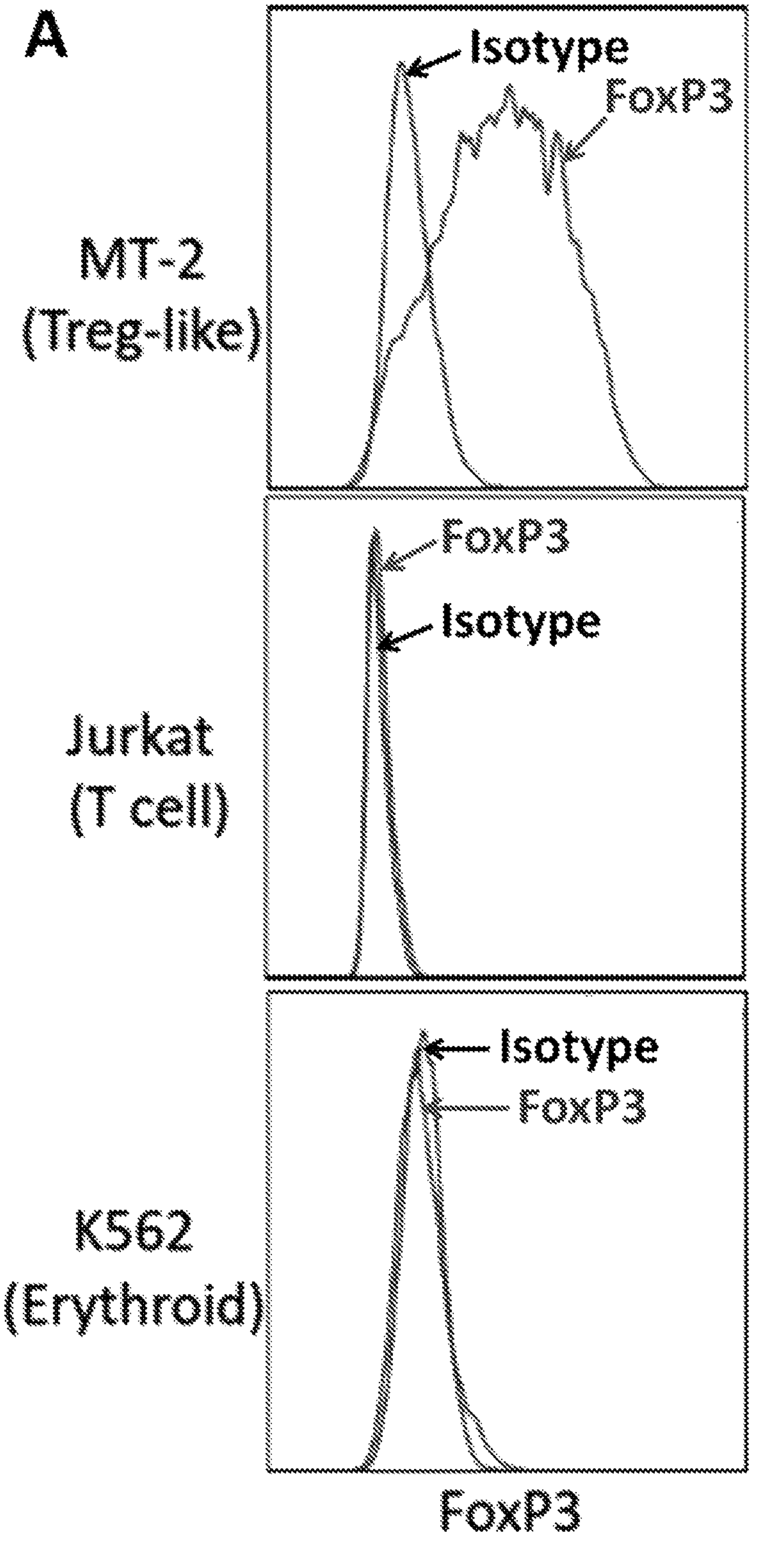
FIG. 1, panels A-B, shows that a FoxP3 reporter vector shows TReg lineage specific expression in human cell lines. Panel A) Flow cytometry measurement of endogenous FoxP3 protein expression in 3 different cell lines: MT-2 (T-reg like), Jurkat (T-cell), and K562 (Erythroid). Red histogram represents foxP3 expression, gray histogram depicts fluorescence of isotype control stained cells. Panel B) Expression of mStrawberry reporter protein in MT-2, Jurkat, or K562 cells transduced with a FoxP3-mStrawberry reporter vector. Y-axis represents the percentage of cells positive for mStrawberry expression, while x-axis represents the number of vector copies per cell.

As shown in FIG. 1, a FoxP3 reporter vector shows based on the construct described above shows TReg lineage specific expression in human cell lines. In particular, panel A shows a flow cytometry measurement of endogenous FoxP3 protein expression in 3 different cell lines: MT-2 (T-reg like), Jurkat (T-cell), and K562 (Erythroid). Panel B shows expression of mStrawberry reporter protein in MT-2, Jurkat, or K562 cells transduced with a FoxP3–mStrawberry reporter vector. The Y-axis represents the percentage of cells positive for mStrawberry expression, while the x-axis represents the number of vector copies per cell.

Figure 2:
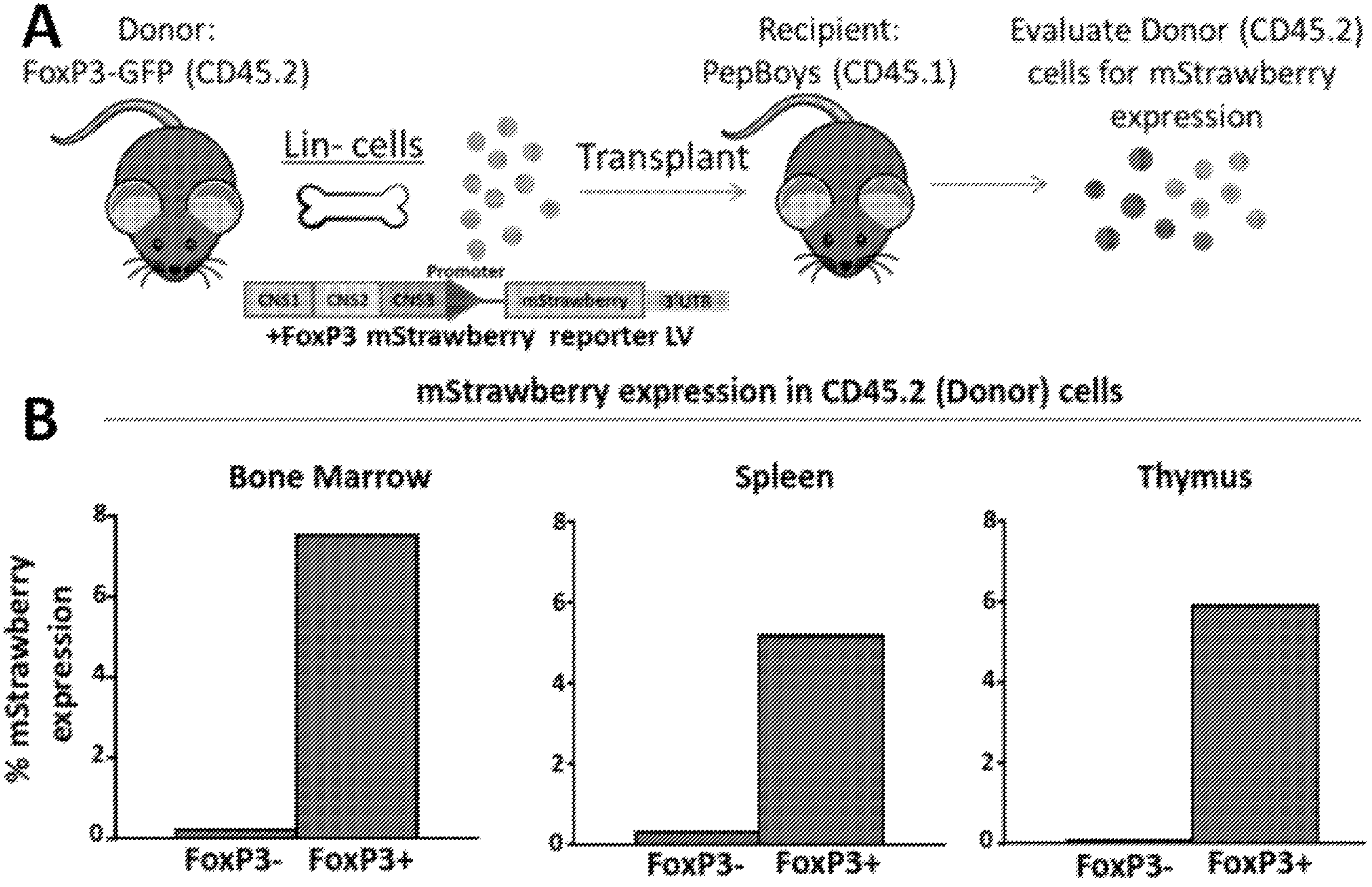
FIG. 2, panels A-B, shows that FoxP3 reporter vector shows TReg lineage specific expression in a murine congenic transplant model. Panel A) Transplant set up: CD45.2 FoxP3-GFP transgenic mice (which co-express FoxP3 and GFP) were used as bone marrow donors. Lin− cells were isolated from CD45.2 FoxP3-GFP mice and transduced with a FoxP3-mStrawberry reporter vector. Transduced lin− cells were transplanted into lethally irradiated congenic CD45.1 recipients. CD45.2 donor cells were analyzed at 10 weeks post-transplant for mStrawberry reporter vector expression in the Treg lineage (marked by FoxP3-GFP). Panel B) mStrawberry reporter expression was measured in FoxP3− (GFP−) and FoxP3+ (GFP+) donor cells in the bone marrow, spleen, and thymus of engrafted mice. Y axis represents the percentage of mStrawberry+ cells in each population.

FIG. 2 shows that the FoxP3 reporter vector shows TReg lineage specific expression in a murine congenic transplant model. CD45.2 FoxP3–GFP transgenic mice (which co-express FoxP3 and GFP) were used as bone marrow donors. Lin− cells were isolated from CD45.2 FoxP3–GFP mice and transduced with a FoxP3–mStrawberry reporter vector. Transduced lin− cells were transplanted into lethally irradiated congenic CD45.1 recipients. CD45.2 donor cells were analyzed at 10 weeks post-transplant for mStrawberry reporter vector expression in the Treg lineage (marked by FoxP3–GFP). As shown in panel B, mStrawberry reporter expression was measured in FoxP3− (GFP−) and FoxP3+ (GFP+) donor cells in the bone marrow, spleen, and thymus of engrafted mice. The Y axis represents the percentage of mStrawberry+ cells in each population.

Figure 3:
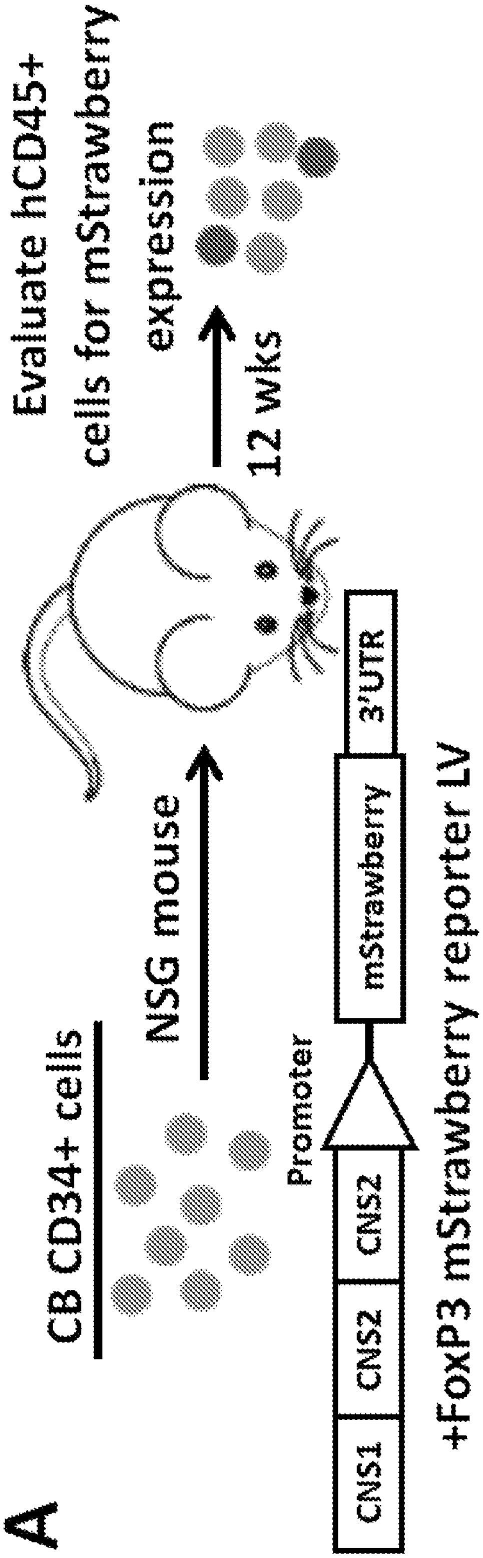
FIG. 3, panels A-D, shows that that FoxP3 reporter vector shows Treg lineage specific expression in a humanized mouse model. Panel A) Experimental set-up: CD34+ cells isolated from human cord blood were transduced with a FoxP3mStrawberry reporter vector and transplanted into neonatal immune-deficient NSG mice. 12 weeks post-transplant, engrafted hCD45+ cells were analyzed for mStrawberry expression. Panel B) Lineage specific mStrawberry expression in engrafted hCD45+ cells. hCD45+ cells were gated by lineage markers in NSG bone marrow (CD19+ B cells, CD33+ myeloid cells, CD34+ stem and progenitor cells, and CD3+ T cells), thymus (CD4−CD8− double negative [DN], CD4+CD8+ double positive [DP], CD4CD8+ single positive [CD8 SP], CD4+CD8−CD25− [CD4 Tconv cells], and CD4+CD8−CD25+ [Treg], and spleen (CD8 T cells, CD4+CD25− Tconv cells, and CD4+ CD25+ Treg cells). Histograms represent mStrawberry expression within each lineage. Dotted line shows cutoff for "mStrawberry high" Panel C) Percentage of mStrawberry high cells in each hCD45+ lineage. N=10-14 mice per tissue analyzed. Data represent two independent experiments using different cord blood CD34+ donors. Panel D) Co-expression of FoxP3 and mStrawberry in humanized mice. Human CD4+ cells from engrafted NSG-SGM3 mice were sorted based on mStrawberry expression followed by intracellular staining and flow cytometric analysis for FoxP3 expression. Left panel shows sorting of human CD4+ cells by mStrawberry expression, while right panel shows FoxP3 expression within each sorted population.

FIG. 3 shows that the FoxP3 reporter vector shows Treg lineage specific expression in a humanized mouse model. CD34+ cells isolated from human cord blood were transduced with a FoxP3mStrawberry reporter vector and transplanted into neonatal immune-deficient NSG mice. 12 weeks post-transplant, engrafted hCD45+ cells were analyzed for mStrawberry expression. As shown in panel B, lineage specific mStrawberry expression in engrafted hCD45+ cells. hCD45+ cells were gated by lineage markers in NSG bone marrow (CD19+ B cells, CD33+ myeloid cells, CD34+ stem and progenitor cells, and CD3+ T cells), thymus (CD4−CD8− double negative [DN], CD4+CD8+ double positive [DP], CD4CD8+ single positive [CD8 SP], CD4+CD8−CD25− [CD4 Tconv cells], and CD4+CD8−CD25+ [Treg], and spleen (CD8 T cells, CD4+CD25− Tconv cells, and CD4+CD25+ Treg cells). The histograms represent mStrawberry expression within each lineage. Dotted line shows cutoff for "mStrawberry high" Panel shows the percentage of mStrawberry high cells in each hCD45+ lineage. The data represent two independent experiments using different cord blood CD34+ donors. Panel D shows co-expression of FoxP3 and mStrawberry in humanized mice. Human CD4+ cells from engrafted NSGSGM3 mice were sorted based on mStrawberry expression followed by intracellular staining and flow cytometric analysis for FoxP3 expression. The left panel shows sorting of human CD4+ cells by mStrawberry expression, while the right panel shows FoxP3 expression within each sorted population.

Figure 4:
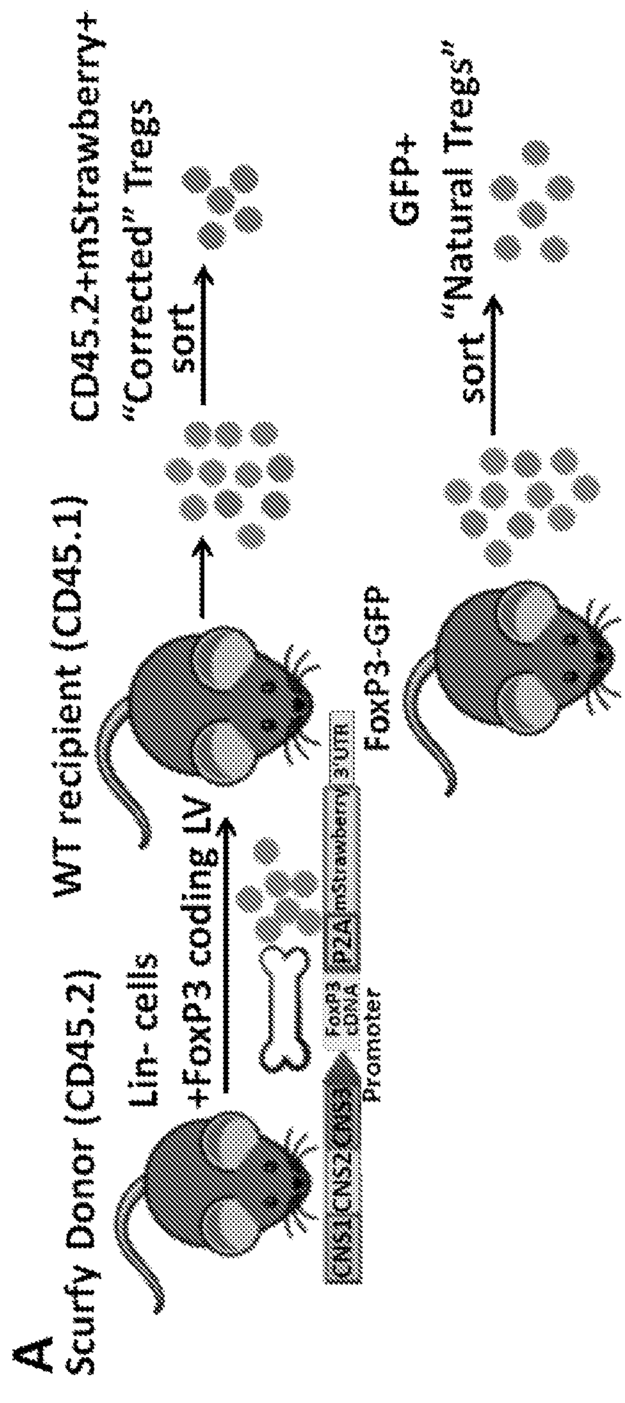
FIG. 4, panels A-C, shows that introduction of a lineage specific FoxP3 coding vector into FoxP3-deficient murine HSC restores functional Treg development. Panel A) Experimental set-up: Lin− cells were isolated from a FoxP3 deficient (scurfy) donor mouse and transduced with a FoxP3 coding vector expressing both FoxP3 cDNA and the reporter mStrawberry. Transduced lin− cells were transplanted in lethally irradiated WT CD45.1 congenic recipients. After 12 weeks, mStrawberry+ cells ("corrected Tregs") were evaluated for Treg suppressive capacity (panel B) and Treg surface marker expression (panel C). For each experiment, corrected Tregs from scurfy mice were compared to natural GFP+ Tregs from WT FoxP3−GFP mice. Panel B) Sorted Tregs (nTregs=natural GFP+ Tregs or cTregs=corrected mStrawberry Tregs) were co-cultured with Cell Trace Violet labeled CD4+FoxP3− responder cells in the presence of bead-bound CD3/CD28 antibodies. Tregs were cultured with Tresp cells in a 1:1 ratio. After 4 days in culture, Treg suppression was determined by calculating the division index of labeled responder cells in each group. Data represent mean+/−SEM from 1-2 replicate wells. Panel C) Thymocytes from WT FoxP3−GFP mice (top) or engrafted CD45.2 corrected donor scurfy cells (bottom). Right panel shows expression of Treg surface markers (CD25, GITR, and CTLA4) in each gated CD4 SP thymocyte population (GFP−, GFP+, mStrawberry−, or mStrawberry+).

FIG. 4 shows that introduction of a lineage specific FoxP3 coding vector into FoxP3-deficient murine HSC restores functional Treg development. Panel A shows the experimental set-up. Lin− cells were isolated from a FoxP3 deficient (scurfy) donor mouse and transduced with a FoxP3 coding vector expressing both FoxP3 cDNA and the reporter mStrawberry. Transduced lin− cells were transplanted in lethally irradiated WT CD45.1 congenic recipients. After 12 weeks, mStrawberry+ cells ("corrected Tregs") were evaluated for Treg suppressive capacity (panel B) and Treg surface marker expression (panel C). For each experiment, corrected Tregs from scurfy mice were compared to natural GFP+ Tregs from WT FoxP3–GFP mice. As shown in panel B, sorted Tregs (nTregs=natural GFP+ Tregs or cTregs=corrected mStrawberry Tregs) were co-cultured with Cell Trace Violet labeled CD4+FoxP3− responder cells in the presence of bead-bound CD3/CD28 antibodies. Tregs were cultured with Tresp cells in a 1:1 ratio. After 4 days in culture, Treg suppression was determined by calculating the division index of labeled responder cells in each group. Data represent mean+/− SEM from 1-2 replicate wells. Panel C) Thymocytes from WT FoxP3–GFP mice (top) or engrafted CD45.2 corrected donor scurfy cells (bottom). Right panel shows expression of Treg surface markers (CD25, GITR, and CTLA4) in each gated CD4 SP thymocyte population (GFP−, GFP+, mStrawberry−, or mStrawberry+).

Figure 5:
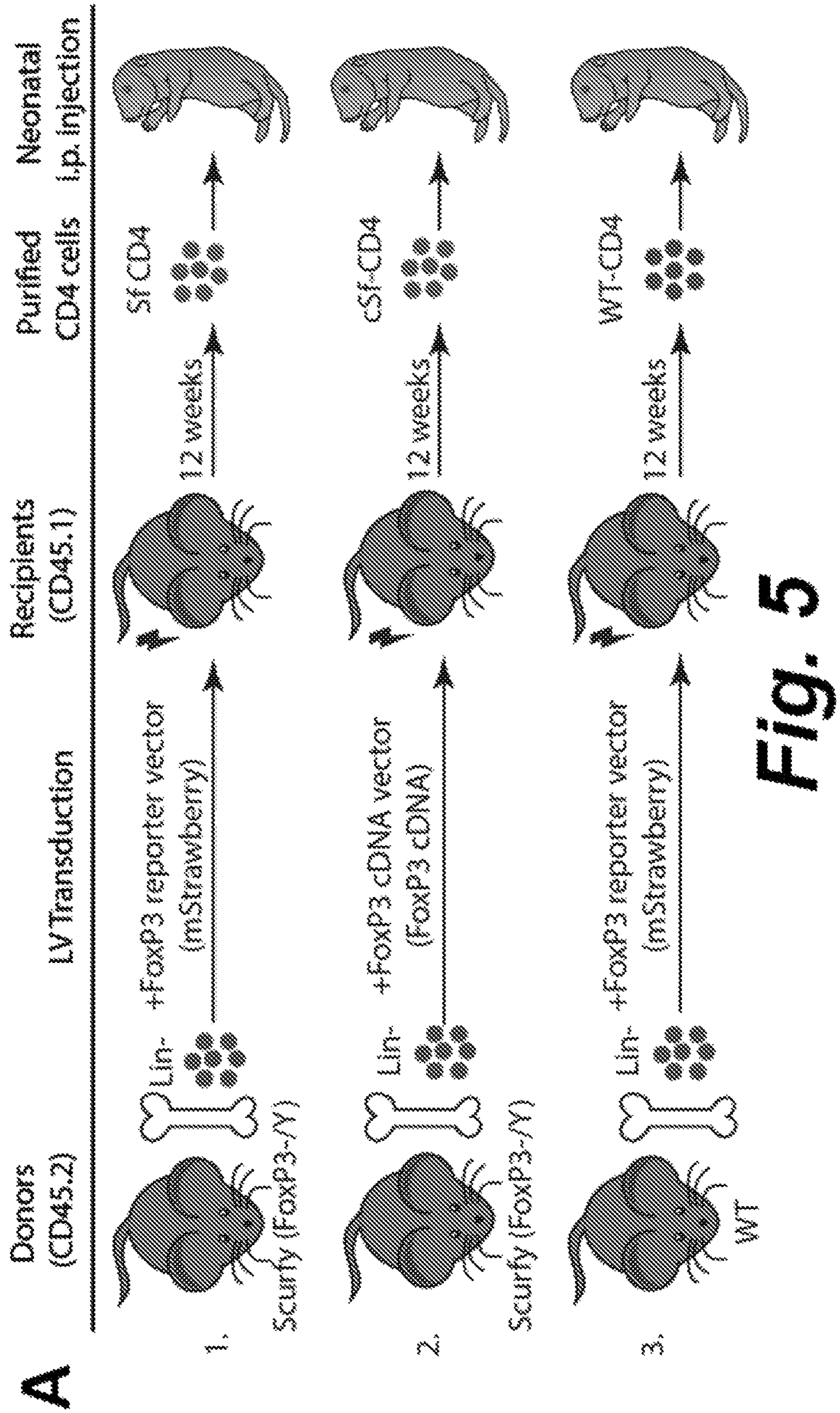
FIG. 5, panels A-E, shows that a lineage specific FoxP3 cDNA vector generates functional Tregs capable of rescuing the scurfy mouse (a FoxP3-deficient mouse model). Panel A) Experimental set up: Scurfy or WT HSPC (CD45.2) were transduced with either the FoxP3 reporter vector or FoxP3 cDNA vector and transplanted into lethally irradiated congenic (CD45.1) recipients. 12 weeks post-transplant, donor CD45.2+CD4+ cells (containing putative Tregs) were purified from the spleens of transplant recipients, and injected intrahepatically into scurfy neonates. Rescue of scurfy neonates was evaluated 21 days after transfer of CD4 T cells. Panel B) Splenic CD4 cells from rescued scurfy neonates at 21 d:Left plot shows a scurfy mouse that received Sf-Tregs (uncorrected) while right plot shows a scurfy mouse that received cSf-Tregs (corrected). Y-axis shows human FoxP3 expression (encoded by the FoxP3 LV) while x-axis shows murine FoxP3 expression (absent from both scurfy mice). Panel C) Spleen to body weight ratio for rescued scurfy mice or WT littermate controls. Panel D) Phenotype of splenic CD4 T cells in rescued scurfy neonates at 21 d. Red box highlights CD44+CD62L− (activated) CD4 T cells while blue box highlights CD44−CD62L+ (naïve) CD4 T cells. Panel E) Photographs of rescued scurfy neonates at 21d. White arrows highlight correction of car malformation

FIG. 5, panels A-E, shows that a lineage specific FoxP3 cDNA vector generates functional Tregs capable of rescuing the scurfy mouse (a FoxP3-deficient mouse model). Panel A) Experimental set up: Scurfy or WT HSPC (CD45.2) were transduced with either the FoxP3 reporter vector or FoxP3 cDNA vector and transplanted into lethally irradiated congenic (CD45.1) recipients. 12 weeks post-transplant, donor CD45.2+CD4+ cells (containing putative Tregs) were purified from the spleens of transplant recipients, and injected intrahepatically into scurfy neonates. Rescue of scurfy neonates was evaluated 21 days after transfer of CD4 T cells. Panel B) Splenic CD4 cells from rescued scurfy neonates at 21 d. :Left plot shows a scurfy mouse that received Sf-Tregs (uncorrected) while right plot shows a scurfy mouse that received cSf-Tregs (corrected). Y-axis shows human FoxP3 expression (encoded by the FoxP3 LV) while x-axis shows murine FoxP3 expression (absent from both scurfy mice). Panel C) Spleen to body weight ratio for rescued scurfy mice or WT littermate controls. Panel D) Phenotype of splenic CD4 T cells in rescued scurfy neonates at 21 d. Red box highlights CD44+CD62L− (activated) CD4 T cells while blue box highlights CD44−CD62L+ (naïve) CD4 T cells. Panel E) Photographs of rescued scurfy neonates at 21 d. White arrows highlight correction of car malformation.

Example 2

Hematopoietic Stem Cell Gene Therapy for IPEX Syndrome

Immune dysregulation, Polyendocrinopathy, Enteropathy, X-linked (IPEX) syndrome is a devastating autoimmune disease caused by mutations in FOXP3, a lineage-determining transcription factor required for the development and function of regulatory T cells (Tregs). Tregs are critical for suppressing autoreactive T cell responses, thus their dysfunction in IPEX patients leads to severe autoimmunity. Allogeneic hematopoietic stem cell (HSC) transplant can be curative, but suitable donors are often unavailable. Here, we demonstrate a strategy for autologous HSC transplant and gene therapy utilizing a lentiviral vector (LV) to restore developmentally appropriate FoxP3 expression under the control of endogenous regulatory elements. Both murine congenic transplant models and humanized mice engrafted with LV-modified HSC show high levels of LV expression restricted to CD4+CD25+FoxP3+ Tregs. LV transduction of scurfy (FoxP3null) HSC restores development of functional FoxP3+ Tregs that suppress T cell proliferation in vitro and rescue the scurfy autoimmune phenotype in vivo. These findings pave the way for the treatment of IPEX patients by autologous HSC transplant and may provide valuable insights into new treatments for patients with autoimmune disorders of different origin.

More specifically, here, we describe the development of a LV regulated by human FOXP3 genetic elements that recapitulates physiologic FoxP3 expression. Introduction of this vector into murine and human HSPC results in Treg-restricted expression and restores functional Treg development from FoxP3-deficient HSPC. We demonstrate that this strategy generates suppressive FoxP3+ Tregs, capable of curing the autoimmune phenotype of the scurfy mouse (a FoxP3null mouse model of IPEX). Additionally, humanized mouse models engrafted with LV-modified human HSPC from healthy donors show high levels of Treg-specific LV expression, suggesting that this approach may be similarly efficacious in human IPEX patients.

Results

Ectopic FoxP3 Expression from a Constitutively Active Promotor Impairs HSPC Function Many successful LV-based gene therapies to date have utilized constitutively active promoters to drive high levels of expression of a therapeutic protein. To determine if constitutive FoxP3 expression is a suitable strategy for IPEX HSPC gene therapy, we first set out to determine the effect of ectopic FoxP3 expression on HSPC engraftment and function. Here, we utilized a LV that expresses high levels of FoxP3 (MNDU3-FoxP3-IRES-GFP) and compared its effects to a control vector (MNDU3-GFP). Murine lin− cells transduced with MNDU3-FoxP3-IRES-GFP showed successful LV transduction and expression (~30% GFP+ cells) with no discernable effects on viability (FIG. 8, panel A). When LV-modified cells were transplanted into mice, circulating CD45.1+ (donor) GFP+ cells were readily detected in peripheral blood at 7 days post-transplant (FIG. 8, panel B), suggesting that cells were capable of early engraftment. However, the early post-transplant period (10-21 days) was marked by a rapid decline of red blood cell counts, and failure to reconstitute white blood cell and platelet counts (FIG. 8, panel C), and led to a 60% mortality rate in mice receiving HSPC modified with MNDU3-FoxP3-IRES-GFP (FIG. 8, panel D). To determine the effects of constitutive FoxP3 expression on human HSPC, NSG neonates were humanized with cord blood CD34+ HSPC transduced with MNDU3-GFP or MNDU3-FoxP3-IRES-GFP. While no cell death was observed in GFP+ cells 3 days post transduction (FIG. 8, panel E), NSG engraftment of hCD45+ cells in the peripheral blood was significantly impaired in mice receiving HSPC transduced with MNDU3-FoxP3-IRES-GFP (FIG. 8, panel F). Collectively, these results suggest that ectopic expression of FoxP3 in HSPC negatively affects hematopoiesis.

Development of a Lineage Specific Lentiviral Vector for FoxP3 Expression

Figure 9A:
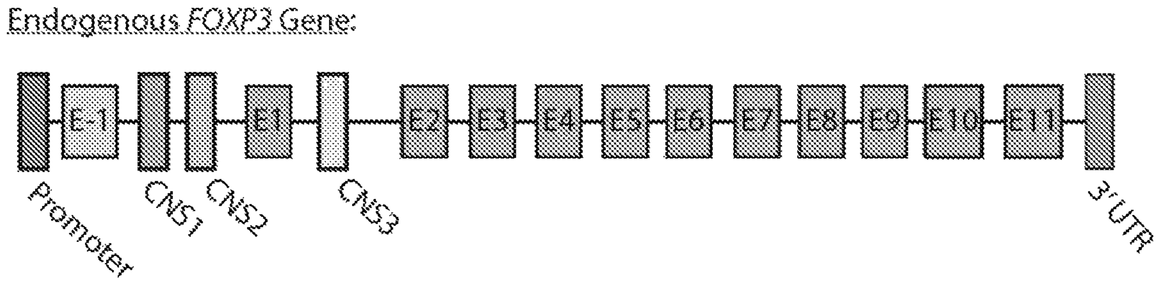
FIGS. 9A and 9B, illustrate the design of a Lentiviral Vector for lineage specific FoxP3 expression.
Figure 9B:
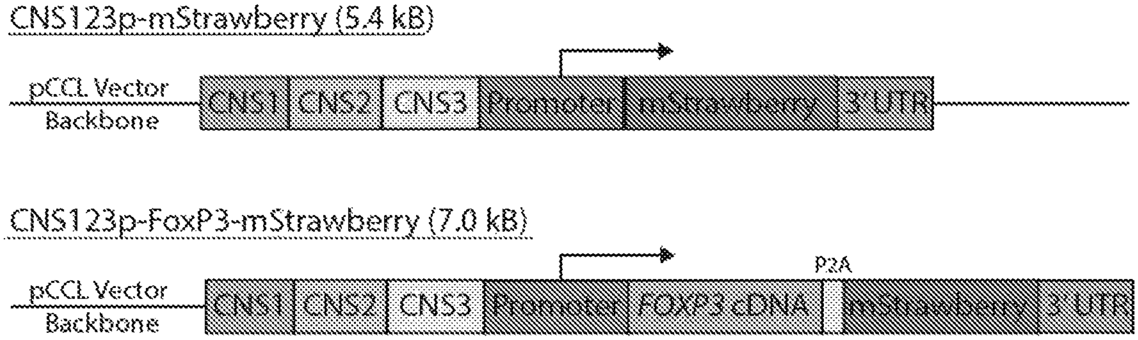

Due to our observations of impaired hematopoiesis with ectopic FoxP3 expression, we sought to design a LV which would confer developmentally appropriate FoxP3 expression. A major challenge to accomplish this task is including key FOXP3 regulatory elements without exceeding a LV genome size of 8-10 kb, above which LV exhibit poor titers and transduction efficiency. To recapitulate endogenous FoxP3 expression, we utilized three previously characterized conserved regulatory regions within the FOXP3 gene: conserved noncoding sequence (CNS) 1, CNS2, and CNS3 (FIG. 9A). The three CNS elements were added upstream from the FOXP3 promoter, and the FOXP3 3'UTR was added after the expression cassette (FIG. 9B). This construct was cloned into a VSV-G-pseudotyped, 3rd-generation, self-inactivating (SIN) LV (Dull et al. 1998) with the addition of a previously described enhancer blocking insulator element ("A2") in the viral 3' LTR regions potentially to improve safety and decrease positional variegation of expression (Liu et al. 2015). Two LV were designed using this construct to drive the expression of the fluorescent reporter mStrawberry only (hereby referred to as "CNS123p−mStrawberry"), or the FOXP3 cDNA and mStrawberry through a 2A element linkage ("CNS123p-FoxP3−mStrawberry").

Figure 10:
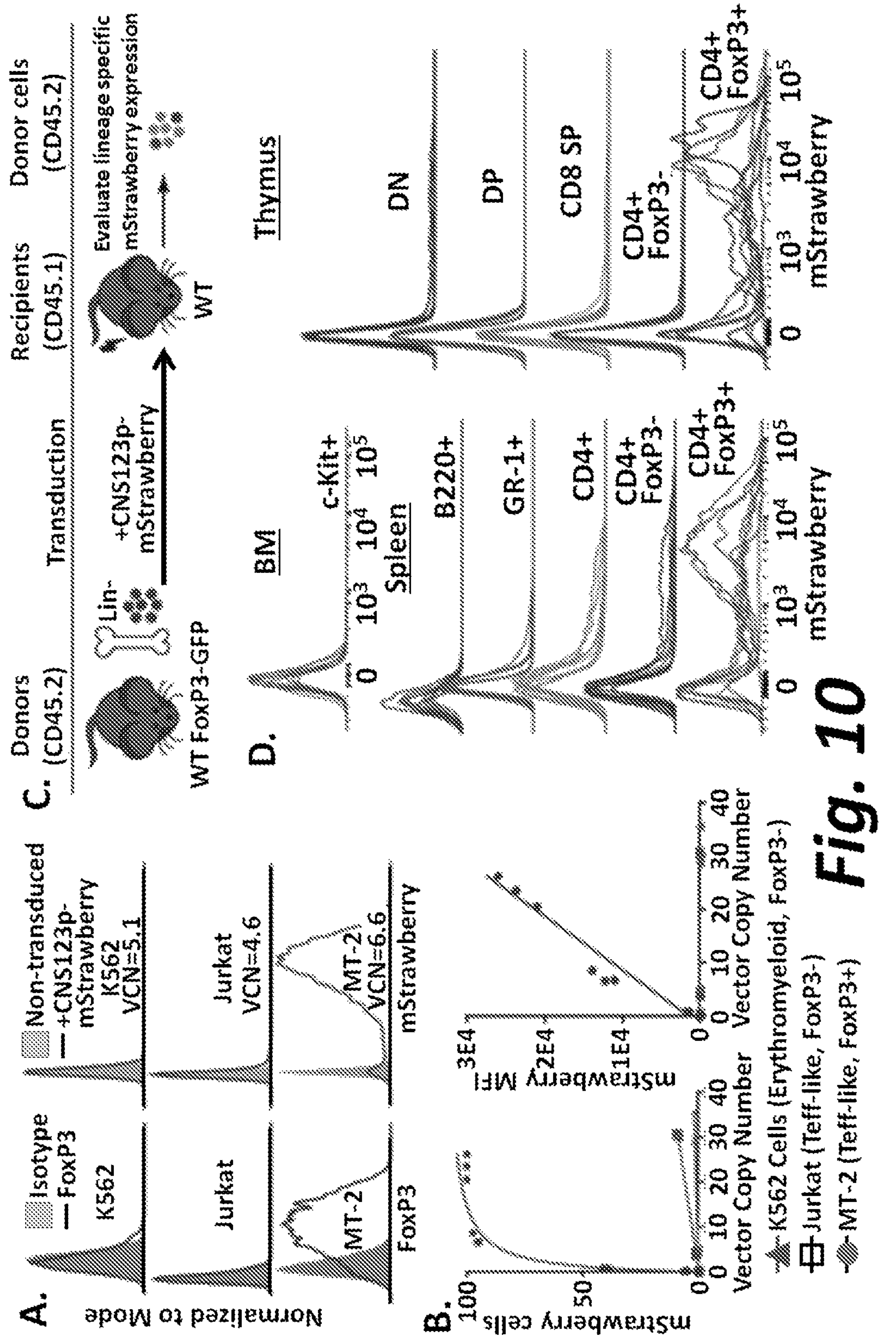
FIG. 10, panels A-E. The FoxP3 reporter LV shows Treg lineage specific expression. Panel A) Analysis of human hematopoietic cell lines transduced with CNS123p−mStrawberry. Histograms in the left panel show endogenous FoxP3 status of each cell line. Histograms in the right panel show mStrawberry expression in each cell line transduced with CNS123p−mStrawberry. Panel B) mStrawberry expression in human hematopoietic cell lines over a range of vector copy numbers. Y-axis represents the percentage of cells positive for mStrawberry expression (left) or mean intensity of mStrawberry fluorescence (right), while x-axis represents the number of vector copies per cell, (n=12 per cell line). Panel C) Experimental design to evaluate in vivo lineage-specific expression of CNS123p−mStrawberry. CD45.2 FoxP3−GFP transgenic mice (which co-express FoxP3 and GFP) were used as bone marrow donors. Lin− HSPC were isolated from CD45.2 FoxP3−GFP mice and transduced with CNS123p−mStrawberry. Transduced lin− HSPC were transplanted into lethally irradiated congenic CD45.1 recipients. CD45.2 donor cells within each hematopoietic lineage were analyzed at 20 weeks post-transplant for mStrawberry reporter vector expression. Panel D) Histograms depict mStrawberry reporter expression in each hematopoietic lineage in bone marrow, thymus, and spleen of engrafted mice. Each individual histogram line represents mStrawberry expression in the specified lineage for an individual mouse (n=9 mice). Panel E) Y axis represents the percentage of mStrawberry+ cells within each hematopoietic lineage in the BM, spleen, and thymus (n=9 mice). Data in panel E represent mean±SD.
Figure 10:
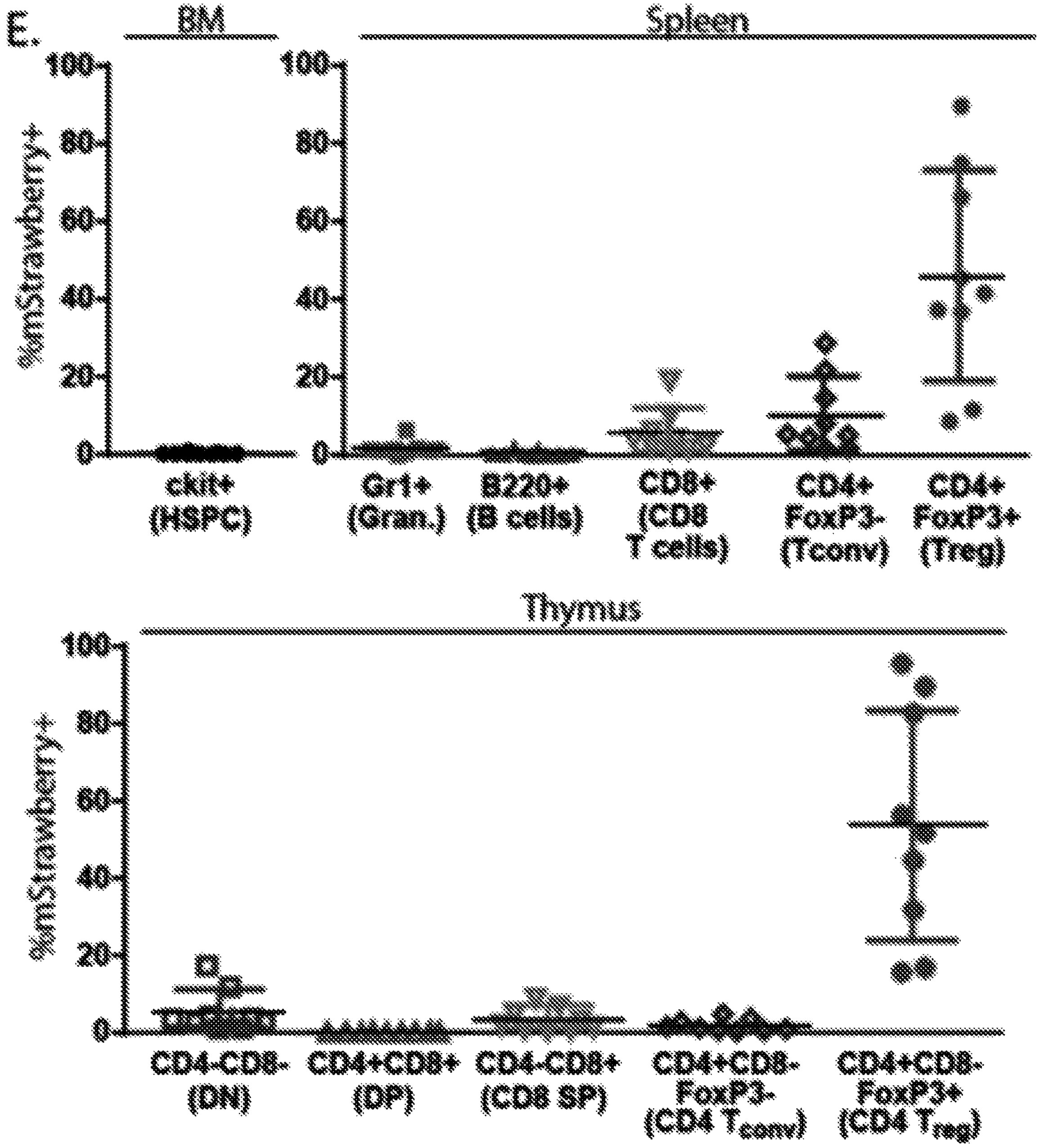

The endogenously regulated LV CNS123p−mStrawberry shows high specificity for the Treg lineage We first evaluated the specificity of the CNS123p−mStrawberry reporter LV in human cell lines from different hematopoietic lineages (K562 [erythromyeloid, FoxP3-], Jurkat [Tconv-like, FoxP3-] and MT-2 [Treg-like, FoxP3+], FIG. 10, panel A). Analysis of transduced cells by flow cytometry revealed mStrawberry expression restricted to the FoxP3+ MT-2 cells with low inherent "leakiness" of expression in FoxP3− cell types, even at very high vector copy numbers (up to ~25 copies/cell) (FIG. 10, panel B). In MT-2 cells which normally express high levels of FoxP3, the mean fluorescence intensity (MFI) of mStrawberry increased linearly with increasing copy numbers (FIG. 10, panel B). These results suggest that the CNS123p elements confer highly specific gene expression in FoxP3+ cells and lack basal expression in inappropriate cell types.

In order to evaluate in vivo lineage specificity of the CNS123p−mStrawberry reporter LV, we used a murine congenic transplant system to evaluate LV expression in transduced HSPC and their progeny throughout hematopoietic development. Here, we transduced CD45.2 lineage-marker-negative (lin−) HSPC from the bone marrow of FoxP3−GFP reporter mice (which co-express FoxP3 and GFP) with CNS123p−mStrawberry and transplanted the modified cells into congenic CD45.1 recipients (FIG. 10, panel C). 20 weeks post-transplant, mStrawberry expression was evaluated in hematopoietic lineages of donor CD45.2 cells (lineage gating shown in FIG. 14). Here, we observed that mStrawberry expression from CNS123p−mStrawberry closely matched GFP expression from the endogenous FOXP3 gene. mStrawberry expression was restricted to the Treg lineage (CD4+GFP+), with negligible mStrawberry expression in cKit+ HSPC, B220+ B cells, Gr1+ granulocytes, CD8+ T cells, and CD4+GFP− Tconv cells (FIG. 9, panels D and E). These results suggest that expression of CNS123p−mStrawberry is highly concordant with endogenous FoxP3 expression throughout hematopoietic development.

Figure 11:
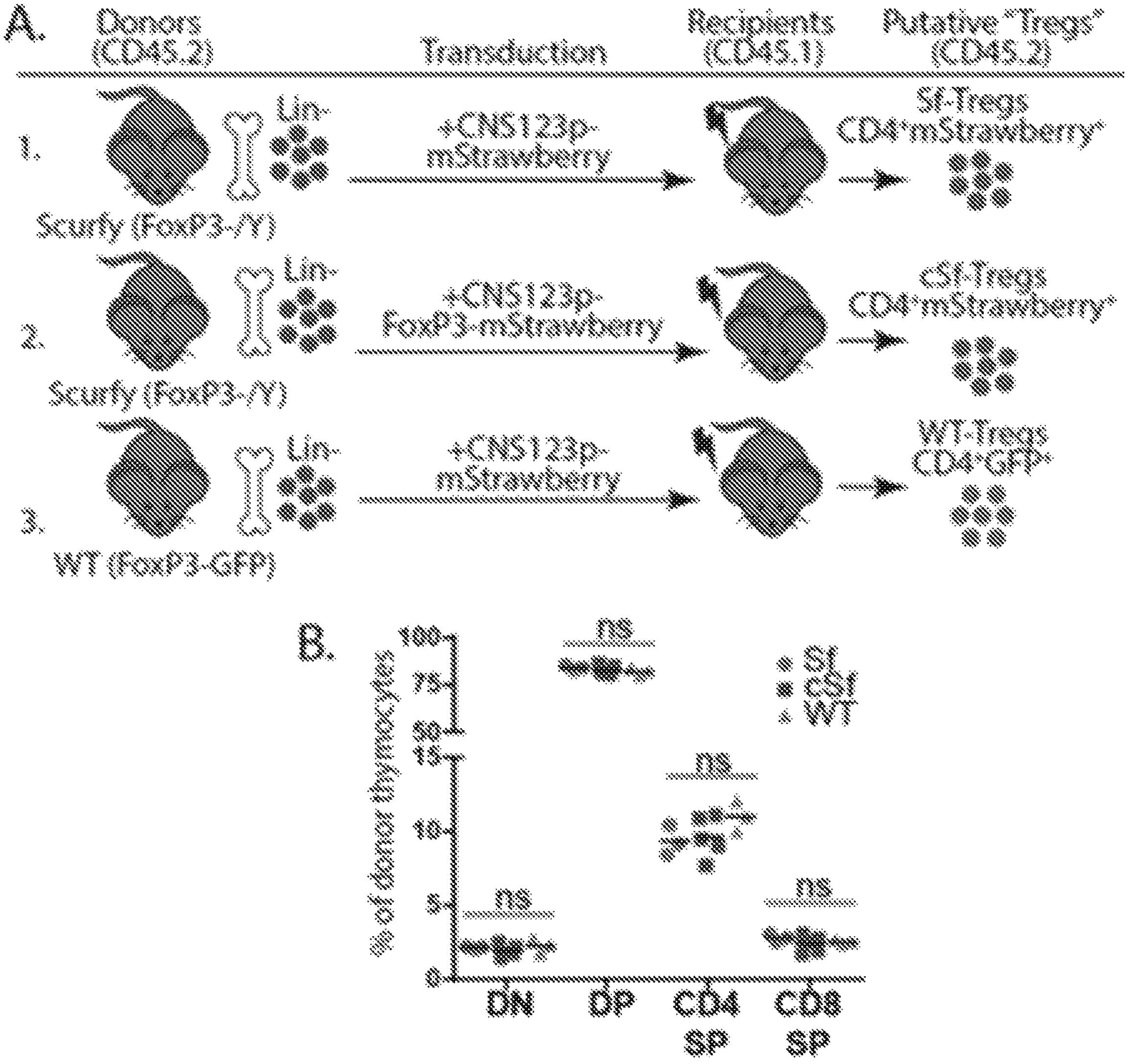
FIG. 11, panels A-F. Lineage-specific FoxP3 expression restores Treg development from scurfy (FoxP3-deficient) HSC. Panel A) Transplant set-up to evaluate Treg development: Lin− HSPC were isolated from FoxP3-deficient (scurfy) or wild-type (FoxP3−GFP) donor mice and transduced with CNS123p−mStrawberry or CNS123p-FoxP3−mStrawberry. Transduced lin− HSPC were transplanted into lethally irradiated WT CD45.1 congenic recipients. After 12 weeks, donor cells from each transplant cohort were evaluated for thymic and splenic reconstitution of Tregs. Treg populations from each group were identified as CD4+ mStrawberry+ cells (Uncorrected scurfy Tregs [Sf-Tregs], corrected scurfy Tregs [cSf-Tregs]) or CD4+GFP+ cells (Wild-type Tregs [WT-Tregs]). Panel B) Lineage distribution of total donor thymocytes in mice reconstituted with Sf, cSf, or WT BM lin− cells. (n=3-5 micc/arm). Panel C) Thymic Treg reconstitution. FACS plots show donor CD45.2+CD4SP cells in the thymus of transplant recipients. Gates delineate thymic Sf-Tregs, cSf-Tregs, and WT-Tregs. Bottom panel shows expression of the Treg surface markers CD25, GITR, and CTLA4 within each putative Treg population. For surface marker expression, Sf-Tregs and cSf-Tregs are defined by cells expressing the top 50% of mStrawberry expression. Histograms depict one representative experiment of 3. Panel D) Splenic Treg and Tconv sort. Splenic Treg populations (mStrawberry+ or GFP+ gates) were FACS sorted for a Treg suppression assay. Tconv populations (mStrawberry− or GFP− gates) were sorted for an iTreg induction assay. Panel E) In vitro Treg suppression assay. Sorted Tregs (shown in Panel D) were co-cultured with responder T cells (Tresp, congenic WT CD4+ cells labeled with a fluorescent proliferation dye) at a 1:1 ratio in the presence of bead-bound CD3/CD28 antibodies. After 3 days in culture, Tresp proliferation was determined by dilution of proliferation dye by flow cytometry. Histograms depict Tresp proliferation in one of three representative experiments. Bar graph shows proliferation index for each Treg culture condition (n=6-9 per arm, from 3 different Treg sources per arm, data normalized to internal "no Treg" control for each experiment). Panel F) Sorted splenic Tconv cells (shown in panel D) were activated with CD3/CD28 antibodies in the presence of 20 ng/mL IL-2 and 20 ng/mL TGFβ for 4 days to induce iTregs. FACS plots show mStrawberry or GFP expression from each group (n=3 mice/group). Data in panels B, C, E, and F are presented as mean±SD. Data in panel B were analyzed by Kruskal Wallis test for each lineage. Data in panel E are analyzed by Kruskal Wallis test for overall comparison for all groups, and Mann-Whitney U test for pairwise comparisons. *$p<0.05$, $p<0.01$, *$p<0.001$ NS, not significant.

LV correction of FoxP3-deficient HSC from the scurfy mouse generates functional Tregs with suppressive function We next determined if the CNS123p-FoxP3−mStrawberry LV could enable functional Treg development through restoration of physiologic FoxP3 expression in scurfy (FoxP3-deficient) HSC. Scurfy mice harbor a frameshift mutation in the forkhead region of FOXP3 and produce non-functional (FoxP3−) Tregs incapable of suppressing autoimmune responses. In the absence of treatment, scurfy mice succumb to a fatal lymphoproliferative disorder starting ~21 days after birth. Thus, in order to obtain sufficient numbers of scurfy HSC, neonatal scurfy mice (CD45.2) were rescued at birth by injection of WT splenocytes (CD45.1) to allow survival into adulthood. To assess restoration of functional Treg development, we transplanted WT CD45.1 recipients with one of three different sources of CD45.2 HSPC: (1) Scurfy lin− cells transduced with CNS123p−mStrawberry, (2) scurfy lin− cells transduced with CNS123p-FoxP3−mStrawberry, and (3) WT FoxP3−GFP lin− cells transduced with CNS123p−mStrawberry (FIG. 11, panel A).

Prior work has shown that overexpression of FoxP3 under the lck proximal (thymocyte specific) promoter can drastically alter thymopoiesis (Khattri et al. 2001), thus we first assessed if the lineage-specific CNS123p-FoxP3−mStrawberry LV altered thymocyte differentiation. Here, we observed that lineage distribution within reconstituted donor thymocytes did not differ among recipient mice transplanted with WT, scurfy, or corrected scurfy HSC (FIG. 11, panel B) suggesting that lineage specific restoration of FoxP3 cDNA does not alter thymocyte lineage distribution.

We next evaluated the frequency of corrected scurfy Tregs (cSf-Tregs) in recipient thymuses. Transplant recipients reconstituted with WT FoxP3–GFP HSC showed 3.7±0.6% (mean±SD) GFP+ cells within the CD4 single positive (CD4 SP) population, while recipients reconstituted with LV-corrected scurfy HSC showed 2.1±0.4% mStrawberry+ cells, confirming that corrected scurfy HSPC produced CD4 SP thymocytes which express FoxP3 (FIG. 11, panel C). GFP+ or mStrawberry+ donor thymocytes were further evaluated for the expression of Treg surface markers. Uncorrected (FoxP3–) Sf-Tregs in the thymus showed reduced expression of the Treg surface markers CD25 and GITR compared to WT-Tregs (FIG. 11, panel C). In contrast cSf-Tregs with the highest level of LV expression (mStrawberryhigh) showed CD25 and GITR expression comparable to WT-Tregs, suggesting that expression of FoxP3 from CNS123p-FoxP3–mStrawberry restores phenotypic Treg development in the thymus.

We next characterized the suppressive function of splenic cSf-Tregs. Three groups of putative Tregs (Sf-Tregs, cSf-Tregs, and WT-Tregs) were FACS sorted from the spleens of transplant recipients (FIG. 11, panel D) and evaluated for their capacity to suppress WT CD4 T cell proliferation at a 1:1 suppressor to effector ratio (FIG. 11, panel E). As expected, uncorrected (FoxP3–) Sf-Tregs failed to suppress T cell proliferation relative to control (no Tregs). However, cSf-Tregs showed significant suppressive capacity on par with that of WT-Tregs, confirming that CNS123p-FoxP3–mStrawberry generates corrected Tregs with functional capacity.

In addition to thymically-derived Tregs (nTregs), FoxP3 also plays an important role in the generation of peripheral Tregs (pTregs) which develop when Tconv receive a strong TCR signal in a tolerogenic context (Curotto de Lafaille et al. 2004). This process can be simulated in vitro through TCR stimulation of FoxP3– Tconv cells in the presence of TGFβ to generate FoxP3+ induced Tregs (iTregs) with suppressive function (Chen et al. 2003). To determine if corrected scurfy CD4 Tconv cells were capable of generating iTregs, cSf Tconv (CD4+mStrawberry–) cells or WT Tconv (CD4+GFP–) cells were FACS sorted and activated using CD3/CD28 beads in the presence of TGFβ. Four days after activation with TGFβ, cSf Tconv showed robust induction of mStrawberry (FIG. 11, panel F) demonstrating that corrected Sf-Tconv cells are capable of de novo FoxP3 induction. Collectively, our data suggest that LV correction of scurfy HSC promotes physiologic restoration of a functional Treg compartment.

The lineage-specific FoxP3 LV (CNS123p-FoxP3–mStrawberry) generates Tregs capable of rescuing scurfy mice The most stringent test of Treg function is the ability to reverse clinical disease signs in neonatal scurfy mice through in vivo suppression of autoimmunity. To this end, we first attempted to transplant neonatal scurfy mice with LV-corrected lin– HSPC. Neonatal scurfy mice were conditioned with 500 Rad total body irradiation (TBI) and injected i.p with either WT HSPC, uncorrected Sf HSPC, or corrected Sf HSPC. Long-term survival was poor in all arms despite detectable (albeit low) engraftment of donor cells, suggesting low efficacy of purified HSPC transplant in the scurfy model (FIG. 15).

We speculated that poor survival in scurfy mice transplanted with WT HSPC (a positive control for FoxP3-sufficient HSPC) may be due to the rapid onset of irreversible multi-organ autoimmune damage which occurs long before HSPC can generate mature Tregs to control the autoimmune response in this model system. We therefore pursued an alternative approach in which mature Tregs were generated by HSPC transplantation into WT recipient mice and subsequently purified for adoptive transfer to scurfy neonates. Scurfy or WT HSPC (lin–CD45.2+) were transduced with CNS123p–mStrawberry or CNS123p-FoxP3–mstrawberry LV and transplanted into congenic WT recipients (CD45.1). 8 weeks after transplant, donor CD45.2+ CD4+ cells were purified from spleens of transplant recipient to obtain three groups of bulk CD4+ cells containing putative Tregs: uncorrected scurfy CD4+ (Sf–CD4+), corrected scurfy CD4+ (cSf-CD4+), or wild-type CD4+ (WT-CD4+) (FIG. 12, panel A). FACS analysis of purified CD45.2+CD4+ cells prior to transfer showed ~95% CD4+ purity with no detectable contaminating recipient CD45.1 cells (FIG. 16).

Purified CD45.2+CD4+ cells representing 8.6×105–2.1×106 putative Tregs (GFP+ or mStrawberry+, FIG. 16) were intraperitoneally injected into scurfy neonates. At 21 days of age, scurfy mice were analyzed for correction of the autoimmune phenotype. 21 d old untreated (sham PBS injection) scurfy neonates showed typical phenotypic signs of disease progression including scaly skin, small thickened ears (FIG. 12, panel B), and splenomegaly (FIG. 12, panel C). Untreated mice also exhibited an inflammatory immune phenotype including a high percentage of activated CD62L–CD44+ CD4 T cells (FIG. 12, panel D) and elevated levels of inflammatory serum cytokines (FIG. 12, panel E) compared to age-matched WT controls. Administration of WT-CD4 and cSf-CD4 cells containing >3 VC per cell resulted in complete correction of all measures of the scurfy phenotype such that these mice were phenotypically indistinguishable from age-matched WT controls. In contrast, scurfy mice receiving uncorrected Sf–CD4 cells showed no signs of disease amelioration confirming that the BMT and CD4 purification procedure did not carry over any contaminating CD45.1 WT Tregs from transplant recipients. Furthermore, scurfy mice receiving cSf Tregs with VCN <2 showed incomplete correction of the scurfy phenotype (FIG. 16), suggesting that high levels gene modification are required to generate Tregs with in vivo suppressive capacity in this model. Collectively, these results demonstrate that LV correction of FoxP3-deficient HSC generates CD4+ Tregs capable of suppressing autoimmune responses in vivo.

The CNS123p–mStrawberry LV shows high levels of lineage specific expression without toxicity in a humanized mouse model In order to evaluate the applicability of this therapy to IPEX patients, we next explored the expression patterns of the CNS123p–mStrawberry reporter LV in a humanized xenograft model. Healthy human CD34+ HSPC isolated from cord blood were transduced with CNS123p–mStrawberry and transplanted into NSG neonates (FIG. 13, panel A). Engrafted hCD45+ cells were analyzed at 12-16 weeks post-transplant. The mean+SD number of vector copies per engrafted human cell in the NSG BM was 4.1±2.5, suggesting efficient modification of LT-HSC with the LV. Human CD45+ cells engrafted in the BM exhibited a lineage distribution typical of this model system (59% CD19+ B cells, 10% CD33+ myeloid cells, 2.5% CD34+ HSPC, 3.3% CD3+ T cells, FIG. 17) indicating the absence of subclinical graft versus host disease and potential artifacts from T cell activation.

Cells were analyzed by flow cytometry to determine mStrawberry expression from CNS123p−mStrawberry in each hematopoietic lineage (FIG. 13, panels B and C). In BM, mStrawberry expression was restricted to CD3+ T cells, with no detectable expression in CD33+ myeloid, CD19+ B cells, or CD34+ HSPC lineages. In the thymus, mStrawberry expression was selective for CD4+CD25+ Tregs (mean 36% mStrawberry+) with minimal expression in the DN, DP, CD4SP, or CD8SP stages. In the spleen, mStrawberry expression was highest in CD4+CD25+ Tregs (46% mStrawberry+), with lower levels of expression observed in CD4+CD25−Tconv cells (17% mStrawberry+) and CD8+ T cells (4% mStrawberry+). For each mouse analyzed, the intensity of mStrawberry fluorescence was greatest in the CD4+CD25+ Treg subset (FIG. 13, panel B).

While CD25 is a useful surface marker that identifies FoxP3+ Tregs, CD25 is also expressed on activated T cells and is not specific for FoxP3+ Tregs. Therefore, we more stringently determined the Treg lineage specificity of CNS123p−mStrawberry with intracellular FoxP3 staining. Here, we utilized NSG-SGM3 mice, which generate enhanced numbers of FoxP3+ Tregs compared to traditional NSG models (Billerbeck et al. 2011). Human cord blood CD34+ HSPC were transduced with CNS123p−mStrawberry and transplanted into NSG-SGM3 neonates. 12 weeks after transplant, human CD4+ cells were isolated from the spleen and FACS-sorted into mStrawberry+ and mStrawberry− populations prior to FoxP3 staining (FIG. 13, panel D). We observed that 81% of mStrawberry+ cells were also FoxP3+, while only 2.5% of mStrawberry− cells were FoxP3+, suggesting high concordance of CNS123p−mStrawberry expression and endogenous FoxP3 expression in a humanized mouse model.

Our prior studies investigating constitutive FoxP3 expression from the MNDU3 promoter suggested that aberrant FoxP3 expression in HSC is detrimental to engraftment. We therefore sought to confirm that our lineage-specific expression strategy using CNS123p-FoxP3−mStrawberry (which does not express in HSPC) allows for efficient HSC engraftment in a competitive transplant model. CD34+ "test cells" were transduced with either CNS123p−mStrawberry or CNS123p-FoxP3−mStrawberry, combined with an equal number of fluorescently labeled (UBC-mCitrine transduced) competitor cells, and transplanted into neonatal NSG mice (FIG. 13, panel E). At 12 weeks post-transplant, the relative contribution of fluorescently labeled competitor cells was evaluated within the CD34+ lineage. Here, we observed no difference in the relative proportions of competitor cells between groups. This suggests that unlike constitutive FoxP3 expression from MNDU3-FoxP3, lineage-specific FoxP3 expression from CNS123p-FoxP3−mStrawberry shows no detrimental effects on HSC engraftment.

We next evaluated the role that CNS2 methylation plays in regulating LV expression. During thymopoiesis, active demethylation of the CNS2 region is a critical event that induces heritable commitment to the Treg lineage (Toker et al. 2013). Demethylated CNS2 maintains stable high levels of FoxP3 expression through its enhancer function on the FoxP3 promoter (Zheng et al. 2010; Li et al. 2014a), thus we were interested in evaluating CpG methylation patterns within the viral CNS2 element contained within CNS123p-FoxP3−mStrawberry. Here, we isolated spleens from NSG mice reconstituted with LV-transduced CD34+ CB cells and sorted pooled splenocytes for Tconv cells (CD4+CD25−) and Tregs (CD4+CD25+) (FIG. 13, panel F). Genomic DNA from Tconv and Treg subsets was analyzed for methylation of 9 regulated CpG sites present in endogenous and viral CNS2 utilizing pyrosequencing primers specific for each sequence. As expected, CpG sites within the endogenous FOXP3 CNS2 were methylated in sorted Tconv cells and demethylated in sorted Tregs. Interestingly, viral CNS2 remained fully demethylated in both populations, suggesting that viral CNS2 is not regulated in the same manner as endogenous CNS2 during Treg differentiation from HSC.

Discussion

Since the genetic characterization of FoxP3 as the causative gene with mutations for IPEX and scurfy in 2001 (Wildin et al. 2001b; Bennett et al. 2001), a large body of work has further elucidated a key role for FoxP3+ Tregs in maintaining immunologic tolerance. The severe autoimmunity stemming from a complete absence of Tregs makes IPEX a highly informative disease to broaden our understanding of human Treg development and the mechanisms of immunologic tolerance.

Recent developments resulting in efficient viral gene transfer to HSC with an improved safety profile have greatly expanded the reach of the field of gene therapy resulting in efficacious Phase I/II clinical trials for a wide range of genetic blood disorders (Morgan et al. 2017). Given the recent successes of this approach, we sought to develop a LV-based therapy to treat IPEX which could restore physiologic FoxP3 expression within the developing hematopoietic system, resulting in the development of functional Tregs and resolution of autoimmunity.

FoxP3 is a transcription factor which plays a key role in cell fate decisions, thus we speculated that inappropriate FoxP3 expression throughout the hematopoietic system could be detrimental to normal hematopoietic development and long-term engraftment. Indeed, we observed that constitutive FoxP3 expression driven by the constitutive MNDU3 promoter resulted in impaired long-term engraftment in human and murine HSPC transplant models. This observation is consistent with prior work showing that high levels of FoxP3 expression under strong thymic promoters results in abnormal thymopoiesis and increased apoptosis in developing thymocytes (Khattri et al. 2001; Tai et al. 2013). Interestingly, Santoni de Sio et al. observed enhanced HSC engraftment but abnormal T cell development from cord blood HSPC transduced with a LV expressing FoxP3 under the constitutively active EF1a promoter (Santoni de Sio et al. 2017). These conflicting results may suggest that different levels of constitutive FoxP3 expression (driven by the relative strengths of the EF1a vs. MNDU3 promoters) can have differential effects on HSC biology. Collectively, our and others' findings suggest that an ideal HSC-based gene therapy for IPEX syndrome should avoid aberrant and ubiquitous FoxP3 expression.

In order to avoid deleterious effects of aberrant FoxP3 expression, we designed a LV using endogenous elements of the human FOXP3 gene to confer developmentally appropriate FoxP3 expression. One of the major challenges in designing a lineage-specific LV is retaining endogenous FOXP3 enhancer elements capable of promoting high cDNA expression levels while simultaneously maintaining a compact LV genome. Large LV genomes typically exhibit reduced titers and decreased transduction efficiency (Kumar et al. 2001; Canté-Barrett et al. 2016), thus making it difficult to achieve therapeutic correction of HSC. This has been readily apparent in clinical efforts to treat hemoglobinopathies using LV containing large enhancer elements from the Locus Control Region (LCR) to drive erythroid-specific expression of the human β-globin gene (Cavazzana-Calvo et al. 2010). Here, we designed a 7.0 kb lineage-specific LV that exhibits high titers (raw titer for the FoxP3 cDNA vector was 2.25×106), is capable of achieving high copy numbers in murine and human HSC and shows therapeutic levels of FoxP3 expression within the Treg lineage. All of these factors suggest favorable clinical translation for the treatment of IPEX patients.

In order to design a LV with Treg-specific expression, we utilized information contained in the ENCODE data base to identify regions of Treg-specific DNAse hypersensitivity in FOXP3 and identified CNS1, CNS2, and CNS3 as important Treg-specific enhancer regions. The three CNS regions are highly conserved and have previously been well characterized with mouse models demonstrating the effect of genetic ablation of each region on FoxP3 expression and Treg development (Zheng et al. 2010). CNS3 has been characterized as the "pioneer element" and is critical for the initial induction of FoxP3 expression during thymocyte Treg development. CNS1 is considered to be a TGFβ responsive element with a number of Smad binding sites, and is critical for the induction of pTregs. CNS2 is responsible for maintaining stable FoxP3 expression in committed Tregs (Li et al. 2014). Recent evidence has suggested that demethylation of CNS2 is an active process initiated by Tet enzymes during thymic Treg development which allows the CNS2 enhancer region to drive high levels of FoxP3 expression in committed Tregs (Toker et al. 2013; Yue et al. 2016). Interestingly, while we observed the predicted patterns of endogenous CNS2 methylation/demethylation in NSG Tconv/Treg subsets respectively, the viral CNS2 sequence was fully demethylated in all subsets. This suggests that introduction of a demethylated CNS2 region at the HSC state (via LV transduction) may allow this region within the LV to remain unmethylated throughout development; in contrast, the endogenous FOXP3 gene may be globally methylated earlier in embryogenesis with specific demethylation occurring during thymopoiesis and Treg development. Despite the discordance between endogenous and viral CNS2 methylation, LV expression remains highly selective for the Treg lineage suggesting that demethylated CNS2 alone does not drive FoxP3 expression and that CNS1, CNS3, and the FoxP3 promoter may be confer additional specificity. Furthermore, as hypermethylation of CNS2 is associated with reduced FoxP3 expression (Li et al. 2014) and impaired Treg function in patients with autoimmune disorders (Guo et al. 2016), it is tempting to speculate that a LV which maintains demethylated CNS2 could be advantageous for improving FoxP3 expression in autoimmune disorders, though this possibility remains to be explored.

FoxP3+ Tregs develop both in the thymus under central tolerance signals (nTregs), or from peripheral FoxP3-Tconv in response to a tolerance-inducing signals (pTregs). Pivotal work by Haribhai et al. has suggested that both nTreg and pTreg subsets play non-redundant roles in controlling the autoimmune defect in the scurfy mouse and are critical for basal maintenance of immunologic tolerance to self-antigens (Haribhai et al. 2011). Thus, an effective therapy for IPEX would ideally restore both thymic and peripheral Treg development. To determine if expressing FoxP3 cDNA in a lineage specific manner could achieve FoxP3 expression levels sufficient to restore Treg function and phenotype, we tested CNS123p-FoxP3-mStrawberry in scurfy HSC. Restoration of nTreg development is evidenced by the Treg phenotype (GITR+, CD25+) exhibited by corrected scurfy thymocytes, and the in vitro suppressive capacity of CD4+ mStrawberry+ splenocytes. Our studies also suggest restoration of the pTreg compartment, demonstrated by the ability of corrected scurfy CD4 cells to induce de novo FoxP3 expression upon activation in the presence of TGFβ.

An important factor to consider prior to clinical translation is the level of HSC correction and engraftment required to resolve autoimmunity in IPEX patients. Reports of allogeneic HSC transplant in IPEX patients demonstrate that successful resolution of autoimmunity can be achieved with partial donor chimerism (Barzaghi et al. 2018). In some of these cases, it has been shown that donor Tregs exhibit a selective advantage with full donor chimerism in the Treg compartment despite low levels of total donor engraftment (Kasow et al. 2011; Seidel et al. 2009). In our studies rescuing scurfy neonates with adoptive transfer of CD4+ cells, a VCN of >3 in purified CD4 products was required to produce Tregs with sufficiently high FoxP3 expression to correct autoimmunity. This may suggest that our designed combination of FoxP3 enhancers included in the LV construct may be less efficient at promoting FoxP3 expression than the endogenous gene, or alternatively that the human regulatory elements included in the LV provide suboptimal expression in murine cells. Regardless, our NSG xenograft studies show that a VCN of >3 can be easily achieved in human CD34+ cells. Further studies will aim to evaluate the corrective VCN required to restore the development of functional Tregs from human IPEX HSC.

In summary, we demonstrate the development of an endogenously regulated LV which successfully restores Treg development from FoxP3-deficient HSC. Corrected Tregs closely resemble WT Tregs in phenotype and function, and importantly, are capable of reversing the autoimmune phenotype of the scurfy mouse. Furthermore, humanized mouse models reveal efficient gene modification of LT-HSC and high levels of lineage-specific expression, suggesting favorable translation of this therapy for IPEX patients. More broadly, this work shows the first demonstration of reprogramming the immune system at the HSC level to restore immunologic tolerance. While IPEX is a rare disease, its severity and lack of suitable treatment make it an excellent gateway disease to provide biologic insight into the development of new HSC-based therapies which modulate immunologic tolerance. These findings pave the way for the treatment of IPEX patients by autologous HSCT and may provide valuable insights into new treatments for patients with autoimmune disorders of different origin.

Materials and Methods

Lentiviral Vectors

Construction of MNDU3-GFP (Logan et al. 2004) and UBC-mCitrine (Baldwin et al. 2015) has been described. MNDU3-FoxP3-IRES-GFP was a kind gift from Dr. Gay Crooks. The CNS123p-mStrawberry and CNS123p-FoxP3-mStrawberry lentiviral vectors were cloned into an empty CCL backbone (Dull et al. 1998). Fragments were synthesized as gBlocks (R) (Integrated DNA Technologies) with compatible ends to be cloned using NEBuilder (R) HiFi DNA Assembly Kit (New England Biolabs) Lentiviral vectors were packaged with a VSV-G pseudotype, concentrated and titered as described (Cooper et al. 2011).

Cell Lines

MT2 cells were obtained through the NIH AIDS Reagent Program, Division of AIDS, NIAID, NIH: MT-2 Cells from Dr. Douglas Richman (Haertle et al. 1988; Harada, Koyanagi, and Yamamoto 1985). Jurkat and K562 cells were obtained from ATCC. Cells were maintained in R10 (RPMI [Gibco]/10% FBS [Gibco]/1× Penicillin/Streptomycin/Glutamine [PSG, Gemini Bio Products]). Cells were plated at 1E6 cells/mL and transduced with CNS123p–mStrawberry at a range of concentrations (1E5 TU/mL-1E8 TU/mL, MOI 0.1-100) followed by a change to fresh R10 the following day. After 10 days of culture, cells were analyzed by flow cytometry for mStrawberry expression and genomic DNA was isolated for vector copy number analysis.

Mice

All animals involved in experiments were cared for and handled in accordance with protocols approved by the UCLA Animal Research Committee under the Division of Laboratory Medicine. B6 (CD45.2), B6. SJL (CD45.1), B6-FoxP3GFP (CD45.2), B6-scurfy, NSG and NSG-SGM3 mice were purchased from Jackson labs colonies were maintained at UCLA. The following breeding strategy was used for scurfy mice. Heterozygous female scurfy mice (CD45.2, X/XSf, phenotypically normal) were mated with wild-type B6 (CD45.2) or B6. SJL (CD45.1) males to produce sub-colonies of CD45.2, CD45.1, and CD45.1/CD45.2 scurfy mice. Scurfy male neonates (Xsf/Y) were rescued by intraperitoneal injection of $60\times10^6$ WT splenocytes and re-mated to heterozygous scurfy females (X/XSf) to obtain scurfy females (Xsf/Xsf). Rescued scurfy male (Xsf/Y) and scurfy female (Xsf/Xsf) mice were mated to generate litters in which all pups were FoxP3 deficient. Male and female scurfy mice exhibited indistinguishable disease progression and were used interchangeably.

Murine Congenic Transplants

Bone marrow cells were obtained by crushing aseptically isolated femurs, tibias, pelvises, spines, and humeri in a mortar and pestle. Lin– cells were obtained using a lineage depletion kit (Miltenyi Biotec) according to manufacturer's instructions. Lin– cells were resuspended in murine transduction media (Stem Span SFEM [Stem Cell Technologies], 1×PSG [Gemini Bio Products], 100 ng/ml mTPO, 10 ng/ml mSCF [Peprotech], 5 mg/mL polybrene [Sigma Aldrich]) at $2\times10^6$ lin– cells/mL, plated on retronectin (Takara) coated wells (20 ng/mL for 2 hours at RT) and incubated with LV overnight. In transplants used to generate corrected Tregs for adoptive transfer, 1 mg/mL poloxamer KP338 (BASF) was added to improve gene transfer efficiency.

After transduction, cells were collected, washed, and resuspended in PBS. 6-10 week old B6. SJL (CD45.1) or B6 (CD45.2) recipients were irradiated with 1200 Rad (Dose rate ~100 Rad/min) using a split dose of 600+600 Rad with 3-4 hours between doses. Cells were injected via retro-orbital injection 1-4 hours after the last radiation dose. Transplanted cell doses ranged from 5E5-1E6 lin– cells per mouse.

Determination of Vector Copies (VC) Per Cell

Genomic DNA was extracted from samples using the PureLink genomic DNA kit (Invitrogen). The average VC/cell was measured using ddPCR. Reaction mixtures were prepared consisting of 22 µl volumes containing 1× ddPCR Master Mix (Bio-Rad), primers, and probe specific to the HIV-1 Psi region (400 nM and 100 nM for primers and probe, respectively), DraI (40 U; New England Biolabs), and 1.1 µl of the genomic DNA sample. Droplet generation was performed using the QX100 Droplet Generator (Bio-Rad). Thermal cycling conditions consisted of 95° C. 10 minutes, 94° C. 30 seconds and 60° C. 1 minute (55 cycles), 98° C. 10 minutes (1 cycle), and 12° C. hold. The concentration of specific amplified portions was quantified using the QX200 Droplet Reader/Quantasoft V1.7 (Bio-Rad) and normalized using primers to the autosomal human gene SDC4 gene, or uc378 gene for murine samples. Primer/probe sequences are listed in Table 2.

TABLE 2

Primer and Probe sequences for ddPCR quantitation of Vector Copy Number.

| | Sequence | Seq ID No |
|---|---|---|
| | **PsiUS** | |
| Forward primer | 5' AAG TAG TGT GTG CCC GTC TG 3' | 2 |
| Reverse primer | 5' CCT CTG GTT TCC CTT TCG CT 3' | 3 |
| Probe | 5' FAM-CCC TCA GAC-ZEN*-CCT TTT AGT CAG TGT GGA AAA TCT CTA G-IBFQ** 3' | 4 |
| | **Uc378** | |
| Forward primer | 5' CGC CCC CTC CTC ACC ATT AT 3' | 5 |
| Reverse primer | 5' CAT CAC AAC CAT CGC TGC CT 3' | 6 |
| Probe | 5' HEX-TTA CCT TGC-ZEN*-TTG TCG GAC CAA GGC A-IBFQ 3** | 7 |
| | **SDC4** | |
| Forward primer | 5' CAG GGT CTG GGA GCC AAG T 3' | 8 |
| Reverse primer | 5' GCA CAG TGC TGG ACA TTG ACA 3' | 9 |
| Probe | 5' HEX-CCC ACC GAA-ZEN*-CCC AAG AAA CTA GAG GAG AAT-IBFQ** 3' | 10 |

*IBFQ = Iowa Black ® FQ, **ZEN = internal modification from IDT-Integrated DNA Technologies Murine CD4 Isolation Murine splenocytes were obtained by aseptic removal and gentle crushing of spleens through a 70 µM mesh filter. RBC lysis was performed using a pre-prepared ammonium chloride based lysing buffer (BD Biosciences). Splenocytes were enriched for CD4+ cells using a CD4 isolation kit (Miltenyi Biotec). Briefly, splenocytes were labeled with a cocktail of biotinylated antibodies labeling CD4– cells, followed by labeling with anti-biotin magnetic beads. CD4-cells were separated on an LS column (Miltenyi Biotec) while CD4+ cells were collected in the flow through. In experiments utilizing adoptive transfer of CD45.2+CD4+ cells to scurfy neonates, an anti-CD45.1 biotinylated antibody was added in the initial incubation step to deplete any remaining recipient CD45.1 cells.

Treg Suppression Assay

CD4-enriched splenocytes were labeled with CD4-APC (Clone RM4-5, BD) and Ghost 780 viability dye (Tonbo Biosciences) prior to FACS sorting. Viable CD4+GFP+ (WT Tregs) or CD4+mStrawberry+ (Scurfy Tregs) were sorted for evaluation of suppressive function. Tresp cells (WT B6 CD4+ cells) were labeled with 5 µM Cell Trace violet proliferation dye (Thermo Fisher) for 20 min at 37° C., washed, and co-cultured with sorted Tregs at a 1:1 ratio in R10 without cytokines. Experiments ranged from 2.5E4-5E4 Tresp cells/well of a 96 well U bottom plate. Mouse CD3/CD28 T Activator Dynabeads (ThermoFisher) were added to cultures at a ratio of 1 bead: 1 Tresp cell. Cells were cultured for 3 days followed by FACS analysis for dilution of proliferation dye. Proliferation index was calculated using FlowJo V7.6.5 (TreeStar).

Rescue of Scurfy Neonates with Corrected Tregs and Analysis

Scurfy neonates were injected intraperitoneally with purified CD4+ cells in 50 uL of PBS using a 29 gauge insulin syringe. Absolute numbers of CD4 cells and the relative Treg content of each population are listed in FIG. 16. Blood was collected from 21 d old scurfy mice by submandibular puncture into serum separator tubes (RAM Scientific) and centrifuged at 500× g for 10 min to obtain plasma for cytokine analysis. Cytokines were analyzed by the UCLA Immune Assessment Core using the Luminex platform.

Humanized Xenografts

Umbilical CB was obtained after vaginal and cesarean deliveries at UCLA Medical Center. All specimens obtained have been deemed as anonymous medical waste exempt from IRB review. MNCs were isolated using Ficoll-Paque PLUS (GE Healthcare) density centrifugation within 48 hours of collection followed by CD34 enrichment according to manufacturer's instruction (Miltenyi Biotec). CD34+ cells from single cords were frozen in cryovials in 90% FBS (Gibco)/10% DMSO (Sigma Aldrich) and stored for later use. Upon thawing, CD34+ cells were resuspended in human transduction medium (X-vivo-15 [Lonza], 1×PSG [Gemini Bio Products], 50 ng/mL SCF, 50 ng/ml TPO, 50 ng/mL Flt3L [Peprotech]). Cells were cultured in transduction medium for 24 hours, followed by incubation with LV for another 24 hours. After transduction, CD34+ cells were collected, washed in PBS, and incubated with OKT3 (Tonbo Biosciences, 1 μg/100 μL) for 30 min on ice to prevent GVHD from contaminating T cells present in the CD34+ graft (Wunderlich et al. 2014). Immediately prior to transplant, 1-3 day old neonatal NSG mice were irradiated at a dose of 125 Rad with a 137 Cs source and dose rate of 100 Rads/min. Each mouse received 1-3×$10^5$ CD34+ cells.

Flow Cytometry

Single cell suspensions from BM were obtained by crushing femurs as described above. Thymus and spleen were prepared by crushing tissue through a 70 uM strainer. Samples were prepared for flow cytometry using the following method: Cells were resuspended in 50 uL of FACS buffer (phosphate buffered saline [PBS, Corning]/0.5% Bovine Serum Albumin [BSA, Sigma]) and incubated with 1 μL of each antibody and 0.5 μL of Ghost 780 viability dye (Tonbo Biosciences) for 20-30 min at 4° C.

All antibodies were purchased from BD Biosciences. The following antibodies were used for analysis of human cells: CD45-APC, CD45-FITC, CD33-BV421, CD19-PE-Cy7, CD34-FITC, CD34-PE-Cy7, CD4-FITC, CD4-PE-Cy7, CD8-APC, CD25-V450, CD25-PerCPCy5.5. The following antibodies were used for analysis of murine cells: CD45.1-FITC, CD45.1-V450, CD45.1-APC, CD45.2-FITC, CD45.2-V450, CD4-PECy7, CD4-APC, CD8-PE-Cy7, Gr1-APC, B220-PerCp, CD3-PerCp, cKit-APC, CD44-PerCpCy5.5, CD62L-PE-Cy7, GITR-APC, CD25-APC, CTLA4-APC.

For intracellular FoxP3 staining, cells were first stained with cell surface markers and fixable viability dye as described above. After washing, cells were fixed and permeabilized using the FoxP3 staining buffer set (cBioscience) according to manufacturers' directions. Human FoxP3-PE or human FoxP3-APC (ebioscience, clone 236A/E7) was added for 30-60 min at RT. FoxP3+ gates were set using an isotype control. Samples were acquired on a LSRII or LSR-Fortessa flow cytometer (BD Biosciences). Data were analyzed using FlowJo V10 (TreeStar).

Methylation Analysis/Bisulfite Sequencing

Genomic DNA was extracted from sorted Treg (CD4+CD25+) and Tconv (CD4+CD25−) subsets using the Purelink Genomic DNA mini kit (Invitrogen). CpG dinucleotide methylation analysis of CNS2 of the human FoxP3 gene was performed by EpigenDx and determined by bisulfite treatment of RNase-treated genomic DNA, followed by PCR amplification and pyrosequencing (EpigenDx assay ADS783-FS2). A custom assay was performed by EpigenDx for methylation analysis of FoxP3 CNS2 from integrated LV DNA using the following primers which uniquely recognize viral CNS2: FoxP3 CNS2 Viral F: TGGAGTTAGATTGTTTGGGA (SEQ ID NO:11); FoxP3 CNS2 Viral R: CACCTATAAATCCAAATACCCCAC (SEQ ID NO:12).

REFERENCE FOR EXAMPLE 2

Baldwin, Kismet, Fabrizia Urbinati, Zulema Romero, Beatriz Campo-Fernandez, Michael L Kaufman, Aaron R Cooper, Katelyn Masiuk, Roger P Hollis, and Donald B Kohn. 2015. "Enrichment of Human Hematopoietic Stem/Progenitor Cells Facilitates Transduction for Stem Cell Gene Therapy." *Stem Cells* 33(5): 1532-1542.

Barzaghi, Federica, Laura Cristina Amaya Hernandez, Benedicte Neven, Silvia Ricci, Zeynep Yesim Kucuk, Jack J Bleesing, Zohreh Nademi, et al. 2018. "Long-Term Follow-up of IPEX Syndrome Patients after Different Therapeutic Strategies: An International Multicenter Retrospective Study." *J. Allegery Clin. Immunol.,* 141(3): 1036-1049.

Bennett, Craig L., Jacinda Christie, Fred Ramsdell, Mary E. Brunkow, Polly J. Ferguson, Luke Whitesell, Thaddeus E. Kelly, Frank T. Saulsbury, Phillip F. Chance, and Hans D. Ochs. 2001. "The Immune Dysregulation, Polyendocrinopathy, Enteropathy, X-Linked Syndrome (IPEX) Is Caused by Mutations of FOXP3." *Nat. Genet.* 27(1): 20-21.

Billerbeck, Eva, Walter T Barry, Kathy Mu, Marcus Dorner, Charles M Rice, and Alexander Ploss. 2011. "Development of Human CD4+FoxP3+ Regulatory T Cells in Human Stem Cell Factor-, Granulocyte-Macrophage Colony-Stimulating Factor-, and Interleukin-3-Expressing NOD-SCID IL2Rγ(Null) Humanized Mice." *Blood* 117(11): 3076-3086.

Canté-Barrett, Kirsten, Rui D. Mendes, Willem K. Smits, Yvette M. van Helsdingen-van Wijk, Rob Pieters, and Jules P. P. Meijerink. 2016. "Lentiviral Gene Transfer into Human and Murine Hematopoietic Stem Cells: Size Matters." BMC Research Notes 9(1): 312.

Cavazzana-Calvo, Marina, Emmanuel Payen, Olivier Negre, Gary Wang, Kathleen Hehir, Floriane Fusil, Julian Down, et al. 2010. "Transfusion Independence and HMGA2 Activation after Gene Therapy of Human β-Thalassaemia." *Nature* 467(7313): 318-322.

Chen, WanJun, Wenwen Jin, Neil Hardegen, Ke-Jian Lei, Li Li, Nancy Marinos, George McGrady, and Sharon M Wahl. 2003. "Conversion of Peripheral CD4+CD25− Naive T Cells to CD4+CD25+ Regulatory T Cells by TGF-Beta Induction of Transcription Factor Foxp3." *J. Exp. Med.* 198(12): 1875-1886.

Cooper, Aaron R, Sanjeet Patel, Shantha Senadheera, Kathrin Plath, Donald B Kohn, and Roger P Hollis. 2011. "Highly Efficient Large-Scale Lentiviral Vector Concentration by Tandem Tangential Flow Filtration." *J. Virol. Meth.* 177(1): 1-9.

Curotto de Lafaille, Maria A, Andreia C Lino, Nino Kutchukhidze, and Juan J Lafaille. 2004. "CD25− T Cells Generate CD25+Foxp3+ Regulatory T Cells by Peripheral Expansion." *J. Immunol.* 173(12): 7259-7268.

Dull, T, R Zufferey, M Kelly, R J Mandel, M Nguyen, D Trono, and L Naldini. 1998. "A Third-Generation Lentivirus Vector with a Conditional Packaging System." *J. Virol.* 72(11): 8463-8471.

Fontenot, Jason D., Marc A. Gavin, and Alexander Y. Rudensky. 2003. "Foxp3 Programs the Development and Function of CD4+CD25+ Regulatory T Cells." *Nat. Immunol.* 4(4): 330-336.

Guo, Huifang, Ming Zheng, Kui Zhang, Fengfan Yang, Xin Zhang, Qing Han, Zhi-Nan Chen, and Ping Zhu. 2016. "Functional Defects in CD4+ CD25high FoxP3+ Regulatory Cells in Ankylosing Spondylitis." *Sci. Rep.* 6(1): 37559.

Haertle, T, CJ Carrera, DB Wasson, and LC Sowers. 1988. "Metabolism and Anti-Human Immunodeficiency Virus-1 Activity of 2-Halo-2', 3'-Dideoxyadenosine Derivatives." *J. Biol. Chem.* 263:5870-5875.

Harada, S, Y Koyanagi, and N Yamamoto. 1985. "Infection of HTLV-III/LAV in HTLV-I-Carrying Cells MT-2 and MT-4 and Application in a Plaque Assay." *Science,* 229(4713): 563-566.

Haribhai, Dipica, Jason B Williams, Shuang Jia, Derek Nickerson, Erica G Schmitt, Brandon Edwards, Jennifer Ziegelbauer, et al. 2011. "A Requisite Role for Induced Regulatory T Cells in Tolerance Based on Expanding Antigen Receptor Diversity." *Immunity,* 35(1): 109-122.

Kasow, Kimberly A., Vanessa M. Morales-Tirado, David Wichlan, Sheila A. Shurtleff, Allistair Abraham, Derek A. Persons, and Janice M. Riberdy. 2011. "Therapeutic in vivo Selection of Thymic-Derived Natural T Regulatory Cells Following Non-Myeloablative Hematopoietic Stem Cell Transplant for IPEX." *Clin. Immunol.* 141(2): 169-176.

Khattri, R, D Kasprowicz, T Cox, M Mortrud, M W Appleby, M E Brunkow, S F Ziegler, and F Ramsdell. 2001. "The Amount of Scurfin Protein Determines Peripheral T Cell Number and Responsiveness." *J. Immunol.* 167(11): 6312-6320.

Kumar, Mukesh, Brian Keller, Ndeye Makalou, and Richard E. Sutton. 2001. "Systematic Determination of the Packaging Limit of Lentiviral Vectors." *Hum. Gene Ther.* 12(15): 1893-1905.

Li, Xudong, Yuqiong Liang, Mathias LeBlanc, Chris Benner, and Ye Zheng. 2014a. "Function of a Foxp3 Cis-Element in Protecting Regulatory T Cell Identity." *Cell,* 158(4): 734-748.

Liu, Mingdong, Matthew T Maurano, Hao Wang, Heyuan Qi, Chao-Zhong Song, Patrick A Navas, David W Emery, John A Stamatoyannopoulos, and George Stamatoyannopoulos. 2015. "Genomic Discovery of Potent Chromatin Insulators for Human Gene Therapy." *Nat. Biotechnol.* 33(2): 198-203.

Logan, Aaron C, Sarah J Nightingale, Dennis L Haas, Gerald J Cho, Karen A Pepper, and Donald B Kohn. 2004. "Factors Influencing the Titer and Infectivity of Lentiviral Vectors." *Hum. Gene Ther.* 15:976-988.

Morgan, Richard A, David Gray, Anastasia Lomova, and Donald B Kohn. 2017. "Hematopoietic Stem Cell Gene Therapy: Progress and Lessons Learned." *Cell Stem Cell,* 21(5): 574-590.

Passerini, Laura, Eva Rossi Mel, Claudia Sartirana, Georgia Fousteri, Attilio Bondanza, Luigi Naldini, Maria Grazia Roncarolo, and Rosa Bacchetta. 2013. "CD4+ T Cells from IPEX Patients Convert into Functional and Stable Regulatory T Cells by FOXP3 Gene Transfer." *Sci. Transl. Med.* 5(215): 215ra174.

Riley, James L., Carl H. June, and Bruce R. Blazar. 2009. "Human T Regulatory Cell Therapy: Take a Billion or So and Call Me in the Morning." *Immunol.* 30(5): 656-665.

Safinia, Niloufar, Pervinder Sagoo, Robert Lechler, and Giovanna Lombardi. 2010. "Adoptive Regulatory T Cell Therapy: Challenges in Clinical Transplantation." *Curr. Opin. Organ Transpl.* 15(4): 427-434.

Santoni de Sio, F. R., L. Passerini, M. M. Valente, F. Russo, L. Naldini, M. G. Roncarolo, and R. Bacchetta. 2017. "Ectopic FOXP3 Expression Preserves Primitive Features Of Human Hematopoietic Stem Cells While Impairing Functional T Cell Differentiation." *Sci. Rep.* 7(1): 15820.

Seidel, Markus G, Gerhard Fritsch, Thomas Lion, Birgit Jürgens, Andreas Heitger, Rosa Bacchetta, Anita Lawitschka, et al. 2009. "Selective Engraftment of Donor CD4+25high FOXP3-Positive T Cells in IPEX Syndrome after Nonmyeloablative Hematopoietic Stem Cell Transplantation." *Blood,* 113(22): 5689-5691.

Tai, Xuguang, Batu Erman, Amala Alag, Jie Mu, Motoko Kimura, Gil Katz, Terry Guinter, et al. 2013. "Foxp3 Transcription Factor Is Proapoptotic and Lethal to Developing Regulatory T Cells Unless Counterbalanced by Cytokine Survival Signals." *Immunity,* 38(6): 1116-1128.

Toker, Aras, Dirk Engelbert, Garima Garg, Julia K Polansky, Stefan Floess, Takahisa Miyao, Udo Baron, et al. 2013. "Active Demethylation of the Foxp3 Locus Leads to the Generation of Stable Regulatory T Cells within the Thymus." *J. Immunol.* 190(7): 3180-3188.

Wildin, Robert S., Fred Ramsdell, Jane Peake, Francesca Faravelli, Jean-Laurent Casanova, Neil Buist, Ephrat Levy-Lahad, et al. 2001a. "X-Linked Neonatal Diabetes Mellitus, Enteropathy and Endocrinopathy Syndrome Is the Human Equivalent of Mouse Scurfy." *Nat. Genet.* 27(1): 18-20.

Wunderlich, Mark, Ryan A Brooks, Rushi Panchal, Garrett W Rhyasen, Gwenn Danet-Desnoyers, and James C Mulloy. 2014. "OKT3 Prevents Xenogeneic GVHD and Allows Reliable Xenograft Initiation from Unfractionated Human Hematopoietic Tissues." *Blood,* 123 (24): e134-144.

Yue, Xiaojing, Sara Trifari, Tarmo Äijö, Ageliki Tsagaratou, William A Pastor, Jorge A Zepeda-Martínez, Chan-Wang J Lio, et al. 2016. "Control of Foxp3 Stability through Modulation of TET Activity." *J. Exp. Med.* 213(3): 377-397.

Zheng, Ye, Steven Josefowicz, Ashutosh Chaudhry, Xiao P. Peng, Katherine Forbush, and Alexander Y. Rudensky. 2010. "Role of Conserved Non-Coding DNA Elements in the Foxp3 Gene in Regulatory T-Cell Fate." *Nature,* 463(7282): 808-812.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant lentiviral vector (LV) comprising:

an expression cassette comprising enhancer elements for driving gene expression of a nucleic acid encoding a protein, said enhancer elements consisting of a human FoxP3-CNS1 sequence, a human FoxP3-CNS2 sequence, and a human FoxP3-CNS3 sequence upstream from a human FoxP3 promoter;

where said LV is an HIV-derived TAT-independent and self-inactivating (SIN) lentiviral vector comprising a U3 region lacking a TATA box, an R region, a U 5 region, a packaging signal, a rev response element (RRE), and a central polypurine tract (cPPT) upstream from said enhancer elements, U3 region, R region, and U5 region downstream from said nucleotide sequence encoding the protein; and a nucleic acid sequence encoding said protein sequence operably linked to said enhancer elements and said human FoxP3 promoter.

2. The lentiviral vector of claim 1, where said LV has a length of less than 10 kb.

3. The lentiviral vector of claim 1, wherein said vector comprises a FoxP3 3'UTR.

4. The lentiviral vector of claim 1, wherein said vector comprises an insulator element in the U3 region.

5. The lentiviral vector of claim 1, wherein said enhancer elements drive Treg lineage specific expression in cells transfected with said vector.

6. The lentiviral vector of claim 1, wherein said lentiviral vector comprises a pCCL backbone.

7. A packaging cell transfected with a vector of claim 1.

8. A lentiviral particle encoded by a lentiviral vector of claim 1.

9. An infectious lentivirus particle produced by co-transfecting a packaging cell with the lentiviral vector of claim 1, and with one or more packaging plasmids encoding Gag-Pol and Rev, and an envelope plasmid encoding a heterologous envelope glycoprotein.

10. The lentiviral particle of claim 8, wherein said lentiviral particle is pseudotyped with a vesicular stomatitis virus glycoprotein (VSV-G) envelope.

* * * * *

SEQUENCE LISTING

```
Sequence total quantity: 12
SEQ ID NO: 1            moltype = DNA  length = 9841
FEATURE                 Location/Qualifiers
misc_feature            1..9841
                        note = Foxp3 Expression Vector nucleotide sequence
source                  1..9841
                        mol_type = other DNA
                        organism = synthetic construct
SEQUENCE: 1
caggtggcac ttttcgggga aatgtgcgcg gaacccctat ttgtttattt ttctaaatac  60
attcaaatat gtatccgctc atgagacaat aaccctgata aatgcttcaa taatattgaa  120
aaaggaagag tatgagtatt caacatttcc gtgtcgccct tattcccttt tttgcggcat  180
tttgccttcc tgtttttgct cacccagaaa cgctggtgaa agtaaaagat gctgaagatc  240
agttgggtgc acgagtgggt tacatcgaac tggatctcaa cagcggtaag atccttgaga  300
gttttcgccc cgaagaacgt tttccaatga tgagcacttt taaagttctg ctatgtggcg  360
cggtattatc ccgtattgac gccgggcaag agcaactcgg tcgccgcata cactattctc  420
agaatgactt ggttgagtac tcaccagtca cagaaaagca tcttacggat ggcatgacag  480
taagagaatt atgcagtgct gccataacca tgagtgataa cactgcggcc aacttacttc  540
tgacaacgat cggaggaccg aaggagctaa ccgctttttt gcacaacatg ggggatcatg  600
taactcgcct tgatcgttgg gaaccggagc tgaatgaagc cataccaaac gacgagcgtg  660
acaccacgat gcctgtagca atggcaacaa cgttgcgcaa actattaact ggcgaactac  720
ttactctagc ttcccggcaa caattaatag actggatgga ggcggataaa gttgcaggac  780
cacttctgcg ctcggccctt ccggctggct ggtttattgc tgataaatct ggagccggtg  840
agcgtgggtc tcgcggtatc attgcagcac tggggccaga tggtaagccc tcccgtatcg  900
tagttatcta cacgacgggg agtcaggcaa ctatggatga acgaaataga cagatcgctg  960
agataggtgc ctcactgatt aagcattggt aactgtcaga ccaagtttac tcatatatac  1020
tttagattga tttaaaactt catttttaat ttaaaaggat ctaggtgaag atcctttttg  1080
ataatctcat gaccaaaatc ccttaacgtg agttttcgtt ccactgagcg tcagaccccg  1140
tagaaaagat caaaggatct tcttgagatc cttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtc cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560
aaagcgccac gcttcccgaa gggagaaagg cggacaggta tccggtaagc ggcagggtcg  1620
gaacaggaga gcgcacgagg gagcttccag ggggaaacgc ctggtatctt tatagtcctg  1680
tcgggtttcg ccacctctga cttgagcgtc gatttttgtg atgctcgtca ggggggcgga  1740
gcctatggaa aaacgccagc aacgcggcct ttttacggtt cctggccttt tgctggcctt  1800
ttgctcacat gttctttcct gcgttatccc ctgattctgt ggataaccgt attaccgcct  1860
ttgagtgagc tgataccgct cgccgcagcc gaacgaccga gcgcagcgag tcagtgagcg  1920
aggaagcgga agagcgccca atacgcaaac cgcctctccc cgcgcgttgg ccgattcatt  1980
aatgcagctg gcacgacagg tttcccgact ggaaagcggg cagtgagcgc aacgcaatta  2040
atgtgagtta gctcactcat taggcacccc aggctttaca ctttatgctt ccggctcgta  2100
tgttgtgtgg aattgtgagc ggataacaat ttcacacagg aaacagctat gaccatgatt  2160
acgccaagcg cgcaattaac cctcactaaa gggaacaaaa gctggagctg caagcttggc  2220
cattgcatac gttgtatcca tatcataata tgtacattta tattggctca tgtccaacat  2280
taccgccatg ttgacattga ttattgacta gttattaata gtaatcaatt acggggtcat  2340
tagttcatag cccatatatg gagttccgcg ttacataact tacggtaaat ggcccgcctg  2400
gctgaccgcc caacgacccc cgcccattga cgtcaataat gacgtatgtt cccatagtaa  2460
cgccaatagg gactttccat tgacgtcaat gggtggagta tttacggtaa actgcccact  2520
tggcagtaca tcaagtgtat catatgccaa gtacgccccc tattgacgtc aatgacggta  2580
aatggcccgc ctggcattat gcccagtaca tgaccttatg ggactttcct acttggcagt  2640
acatctacgt attagtcatc gctattacca tggtgatgcg gttttggcag tacatcaatg  2700
ggcgtggata gcggtttgac tcacggggat ttccaagtct ccaccccatt gacgtcaatg  2760
ggagtttgtt ttggcaccaa aatcaacggg actttccaaa atgtcgtaac aactccgccc  2820
cattgacgca aatgggcggt aggcgtgtac ggtgggaggt ctatataagc agagctcgtt  2880
tagtgaaccg gggtctctct ggttagacca gatctgagcc tgggagctct ctggctaact  2940
agggaaccca ctgcttaagc ctcaataaag cttgccttga gtgcttcaag tagtgtgtgc  3000
ccgtctgttg tgtgactctg gtaactagag atccctcaga cccttttagt cagtgtggaa  3060
aatctctagc agtggcgccc gaacagggac ctgaaagcga aagggaaacc agaggagctc  3120
tctcgacgca ggactcggct tgctgaagcg cgcacggcaa gaggcgaggg gcggcgactg  3180
gtgagtacgc caaaaatttt gactagcgga ggctagaagg agagagatgg gtgcgagagc  3240
gtcagtatta agcgggggag aattagatcg cgatgggaaa aaattcggtt aaggccaggg  3300
ggaaagaaaa aatataaatt aaaacatata gtatgggcaa gcagggagct agaacgattc  3360
gcagttaatc ctggcctgtt agaaacatca gaaggctgta gacaaatact gggacagcta  3420
caaccatccc ttcagacagg atcagaagaa cttagatcat tatataatac agtagcaacc  3480
ctctattgtg tgcatcaaag gatagagata aaagacacca aggaagcttt agacaagata  3540
gaggaagagc aaaacaaaag taagaccacc gcacagcaag cggccgctga tcttcagacc  3600
tggaggagga gatatgaggg acaattggag aagtgaatta tataaatata aagtagtaaa  3660
aattgaacca ttaggagtag cacccaccaa ggcaaagaga agagtggtgc agagagaaaa  3720
aagagcagtg ggaataggag ctttgttcct tgggttcttg ggagcagcag gaagcactat  3780
gggcgcagcg tcaatgacgc tgacggtaca ggccagacaa ttattgtctg gtatagtgca  3840
gcagcagaac aatttgctga gggctattga ggcgcaacag catctgttgc aactcacagt  3900
ctggggcatc aagcagctcc aggcaagaat cctggctgtg gaaagatacc taaaggatca  3960
acagctcctg gggatttggg gttgctctgg aaaactcatt tgcaccactg ctgtgccttg  4020
gaatgctagt tggagtaata aatctctgga acagatggaa tcacacgacc tggatggagt  4080
gggacagaga aattaacaat tacacaagct taatacactc cttaattgaa gaatcgcaaa  4140
```

```
accagcaaga aaagaatgaa caagaattat tggaattaga taaatgggca agtttgtgga  4200
attggtttaa cataacaaat tggctgtggt atataaaatt attcataatg atagtaggag  4260
gcttggtagg tttaagaata gtttttgctg tactttctat agtgaataga gttaggcagg  4320
gatattcacc attatcgttt cagacccacc tcccaacccc gaggggaccc gacaggcccg  4380
aaggaataga agaagaaggt ggagagagag acagagacag atccattcga ttagtgaacg  4440
gatctcgacg gtatcgatct cgacacaaat ggcagtattc atccacaatt ttaaaagaaa  4500
aggggggatt ggggggtaca gtgcagggga aagaatagta gacataatag caacagacat  4560
acaaactaaa gaattacaaa aacaaattac aaaaattcaa aattttcggg tttattacag  4620
ggacagcaga gatccagttt gggtcgagga tatctaggtt agtctttttt tctgtggctt  4680
ctgtctctgg ttttgtgctt agaaagtcct ttcctacttg aaaatgagat aaatgttcac  4740
ctatgttggc ttctagtctc ttttatggct tcattttttc catttactat agaggttaag  4800
agtgtgggta ctggagccag actgtctggg acaaacccag cgtcacccca agccctatgt  4860
gtgattttta gccaggcact taacctctcc atccaagaag ggccaggtct tcagagctag  4920
gggcttgtca tagtggccag atggacatca cctaccacat ccaccagcac ccatgtcacc  4980
ccacctgggc caagcctgct gcaggacagg gcagccagtt ctcggaacga aacctgtggg  5040
gtggggtatc tgccctcttc tcttcctccg tggtgtcgat gaagcccggc gcatccggcc  5100
gccatgacgt caatggcgga aaaatctggg caagtcgggg gctgtgacaa cagggcccag  5160
atgcagaccc cgatatgaaa acataatctg tgtcccagaa acatccccca ttcagcttct  5220
gagaaaccca gtcagaaagg gacgtcccaa cagaggccct gggcccagga tggggcaggc  5280
agggtggggt acctggacct acaggtgccg acctttactg tggcactggg cgggaggggg  5340
gctggctggg gcacaggaag tggtttctgg gtcccaggca agtctgtgac ttatgcagat  5400
gttgcagggc caagaaaatc cccacctgcc aggcctcaga gattggaggc tctccccgac  5460
ctcccaatcc tcccatccac acatagagct tcagattctc tttctttccc cagagaccct  5520
caaatatcct ctcactcaca gaatggtgtc tctgcctgcc tcgggttggc cctgtgattt  5580
atttagttc ttttcccttg ttttttttt ttcaaactct atacactttt gttttaaaaa  5640
ctgtggtttc tcatgagccc tattatctca ttgatacctc tcacctctgt ggtgagggga  5700
agaaatcata ttttcagatg actcgtaaag ggcaaagaaa aaaacccaaa atttcaaaat  5760
ttccgtttaa gtctcataat caagaaaagg agaaacacag agagagagaa aaaaaaaact  5820
atgagaaccc ctccccaccc cgtgattatc agcgcacaca ctcatcgaaa aaaatttgga  5880
ttattagaag agagaggtct gcggcttcca caccgtacag cgtggttttt cttctcggta  5940
taaaagcaaa gttgttttg atacgtgaca gtttcccaca agccaggctg atccttttct  6000
gtcagtccac ttcaccaagc ctgcccttgg acaaggaccc gatgcccaac cccaggcctg  6060
gcaagccctc ggccccttcc ttggcccttg gcccatcccc aggagcctcg cccagctgga  6120
gggctgcacc caaagcctca gacctgctgg gggcccgggg cccaggggga accttccagg  6180
gccgagatct tcgaggcggg gcccatgcct cctcttcttc cttgaacccc atgccaccat  6240
cgcagctgca gctgcccaca ctgcccctag tcatggtggc accctccggg gcacggctgg  6300
gccccttgcc ccacttacag gcactcctcc aggacaggcc acatttcatg caccagctct  6360
caacggtgga tgcccacgcc cggacccctg tgctgcaggt gcacccccctg gagagcccag  6420
ccatgatcag cctcacacca cccaccaccg ccactggggt cttctccctc aaggcccggc  6480
ctggcctccc acctgggatc aacgtggcca gcctggaatg ggtgtccagg gagccggcac  6540
tgctctgcac cttcccaaat cccagtgcac ccaggaagga cagcaccctt tcggctgtgc  6600
cccagagctc ctacccactg ctggcaaatg gtgtctgcaa gtggcccgga tgtgagaagg  6660
tcttcgaaga gccagaggac ttcctcaagc actgccaggc ggaccatctt ctggatgaga  6720
agggcagggc acaatgtctc ctccagagag agatggtaca gtctctggag cagcagctgg  6780
tgctggagaa ggagaagctg agtgccatgc aggcccacct ggctgggaaa atggcactga  6840
ccaaggcttc atctgtggca tcatccgaca agggctcctg ctgcatcgta gctgctggca  6900
gccaaggccc tgtcgtccca gcctggtctg gcccccggga ggcccctgac agcctgtttg  6960
ctgtccggag gcacctgtgg ggtagccatg gaaacagcac attcccagag ttcctccaca  7020
acatggacta cttcaagttc cacaacatgc gacccccttt cacctacgcc acgctcatcc  7080
gctgggccat cctggaggct ccagagaagc agcggacact caatgagatc taccactggt  7140
tcacacgcat gtttgccttc ttcagaaacc atcctgccac ctggaagaac gccatccgcc  7200
acaacctgag tctgcacaag tgctttgtgc gggtggagag cgagaagggg gctgtgtgga  7260
ccgtggatga gctggagttc cgcaagaaac ggagccagag gcccagcagg tgttccaacc  7320
ctacacctgg cccctgatga cctcaagatc aaggaaagga ggatggacga acaggggcca  7380
aactggtggg aggcagaggt ggtgggggca gggatgatag gccctggatg tgcccacagg  7440
gaccaagaag tgaggtttcc actgtcttgc ctgccagggc ccctgttccc ccgctggcag  7500
ccaccccctc ccccatcata tcctttgccc caaggctgct cagaggggcc ccggtcctgg  7560
ccccagcccc cacctccgcc ccagacacac cccccagtcg agccctgcag ccaaacagag  7620
ccttcacaac cagcccacaca gagcctgcct cagctgctcg cacagattac ttcagggctg  7680
gaaaagtcac acagacacac aaaatgtcac aatcctgtcc ctcactcaac acaaacccca  7740
aaacacagag agcctgcctc agtacactca aacaacctca aagctgcatc atcacacaat  7800
cacacacaag cacagccctg acaacccaca caccccaagg cacgcaccca cagccagcct  7860
cagggcccac aggggcactg tcaacacagg ggtgtgccca gaggcctaca cagaagcagc  7920
gtcagtaccc tcaggatctg aggtcccaac acgtgctcgc tcacacacac ggcctgttag  7980
aattcacctg tgtatctcac gcatatgcac acgcacagcc ccccagtggg tctcttgagt  8040
cccgtgcaga cacacacagc cacacacact gccttgccaa aaatacccccg tgtctcccct  8100
gccactcacc tcactcccat tccctgagcc ctgatccatg cctcagctta gactgcagag  8160
gaactactca tttatttggg atccaaggcc cccaacccac agtaccgtcc ccgaattcga  8220
gctcggtacc tttaagacca atgacttaca aggcagctgt agatcttagc cactttttaa  8280
aagaaaaggg gggactggaa gggctaattc actcccaacg aagacaagat cagagcgaga  8340
ttccgtctca aagaaaaaaa aagtaatgaa atgaataaaa tgagtcctag agccagtaaa  8400
tgtcgtaaat gtctcagcta gtcaggtagt aaaaggtctc aactaggcag tggcagagca  8460
ggattcaaat tcagggctgt tgtgatgcct ccgcagactc tgagcgccac ctggtggtaa  8520
tttgtctgtg cctcttctga cgtggaagaa cagcaactaa cacactaaca cggcatttac  8580
tatgggccag ccattgttgc tttttgcttg tactgggtct ctctggttag accagatctg  8640
agcctgggag ctctctggct aactagggaa cccactgctt aagcctcaat aaagcttgcc  8700
ttgagtgctt caagtagtgt gtgcccgtct gttgtgtgac tctggtaact agagatccct  8760
cagacccttt tagtcagtgt ggaaaatctc tagcagtagt agttcatgtc atcttattat  8820
tcagtattta taacttgcaa agaaatgaat atcagagagt gagaggaact tgtttattgc  8880
```

```
agcttataat ggttacaaat aaagcaatag catcacaaat ttcacaaata aagcattttt  8940
tcactgcatt ctagttgtgg tttgtccaaa ctcatcaatg tatcttatca tgtctggctc  9000
tagctatccc gcccctaact ccgcccatcc cgcccctaac tccgcccagt tccgcccatt  9060
ctccgcccca tggctgacta atttttttta tttatgcaga ggccgaggcc gcctcggcct  9120
ctgagctatt ccagaagtag tgaggaggct tttttggagg cctaggcttt tgcgtcgaga  9180
cgtacccaat tcgccctata gtgagtcgta ttacgcgcgc tcactggccg tcgttttaca  9240
acgtcgtgac tgggaaaacc ctggcgttac ccaacttaat cgccttgcag cacatccccc  9300
tttcgccagc tggcgtaata gcgaagaggc ccgcaccgat cgcccttccc aacagttgcg  9360
cagcctgaat ggcgaatggc gcgacgcgcc ctgtagcggc gcattaagcg cggcgggtgt  9420
ggtggttacg cgcagcgtga ccgctacact tgccagcgcc ctagcgcccg ctcctttcgc  9480
tttcttccct tcctttctcg ccacgttcgc cggctttccc cgtcaagctc taaatcgggg  9540
gctcccttta gggttccgat ttagtgcttt acggcacctc gaccccaaaa aacttgatta  9600
gggtgatggt tcacgtagtg ggccatcgcc ctgatagacg gtttttcgcc ctttgacgtt  9660
ggagtccacg ttctttaata gtggactctt gttccaaact ggaacaacac tcaaccctat  9720
ctcggtctat tcttttgatt tataagggat tttgccgatt tcggcctatt ggttaaaaaa  9780
tgagctgatt taacaaaaat ttaacgcgaa ttttaacaaa atattaacgt ttacaatttc  9840
c                                                                  9841

SEQ ID NO: 2           moltype = DNA  length = 20
FEATURE                Location/Qualifiers
misc_feature           1..20
                       note = PCR primer
source                 1..20
                       mol_type = other DNA
                       organism = synthetic construct
SEQUENCE: 2
aagtagtgtg tgcccgtctg                                              20

SEQ ID NO: 3           moltype = DNA  length = 20
FEATURE                Location/Qualifiers
misc_feature           1..20
                       note = PCR primer
source                 1..20
                       mol_type = other DNA
                       organism = synthetic construct
SEQUENCE: 3
cctctggttt ccctttcgct                                              20

SEQ ID NO: 4           moltype = DNA  length = 37
FEATURE                Location/Qualifiers
misc_feature           1..37
                       note = PCR probe
source                 1..37
                       mol_type = other DNA
                       organism = synthetic construct
SEQUENCE: 4
ccctcagacc cttttagtca gtgtggaaaa tctctag                           37

SEQ ID NO: 5           moltype = DNA  length = 20
FEATURE                Location/Qualifiers
misc_feature           1..20
                       note = PCR primer
source                 1..20
                       mol_type = other DNA
                       organism = synthetic construct
SEQUENCE: 5
cgccccctcc tcaccattat                                              20

SEQ ID NO: 6           moltype = DNA  length = 20
FEATURE                Location/Qualifiers
misc_feature           1..20
                       note = PCR primer
source                 1..20
                       mol_type = other DNA
                       organism = synthetic construct
SEQUENCE: 6
catcacaacc atcgctgcct                                              20

SEQ ID NO: 7           moltype = DNA  length = 25
FEATURE                Location/Qualifiers
misc_feature           1..25
                       note = PCR probe
source                 1..25
                       mol_type = other DNA
                       organism = synthetic construct
SEQUENCE: 7
ttaccttgct tgtcggacca aggca                                        25

SEQ ID NO: 8           moltype = DNA  length = 19
```

-continued

```
FEATURE                Location/Qualifiers
misc_feature           1..19
                       note = PCR primer
source                 1..19
                       mol_type = other DNA
                       organism = synthetic construct
SEQUENCE: 8
cagggtctgg gagccaagt                                                      19

SEQ ID NO: 9           moltype = DNA  length = 21
FEATURE                Location/Qualifiers
misc_feature           1..21
                       note = PCR primer
source                 1..21
                       mol_type = other DNA
                       organism = synthetic construct
SEQUENCE: 9
gcacagtgct ggacattgac a                                                   21

SEQ ID NO: 10          moltype = DNA  length = 30
FEATURE                Location/Qualifiers
misc_feature           1..30
                       note = PCR probe
source                 1..30
                       mol_type = other DNA
                       organism = synthetic construct
SEQUENCE: 10
cccaccgaac ccaagaaact agaggagaat                                          30

SEQ ID NO: 11          moltype = DNA  length = 20
FEATURE                Location/Qualifiers
misc_feature           1..20
                       note = PCR primer
source                 1..20
                       mol_type = other DNA
                       organism = synthetic construct
SEQUENCE: 11
tggagttaga ttgtttggga                                                     20

SEQ ID NO: 12          moltype = DNA  length = 24
FEATURE                Location/Qualifiers
misc_feature           1..24
                       note = PCR primer
source                 1..24
                       mol_type = other DNA
                       organism = synthetic construct
SEQUENCE: 12
cacctataaa tccaaatacc ccac                                                24
```